(12) United States Patent
Chen et al.

(10) Patent No.: US 10,280,425 B2
(45) Date of Patent: May 7, 2019

(54) MINICIRCLE DNA RECOMBINANT PARENTAL PLASMID HAVING GENETICALLY ENGINEERED ANTIBODY GENE EXPRESSION CASSETTE, A MINICIRCLE DNA HAVING THE EXPRESSION CASSETTE, AND APPLICATIONS

(71) Applicants: Shenzhen Institutes of Advanced Technology, Nanshan Shenzhen, Guangdong (CN); Shenzhen Hornetcorn Biotechnology Company, Ltd., Futian Shenzhen, Guangdong (CN)

(72) Inventors: Zhiying Chen, Guangdong (CN); Fei Ma, Guangdong (CN); Chengyi He, Guangdong (CN)

(73) Assignees: Shenzhen Institutes of Advanced Technology, Nanshan Shenzhen, Guangdong (CN); Shenzhen Hornetcorn Biotechnology Company, Ltd., Futian Shenzhen, Guangdong (CN)

( * ) Notice: Subject to any disclaimer, the term of this patent is extended or adjusted under 35 U.S.C. 154(b) by 0 days.

(21) Appl. No.: 14/909,060

(22) PCT Filed: Aug. 5, 2014

(86) PCT No.: PCT/CN2014/083741
§ 371 (c)(1),
(2) Date: Jan. 29, 2016

(87) PCT Pub. No.: WO2015/018331
PCT Pub. Date: Feb. 12, 2015

(65) Prior Publication Data
US 2016/0312230 A1 Oct. 27, 2016

(30) Foreign Application Priority Data
Aug. 6, 2013 (CN) .......................... 2013 1 0339305

(51) Int. Cl.
*C12N 15/10* (2006.01)
*C12N 15/64* (2006.01)
*C12N 15/70* (2006.01)
*C12N 15/85* (2006.01)

(52) U.S. Cl.
CPC ............. *C12N 15/64* (2013.01); *C12N 15/10* (2013.01); *C12N 15/70* (2013.01); *C12N 15/85* (2013.01)

(58) Field of Classification Search
None
See application file for complete search history.

(56) References Cited

U.S. PATENT DOCUMENTS

| 9,018,179 B2 | 4/2015 | Kay et al. | |
| 2003/0139363 A1 | 7/2003 | Kay et al. | |
| 2003/0153519 A1 | 8/2003 | Kay et al. | |
| 2006/0160178 A1* | 7/2006 | Rothberg | C07K 16/241 435/69.1 |
| 2010/0099740 A1 | 4/2010 | Kay et al. | |
| 2012/0183477 A1* | 7/2012 | Williams | C07K 16/00 424/9.2 |
| 2013/0312126 A1 | 11/2013 | Kay et al. | |
| 2014/0011981 A1* | 1/2014 | Tesar | C12N 15/74 530/387.3 |
| 2015/0079088 A1* | 3/2015 | Lowman | C07K 16/2809 424/135.1 |

FOREIGN PATENT DOCUMENTS

| CN | 1812999 | * 8/2006 | ......... C07K 16/2809 |
| CN | 102888426 A | 1/2013 | |
| CN | 102978226 A | 3/2013 | |
| CN | 104342453 A | * 8/2013 | ............. C12N 15/70 |
| WO | 2003010180 | 2/2003 | |
| WO | 2004029281 A2 | 4/2004 | |
| WO | 2004106383 A1 | 12/2004 | |
| WO | 2010151793 A1 | 12/2010 | |

OTHER PUBLICATIONS

Chen et al. Minicircle DNA Vectors Devoid of Bacterial DNA Result in Persistent and High-Level Transgene Expression in Vivo, Molecular Therapy vol. 8, No. 3, Sep. 2003.*
Chen et al., A robust system for production of minicircle DNA vectors, vol. 28 No. 12 Dec. 2010 nature biotechnology.*
Lichty et al., Comparison of affinity tags for protein purification, Protein Expression and PuriWcation 41 (2005) 98-105.*
Belteki et al., Site-specific cassette exchange and germline transmission with mouse ES cells expressing φC31 integrase, Mar. 2003, vol. 21, nature biotechnology, pp. 321-324.*

(Continued)

*Primary Examiner* — Addison D Ault
(74) *Attorney, Agent, or Firm* — Bret E. Field; Bozicevic, Field & Francis LLP

(57) ABSTRACT

Provided are a minicircle DNA recombinant parental plasmid having a genetically engineered antibody gene expression cassette and a preparation method for the plasmid, a minicircle DNA having the genetically engineered antibody gene expression cassette, a preparation method for the DNA, and applications thereof, and, a host cell having the minicircle DNA, a preparation method for the cell, and applications thereof. Also provided are a genetically engineered antibody, a preparation method for same, and applications thereof.

2 Claims, 10 Drawing Sheets
Specification includes a Sequence Listing.

(56) References Cited

OTHER PUBLICATIONS

Hu et al. "Research Progress of Minicircle DNA", Letters in Biotechnology, vol. 22, No. 1, Jan. 31, 2011, pp. 104-107. (English abstract only).
Mayrhofer et al. "Use of Minicircle Plasmids for Gene Therapy", Methods in Molecular Biology, vol. 542, Dec. 31, 2009, pp. 87-104.

* cited by examiner (1-a)

(1-b)

(2-a)

(2-b)

(2-c)

(a)  (b)

```
                        SEQUENCE LISTING

<160> NUMBER OF SEQ ID NOS: 34

<210> SEQ ID NO 1
<211> LENGTH: 111
<212> TYPE: PRT
<213> ORGANISM: Artificial Sequence
<220> FEATURE:
<223> OTHER INFORMATION: synthetic amino acid sequence

<400> SEQUENCE: 1

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 2
<211> LENGTH: 124
<212> TYPE: PRT
<213> ORGANISM: Artificial Sequence
<220> FEATURE:
<223> OTHER INFORMATION: synthetic amino acid sequence

<400> SEQUENCE: 2

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45
```

```
Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Thr Ala Tyr
 65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser
                115                 120

<210> SEQ ID NO 3
<211> LENGTH: 106
<212> TYPE: PRT
<213> ORGANISM: Artificial Sequence
<220> FEATURE:
<223> OTHER INFORMATION: synthetic amino acid sequence

<400> SEQUENCE: 3

Asp Ile Gln Leu Thr Gln Ser Pro Ala Ile Met Ser Ala Ser Pro Gly
 1               5                  10                  15

Glu Lys Val Thr Met Thr Cys Arg Ala Ser Ser Ser Val Ser Tyr Met
                20                  25                  30

Asn Trp Tyr Gln Gln Lys Ser Gly Thr Ser Pro Lys Arg Trp Ile Tyr
                35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Asn Pro Leu Thr
                85                  90                  95

Phe Gly Ala Gly Thr Lys Leu Glu Leu Lys
                100                 105

<210> SEQ ID NO 4
<211> LENGTH: 106
<212> TYPE: PRT
<213> ORGANISM: Artificial Sequence
<220> FEATURE:
<223> OTHER INFORMATION: synthetic amino acid sequence

<400> SEQUENCE: 4

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Tyr Met
                20                  25                  30

Asn Trp Tyr Gln Gln Lys Pro Gly Lys Ala Pro Lys Arg Trp Ile Tyr
                35                  40                  45

Asp Thr Ser Lys Val Ala Ser Gly Val Pro Ala Arg Phe Ser Gly Ser
        50                  55                  60

Gly Ser Gly Thr Asp Tyr Ser Leu Thr Ile Asn Ser Leu Glu Ala Glu
 65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
                100                 105
```

```
<210> SEQ ID NO 5
<211> LENGTH: 119
<212> TYPE: PRT
<213> ORGANISM: Artificial Sequence
<220> FEATURE:
<223> OTHER INFORMATION: synthetic amino acid sequence

<400> SEQUENCE: 5

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser
            115

<210> SEQ ID NO 6
<211> LENGTH: 119
<212> TYPE: PRT
<213> ORGANISM: Artificial Sequence
<220> FEATURE:
<223> OTHER INFORMATION: synthetic amino acid sequence

<400> SEQUENCE: 6

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
                100                 105                 110

Thr Thr Val Thr Val Ser Ser
            115

<210> SEQ ID NO 7
<211> LENGTH: 119
<212> TYPE: PRT
<213> ORGANISM: Artificial Sequence
<220> FEATURE:
<223> OTHER INFORMATION: synthetic amino acid sequence

<400> SEQUENCE: 7

Asp Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Val Thr Ile Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
            115
```

<210> SEQ ID NO 8
<211> LENGTH: 18
<212> TYPE: PRT
<213> ORGANISM: Artificial Sequence
<220> FEATURE:
<223> OTHER INFORMATION: synthetic linker amino acid sequence

<400> SEQUENCE: 8

```
Val Glu Gly Gly Ser Gly Gly Ser Gly Gly Ser Gly Gly Ser Gly Gly
1               5                   10                  15

Val Asp
```

<210> SEQ ID NO 9
<211> LENGTH: 18
<212> TYPE: PRT
<213> ORGANISM: Artificial Sequence
<220> FEATURE:
<223> OTHER INFORMATION: synthetic linker amino acid sequence

<400> SEQUENCE: 9

```
Gly Glu Gly Thr Ser Thr Gly Ser Gly Gly Ser Gly Gly Ser Gly Gly
1               5                   10                  15

Ala Asp
```

<210> SEQ ID NO 10
<211> LENGTH: 15
<212> TYPE: PRT
<213> ORGANISM: Artificial Sequence
<220> FEATURE:
<223> OTHER INFORMATION: synthetic linker amino acid sequence

<400> SEQUENCE: 10

```
Gly Gly Gly Gly Ser Gly Gly Gly Gly Ser Gly Gly Gly Gly Ser
1               5                   10                  15
```

<210> SEQ ID NO 11
<211> LENGTH: 5
<212> TYPE: PRT
<213> ORGANISM: Artificial Sequence
<220> FEATURE:
<223> OTHER INFORMATION: synthetic linker amino acid sequence

<400> SEQUENCE: 11

```
Gly Gly Gly Gly Ser
1               5
```

```
<210> SEQ ID NO 12
<211> LENGTH: 333
<212> TYPE: DNA
<213> ORGANISM: Artificial Sequence
<220> FEATURE:
<223> OTHER INFORMATION: synthetic nucleic acid sequence

<400> SEQUENCE: 12
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaa                                    333

<210> SEQ ID NO 13
<211> LENGTH: 372
<212> TYPE: DNA
<213> ORGANISM: Artificial Sequence
<220> FEATURE:
<223> OTHER INFORMATION: synthetic nucleic acid sequence

<400> SEQUENCE: 13
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg agatggtga tactaactac      180 aatggaaagt tcaagggtaa agccactctg actgcagacg aatcctccag cacagcctac     240
atgcaactca gcagcctagc atctgaggac tctgcggtct atttctgtgc aagacgggag     300
actacgacgg taggccgtta ttactatgct atggactact ggggccaagg gaccacggtc     360
accgtctcct cc                                                          372

<210> SEQ ID NO 14
<211> LENGTH: 318
<212> TYPE: DNA
<213> ORGANISM: Artificial Sequence
<220> FEATURE:
<223> OTHER INFORMATION: synthetic nucleic acid sequence

<400> SEQUENCE: 14
gacattcagc tgacccagtc tccagcaatc atgtctgcat ctccagggga aaggtcacc       60 atgacctgca gagccagttc aagtgtaagt tacatgaact ggtaccagca gaagtcaggc     120
acctccccca aaagatggat ttatgacaca tccaaagtgg cttctggagt cccttatcgc     180
ttcagtggca gtgggtctgg gacctcatac tctctcacaa tcagcagcat ggaggctgaa     240
gatgctgcca cttattactg ccaacagtgg agtagtaacc cgctcacgtt cggtgctggg     300
accaagctgg agctgaaa                                                    318

<210> SEQ ID NO 15
<211> LENGTH: 318
<212> TYPE: DNA
<213> ORGANISM: Artificial Sequence
<220> FEATURE:
<223> OTHER INFORMATION: synthetic nucleic acid sequence

<400> SEQUENCE: 15
gacattgtac tgacccagtc tccagcaact ctgtctctgt ctccagggga gcgtgccacc      60
```

```
ctgagctgca gagccagtca aagtgtaagt tacatgaact ggtaccagca gaagccgggc    120
aaggcaccca aaagatggat ttatgacaca tccaaagtgg cttctggagt ccctgctcgc    180
ttcagtggca gtgggtctgg gaccgactac tctctcacaa tcaacagctt ggaggctgaa    240
gatgctgcca cttattactg ccaacagtgg agtagtaacc cgctcacgtt cggtggcggg    300
accaaggtgg agatcaaa                                                  318
```

```
<210> SEQ ID NO 16
<211> LENGTH: 357
<212> TYPE: DNA
<213> ORGANISM: Artificial Sequence
<220> FEATURE:
<223> OTHER INFORMATION: synthetic nucleic acid sequence

<400> SEQUENCE: 16
gatatcaaac tgcagcagtc aggggctgaa ctggcaagac ctggggcctc agtgaagatg     60
tcctgcaaga cttctggcta cacctttact aggtacacga tgcactgggt aaaacagagg    120
cctggacagg gtctggaatg gattggatac attaatccta gccgtggtta tactaattac    180
aatcagaagt tcaaggacaa ggccacattg actacagaca atcctccag cacagcctac     240 atgcaactga gcagcctgac atctgaggac tctgcagtct attactgtgc aagatattat    300
gatgatcatt actgccttga ctactggggc caaggcacca ctctcacagt ctcctca       357
```

```
<210> SEQ ID NO 17
<211> LENGTH: 357
<212> TYPE: DNA
<213> ORGANISM: Artificial Sequence
<220> FEATURE:
<223> OTHER INFORMATION: synthetic nucleic acid sequence

<400> SEQUENCE: 17
gacgtccaac tggtgcagtc aggggctgaa gtgaaaaaac ctggggcctc agtgaaggtg     60
tcctgcaagg cttctggcta cacctttact aggtacacga tgcactgggt aaggcaggca    120
cctggacagg gtctggaatg gattggatac attaatccta gccgtggtta tactaattac    180
gcagacagcg tcaagggccg cttcacaatc actacagaca atccaccag cacagcctac     240 atggaactga gcagcctgcg ttctgaggac actgcaacct attactgtgc aagatattat    300
gatgatcatt actgccttga ctactggggc caaggcacca cggtcaccgt ctcctca       357
```

```
<210> SEQ ID NO 18
<211> LENGTH: 357
<212> TYPE: DNA
<213> ORGANISM: Artificial Sequence
<220> FEATURE:
<223> OTHER INFORMATION: synthetic nucleic acid sequence

<400> SEQUENCE: 18
gacgtccaac tggtgcagtc aggggctgaa gtgaaaaaac ctggggcctc agtgaaggtg     60
tcctgcaagg cttctggcta cacctttact aggtacacga tgcactgggt aaggcaggca    120
cctggacagg gtctggaatg gattggatac attaatccta gccgtggtta tactaattac    180
aatcagaagt tcaaggaccg cgtcacaatc actacagaca atccaccag cacagcctac     240 atggaactga gcagcctgcg ttctgaggac actgcagtct attactgtgc aagatattat    300
gatgatcatt actgccttga ctactggggc caaggcacca cggtcaccgt ctcctca       357
```

```
<210> SEQ ID NO 19
<211> LENGTH: 54
```

```
<212> TYPE: DNA
<213> ORGANISM: Artificial Sequence
<220> FEATURE:
<223> OTHER INFORMATION: synthetic nucleic acid sequence encoding linker

<400> SEQUENCE: 19
gtcgaaggtg aaagtggagg ttctggtgga agtggaggtt caggtggagt cgac          54

<210> SEQ ID NO 20
<211> LENGTH: 54
<212> TYPE: DNA
<213> ORGANISM: Artificial Sequence
<220> FEATURE:
<223> OTHER INFORMATION: synthetic nucleic acid sequence encoding linker

<400> SEQUENCE: 20
ggcgaaggta ctagtactgg ttctggtgga agtggaggtt caggtggagc agac          54

<210> SEQ ID NO 21
<211> LENGTH: 45
<212> TYPE: DNA
<213> ORGANISM: Artificial Sequence
<220> FEATURE:
<223> OTHER INFORMATION: synthetic nucleic acid sequence encoding linker

<400> SEQUENCE: 21
ggtggtggtg gttctggcgg cggcggctcc ggtggtggtg gttct                    45

<210> SEQ ID NO 22
<211> LENGTH: 15
<212> TYPE: DNA
<213> ORGANISM: Artificial Sequence
<220> FEATURE:
<223> OTHER INFORMATION: synthetic nucleic acid sequence encoding linker

<400> SEQUENCE: 22
ggaggtggtg gatcc                                                     15

<210> SEQ ID NO 23
<211> LENGTH: 713
<212> TYPE: DNA
<213> ORGANISM: Artificial Sequence
<220> FEATURE:
<223> OTHER INFORMATION: cytomegalovirus promoter

<400> SEQUENCE: 23
acgcgcgatg tacgggccag atatacgcgt tgacattgat tattgactag ttattaatag    60
taatcaatta cggggtcatt agttcatagc ccatatatgg agttccgcgt tacataactt   120
acggtaaatg gcccgcctgg ctgaccgccc aacgaccccc gcccattgac gtcaataatg   180
acgtatgttc ccatagtaac gccaataggg actttccatt gacgtcaatg ggtggagtat   240
ttacggtaaa ctgcccactt ggcagtacat caagtgtatc atatgccaag tacgccccct   300
attgacgtca atgacggtaa atggcccgcc tggcattatg cccagtacat gaccttatgg   360
gactttccta cttggcagta catctacgta ttagtcatcg ctattaccat ggtgatgcgg   420
ttttggcagt acatcaatgg gcgtggatag cggtttgact cacggggatt tccaagtctc   480
caccccattg acgtcaatgg gagtttgttt tggcaccaaa atcaacggga ctttccaaaa   540
tgtcgtaaca actccgcccc attgacgcaa atgggcggta ggcgtgtacg gtgggaggtc   600
tatataagca gagctctctg gctaactaga acccactg cttactggct atcgaaatt      660 aatacgactc actatagggt gacccaagct ggctagcgtt taaacttaag ctt          713
```

<210> SEQ ID NO 24
<211> LENGTH: 57
<212> TYPE: DNA
<213> ORGANISM: Artificial Sequence
<220> FEATURE:
<223> OTHER INFORMATION: immunoglobulin kappa chain signal peptide
      encoding sequence

<400> SEQUENCE: 24
atgggatgga gctgtatcat cctcttcttg gtagcaacag ctacaggtgt ccactcc        57

<210> SEQ ID NO 25
<211> LENGTH: 24
<212> TYPE: DNA
<213> ORGANISM: Artificial Sequence
<220> FEATURE:
<223> OTHER INFORMATION: flag tag encoding sequence

<400> SEQUENCE: 25
gactacaaag atgatgacga taag                                            24

<210> SEQ ID NO 26
<211> LENGTH: 18
<212> TYPE: DNA
<213> ORGANISM: Artificial Sequence
<220> FEATURE:
<223> OTHER INFORMATION: His6 tag encoding sequence

<400> SEQUENCE: 26
catcatcacc atcatcat                                                   18

<210> SEQ ID NO 27
<211> LENGTH: 259
<212> TYPE: DNA
<213> ORGANISM: Artificial Sequence
<220> FEATURE:
<223> OTHER INFORMATION: bovine growth hormone bpA

<400> SEQUENCE: 27
gtcgactggt gatcagcctc gactgtgcct tctagttgcc agccatctgt tgtttgcccc     60
tcccccgtgc cttccttgac cctggaaggt gccactccca ctgtcctttc ctaataaaat    120
gaggaaattg catcgcattg tctgagtagg tgtcattcta ttctgggggg tggggtgggg    180
caggacagca aggggagga ttgggaagac aatagcaggc atgctgggga tgcggtgggc    240
tctatggaac cagctgggg                                                 259

<210> SEQ ID NO 28
<211> LENGTH: 37
<212> TYPE: DNA
<213> ORGANISM: Artificial Sequence
<220> FEATURE:
<223> OTHER INFORMATION: synthetic recombination sequence

<400> SEQUENCE: 28
cgcgcccggg gagcccaaag gttaccccag ttggggc                              37

<210> SEQ ID NO 29
<211> LENGTH: 112
<212> TYPE: PRT
<213> ORGANISM: Artificial Sequence
<220> FEATURE:
<223> OTHER INFORMATION: synthetic amino acid sequence

<400> SEQUENCE: 29

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

<210> SEQ ID NO 30
<211> LENGTH: 119
<212> TYPE: PRT
<213> ORGANISM: Artificial Sequence
<220> FEATURE:
<223> OTHER INFORMATION: synthetic amino acid sequence

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 31
<211> LENGTH: 35
<212> TYPE: DNA
<213> ORGANISM: Artificial Sequence
<220> FEATURE:
<223> OTHER INFORMATION: synthetic recombination sequence

<400> SEQUENCE: 31
ggtgccaggg cgtgcccttg ggctccccgg gcgcg                                35

<210> SEQ ID NO 32
<211> LENGTH: 37
<212> TYPE: DNA
<213> ORGANISM: Artificial Sequence
<220> FEATURE:
<223> OTHER INFORMATION: synthetic recombination sequence

<400> SEQUENCE: 32
cccaactggg gtaacctttg agttctctca gttgggg                              37

```
<210> SEQ ID NO 33
<211> LENGTH: 336
<212> TYPE: DNA
<213> ORGANISM: Artificial Sequence
<220> FEATURE:
<223> OTHER INFORMATION: synthetic nucleic acid sequence

<400> SEQUENCE: 33
gatatcgtga tgacccagac tccactctcc ctgcccgtca ccctggaga gcccgccagc      60 attagctgca ggtctagcaa gagcctcttg cacagcaatg gcatcactta tttgtattgg    120
tacctgcaaa agccagggca gtctccacag ctcctgattt atcaaatgtc caaccttgtc    180
tctggcgtcc ctgaccggtt ctcaggatcc gggtcaggca ctgatttcac actgaaaatc    240
agcagggtgg aggctgagga tgttggagtt tattactgcg ctcagaatct agaacttcct    300
tacaccttcg gcggagggac caaggtggag atcaaa                              336

<210> SEQ ID NO 34
<211> LENGTH: 357
<212> TYPE: DNA
<213> ORGANISM: Artificial Sequence
<220> FEATURE:
<223> OTHER INFORMATION: synthetic nucleic acid sequence

<400> SEQUENCE: 34
caggtgcaat tggtgcagtc tggcgctgaa gttaagaagc ctgggagttc agtgaaggtc     60
tcctgcaagg cttcaggata cgccttcagc tattcttgga tcaattgggt gcggcaggcg    120
cctggacaag ggctcgagtg gatgggacgg atctttcccg gcgatgggga tactgactac    180
aatgggaaat tcaagggcag agtcacaatt accgccgaca aatccactag cacagcctat    240
atggagctga gcagcctgag atctgaggac acggccgtgt attactgtgc aagaaatgtc    300
tttgatggtt actggcttgt ttactgggc cagggaaccc tggtcaccgt ctcctcc        357
```

MINICIRCLE DNA RECOMBINANT PARENTAL PLASMID HAVING GENETICALLY ENGINEERED ANTIBODY GENE EXPRESSION CASSETTE, A MINICIRCLE DNA HAVING THE EXPRESSION CASSETTE, AND APPLICATIONS

PRIORITY INFORMATION

The present application claims priority to Chinese Application No. 201310339305.0, entitled Minicircle DNA Recombinant Parental Plasmid Having Genetically Engineered Antibody Gene Expression Cassette, A Minicircle DNA Having the Expression Cassette, and Applications, filed on Aug. 6, 2013, and the entire contents of which are hereby incorporated by reference.

FIELD OF THE INVENTION

The present invention relates to the field of biotechnology, particularly to a minicircle DNA recombinant parental plasmid having genetically engineered antibody gene expression cassette, preparation and use thereof, a minicircle DNA having genetically engineered antibody gene expression cassette, preparation and use thereof, a host cell having genetically engineered antibody gene expression cassette, and use thereof, and a genetically engineered antibody, and expression methods and use thereof.

BACKGROUND OF THE INVENTION

In clinical practice, recombinant antibody has been used to treat a variety of diseases, including cancer and autoimmune diseases. Currently, genetically engineered antibody is generally produced in vitro and then injected into the body for treatment. However, this approach has many disadvantages, such as: (1) high cost of the production, packaging, transportation, etc; (2) low purity of protein antibody medicines, side-effects caused by contaminant, potential safety hazard; (3) antibody should be injected repeatedly due to its short half-life period. Sometimes, we need to maintain the effective concentration in vivo via a micropump administration, making it more difficult to apply antibody in clinical practice.

One effective way to avoid the problems caused by a direct injection of protein antibody medicines is to transfect human target cells with therapeutic genes, which is known as gene therapy. In the gene therapy, it is very important to transfer the target genes effectively and safely to host cells for expression via an effective vector. The vectors used in clinical practice mainly comprise recombinant adenoviral vectors, retroviral vectors and plasmid vectors. The viral vectors have high transfection rate, however, it is high in production cost, and its risk of insertion mutagenesis and immunogenicity will bring the risk of carcinogenesis and fatal immune response in patients. Traditional virus vector plasmid vectors are safer than viral vectors, but lower in transfection rate. Further, exogenous genes can only be transiently expressed. If you want a stable and lasting expression of exogenous genes, the vectors must be integrated into the host cell chromosome suffering from the possibility of insertion mutagenesis and exogenous genes silencing. In addition, traditional plasmid vectors contain some hidden signals such as bacterial replication sequences, resistance genes and unmethylated CpG gene sequences, which are necessary in plasmid replications and may cause severe biological safety issues in gene therapy.

SUMMARY OF THE INVENTION

In view of this, a first aspect of the present invention provides a minicircle DNA recombinant parental plasmid having genetically engineered antibody gene expression cassette, wherein minicircle DNA parental plasmid completes the process of recombination of minicircle DNA in host strains, eliminating prokaryotic plasmid elements.

A second aspect of the present invention provides a method for preparing minicircle DNA recombinant parental plasmid having genetically engineered antibody gene expression cassette.

A third aspect of the present invention provides a minicircle DNA having genetically engineered antibody gene expression cassette, wherein the minicircle DNA is separate from host cell genome DNA, providing stable and persistent expression of genetically engineered antibody genes.

A forth aspect of the present invention provides a method for preparing a minicircle DNA having genetically engineered antibody gene expression cassette.

A fifth aspect of the present invention provides host cell containing a minicircle DNA having genetically engineered antibody gene expression cassette.

A sixth aspect of the present invention provides a genetically engineered antibody.

A seventh aspect of the present invention provides an expression method of a genetically engineered antibody.

An eighth aspect of the present invention provides use of minicircle DNA recombinant parental plasmid having genetically engineered antibody gene expression cassette, use of minicircle DNA having genetically engineered antibody gene expression cassette, use of host cell containing a minicircle DNA having genetically engineered antibody gene expression cassette, and use of a genetically engineered antibody.

In a first aspect, the present invention provides a minicircle DNA recombinant parental plasmid having genetically engineered antibody gene expression cassette, wherein said minicircle DNA recombinant parental plasmid is obtained by inserting a gene sequence of genetically engineered antibody gene expression cassette into multiple cloning sites of a minicircle DNA empty plasmid, and said genetically engineered antibody gene expression cassette comprises genetically engineered antibody gene.

As used herein, "minicircle DNA empty plasmid" refers to a plasmid vector having site-specific recombination sites.

As used herein, "plasmid vector" in genetically engineered research refers to a DNA structure possible to insert exogenous DNA and capable of replicating in a recipient cell.

As used herein, the terms "plasmid" and "plasmid vector" are used interchangeably.

As used herein, "minicircle DNA recombinant parental plasmid" has site-specific recombination sites, and "minicircle DNA recombinant parental plasmid" refers to a recombinant parental plasmid that can produce minicircle DNA and backbone DNA through a site-specific recombination of site-specific recombination sites.

As used herein, the terms "minicircle DNA recombinant parental plasmid" and "minicircle DNA parental plasmid" are used interchangeably.

As used herein, "minicircle DNA" refers to a vector that exists mainly in a superhelical structure and is devoid of prokaryotic plasmid backbone DNA sequences. The minicircle DNA, which is free from chromosomal DNA of human and mammalian cells, could provide stable and persistent expression of transcription or target genes.

As used herein, "target gene" is preferably a genetically engineered antibody gene, and the genetically engineered antibody gene is a gene coding for genetically engineered antibody.

As used herein, the terms "minicircle DNA" and "minicircle DNA vector" are used interchangeably.

Compared with viral vectors and plasmid vectors, minicircle DNA reduce the possibility of occurrence of inflammation and silencing of gene expression in vitro or in vivo due to the removal of backbone DNA sequences derived from bacterial, thus providing a more long-term and stronger expression. In addition, clinical safety is improved for the lack of bacterial sequences including resistance marker genes and replication origin in minicircle DNA.

As used herein, "backbone DNA sequences" have DNA sequences functioning replication of bacterial plasmid in a standard plasmid or screening for host containing plasmid. Such DNA sequences include bacterial replication sequences, resistance genes and unmethylated CpG gene sequences, etc.

As used herein the terms "backbone DNA" and "backbone DNA vector" are used interchangeably.

In a preferred embodiment, minicircle DNA parental plasmid is transformed into a host cell, after the induction, the minicircle DNA parental plasmid produces minicircle DNA and backbone DNA through site-specific recombination event of site-specific recombination sites.

Preferably, the host cell is *E. coli*.

Preferably, the site-specific recombination sites are phiC31 site-specific recombination sites, parA site-specific recombination sites or Cre site-specific recombination sites.

As used herein, "site-specific recombination" preferably employs the phiC31 (ΦC31) recombinase system, parA recombinase system or Cre recombinase system reported by Hu Chunsheng, etc. in "Letters in Biotechnology (22 (1): 104-109 (2011))".

Preferably, the backbone DNA contains at least one DNA endonuclease site.

Further preferably, the DNA endonuclease is I-Sce1 endonuclease.

Under such preferred conditions, the backbone DNA is able to be cut and degraded by DNA endonuclease in the host cell, thereby facilitating purification of minicircle DNA. Furthermore, the unrecombined minicircle DNA parental plasmid is also able to be cut and degraded by DNA endonuclease in the host cell because it likewise has DNA endonuclease sites.

In another preferred embodiment, phiC31 recombinase is employed to prepare minicircle DNA, wherein site-specific recombination sites of the minicircle DNA empty plasmid are attB and attP sites. Preferred attB and attP sites are minimal recognition sequences that can be recognized by phiC31 recombinase (attB, attP minimal recognition sequences are shown as SEQ ID NO: 31 and SEQ ID NO: 32).

In yet another preferred embodiment, minicircle DNA parental plasmid constructed herein has attB and attP sites, and the attB and attP sites are presented between the nucleotide sequences of backbone DNA and minicircle DNA.

In particular, the attB and attP sites can be recombinated in the presence of ΦC31 recombinase, making minicircle parental plasmid non-reversibly produce plasmid backbone DNA containing attL site and minicircle DNA containing attR site.

The skilled person in the art can select an appropriate recombinase system as needed, and select appropriate host strains capable of expressing corresponding recombinase, and construct minicircle DNA empty vector that has corresponding site-specific recombination sites.

Preferably, the ΦC31 recombinase expression cassette may be located on minicircle DNA empty plasmid or minicircle DNA recombinant parental plasmid, expressed by minicircle DNA recombinant parental plasmid during the minicircle DNA preparation.

Preferably, the ΦC31 recombinase expression cassette may be located in the host cell genes and expressed by the host cell.

Preferably, the minicircle DNA empty plasmid is p2ΦC31 plasmid or pMC.BESPX plasmid.

As used herein, "p2ΦC31 empty plasmid" has attB and attP sites that can be recombinated in the presence of ΦC31 recombinase.

In particular, methods for constructing empty plasmid p2ΦC31 can be found in Chen Z Y et al., Molecular Therapy, 8 (3), 495-500 (2003); Chen Z Y, et al., Human Gene Therapy, 16 (1), 126-131 (2005) and U.S. Pat. No. 7,897,380 B2.

As used herein, "pMC.BESPX empty plasmid" has attB and attP sites that can be recombinated in the presence of ΦC31 recombinase.

In particular, methods for constructing empty plasmid pMC.BESPX and complete genome sequence can be found in Chen Z Y et al., Nature Biotechnology, 28, (12), 1289-1291 (2010).

The p2ΦC31 plasmid and pMC.BESPX plasmid employed in the preferred embodiments of the present invention differ in that: p2ΦC31 vector has nucleotide sequence encoding ΦC31 recombinase and I-Sce1 endonuclease, while pMC.BESPX vector has no nucleotide sequence encoding ΦC31 recombinase and I-Sce1 endonuclease, such that minicircle DNA parental plasmids prepared by employing pMC.BESPX vector have better quality and reduce contaminations of nucleotide sequence of recombinase and endonuclease. However, pMC.BESPX vector should be used with the *E. coli* ZYCY10P3S2T engineered bacteria having function to encode ΦC31 recombinase and I-Sce1 endonuclease. The pMC.BESPX without nucleotide sequence encoding ΦC31 recombinase (i.e. phiC31 recombinase) and I-Sce1 endonuclease should be used with ZYCY10P3S2T engineered bacteria to generate in vivo site-specific recombination (*E. coli* TOP 10 has no such function) and ultimately produce a minicircle DNA. Accordingly, the p2ΦC31 vector should be used with TOP 10 to generate site-specific recombination in TOP 10, and ultimately produce a minicircle DNA.

As used herein, "genetically engineered antibody gene" encodes genetically engineered antibody, and the genetically engineered antibody includes, but is not limited to natural antibody and recombinant antibody.

As used herein, "genetically engineered antibody gene" encodes genetically engineered antibody, and the genetically engineered antibody includes, but is not limited to human and murine antibody.

As used herein, "genetically engineered antibody gene" encodes genetically engineered antibody, and the genetically engineered antibody includes, but is not limited to therapeutic antibody.

As used herein, "genetically engineered antibody gene" encodes genetically engineered antibody, and the genetically engineered antibody can be single targeting antibody, dual-targeting antibody or multi-targeting antibody.

By "targeting" it is meant an antibody specifically binds to an antigen. By "dual-targeting" it is meant an antibody has two antigen specific binding sites. By "multi-targeting" it is meant an antibody has more than two antigen specific binding sites.

As used herein, "backbone DNA" and "backbone DNA vector" are used interchangeably.

Preferably, the genetically engineered antibody gene expression cassette comprises a promoter operably linked to genetically engineered antibody gene.

More preferably, the promoter is operably linked to genetically engineered antibody gene by at least one of gene sequence of signal peptides and gene sequence of tag.

Still more preferably, the signal peptides are immunoglobulin κ chain signal peptides.

Still more preferably, the tag is at least one of a His tag, GST tag, c-myc tag and Flag tag.

Above signal peptides and tags are preferred in the present invention. The skilled person in the art can select an appropriate signal peptide and label as needed.

As used herein, "genetically engineered antibody gene expression cassette" refers to a gene expression system containing all the necessary elements required for expression of the target polypeptide (genetically engineered antibody in the present invention). The gene expression system normally includes the following elements: promoter, gene sequences encoding polypeptide and terminator. Moreover, coding sequences of signal peptide may be optionally included. These elements are operably linked.

As used herein, "operably linked" refers to a functional arrangement of two or more nucleic acid region or nucleic acid sequences. For example: a promoter region is positioned in certain specific positions with respect to the target nucleic acid sequences, such that the promoter region directs the transcription of the nucleic acid sequences, and the promoter region is "operably linked" to the nucleic acid sequences.

As a preferred form of the first aspect of the present invention, the present invention provides a minicircle DNA recombinant parental plasmid having genetically engineered antibody gene expression cassette, wherein said minicircle DNA recombinant parental plasmid is obtained by inserting a gene sequence of genetically engineered antibody gene expression cassette into multiple cloning sites of a minicircle DNA empty plasmid, and said minicircle DNA empty plasmid is p2ΦC31 plasmid or pMC.BESPX plasmid, and said genetically engineered antibody gene expression cassette comprises a nucleotide sequence selected from the group consisting of:

(a) A-a-B-d-e
(b) A-b-B-d-e
(c) A -B-c-d -e
(d) A-a-b-B-c-d-e
(e) A- a -B-c-d-e
(f) A- a- b-B -d-e
(g) A- b -B-c -d-e where A is a nucleotide sequence encoding a promoter, B is a nucleotide sequence encoding genetically engineered antibody; a, b, c, d, e represent base sequence encoding signal peptides, base sequence encoding Flag tag, base sequence encoding His6 tag, stop codon and polyA tailing signal, respectively; "-" represents "operatively linked" between the gene fragments represented by each base sequence.

The term "nucleotide sequence" used herein refers to a gene or a nucleotide sequence of one strand of a double-stranded DNA. It is understood that, for example, the "genetically engineered antibody gene expression cassette comprises a nucleotide sequence selected from the group consisting of . . . " means "the genetically engineered antibody gene expression cassette" comprises gene fragments of "the nucleotide sequence selected from the group consisting of . . . "

DNA is deoxyribonucleic acid that consists of four deoxynucleotides (dAMP, dGMP, dCMT and dTMP) connected together by 3,5-phosphodiester bonds. It is understood that "base sequence" is used to represent the nucleotide sequence of genes.

As a preferred form of the first aspect of the present invention, the present invention provides a minicircle DNA recombinant parental plasmid having genetically engineered antibody gene expression cassette, wherein said minicircle DNA recombinant parental plasmid is obtained by inserting a gene sequence of genetically engineered antibody gene expression cassette into multiple cloning sites (MCS) of a minicircle DNA empty plasmid, and said minicircle DNA empty plasmid is p2ΦC31 plasmid or pMC.BESPX plasmid, and said genetically engineered antibody gene expression cassette comprises a promoter, base sequence encoding immunoglobulin κ chain signal peptide, base sequence encoding Flag tag, genetically engineered antibody genes, base sequence encoding His6 tag, stop codon and polyA tailing signal linked sequentially.

The term "base sequence" used herein refers to a gene or a nucleotide sequence of one strand of a double-stranded DNA. It is understood that, for example, the "genetically engineered antibody gene expression cassette comprises base sequence encoding immunoglobulin κ chain signal peptide" means the genetically engineered antibody gene expression cassette comprises gene fragments of "the base sequence encoding an immunoglobulin κ chain signal peptide".

Preferably, the genetically engineered antibody genes have base sequence encoding genetically engineered antibody, and the genetically engineered antibody is a dual-targeting specific antibody, and the dual-targeting specific antibody has targeting immune effector cell antigen epitope binding sites and tumor cell antigen epitope binding sites.

More preferably, the immune effector cell is one selected from the group consisting of T lymphocytes, natural killer cells and macrophages.

Further preferably, the tumor cell is one selected from the group consisting of B lymphocytes of tumor cells, leukemia cells, lung cancer cells, gastric cancer cells, colorectal cancer cells, liver cancer cells, esophageal cancer cells, breast cancer cells, pancreatic cancer cells, bladder cancer cells and thyroid cancer cells.

The above preferred immune effector cells and tumor cells would not restrict the use of other immune effector cells and tumor cells in practice.

More preferably, the dual-targeting specific antibody combines with at least one antigen epitope of the tumor cells.

Preferably, methods for constructing empty plasmid p2ΦC31 can be found in Chen Z Y et al., Minicircle DNA vectors devoid of bacterial DNA result in persistent and high-level transgene expression in vivo, Molecular Therapy, 2003, Volume 8, Number 3, 495-500, Chen Z Y et al., Improved production and purification of minicircle DNA vector free of plasmid bacterial sequences and capable of persistent transgene expression in vivo, Human Gene Therapy, 2005, Volume 16, Number 1, 126-131 and U.S. Pat. No. 7,897,380 B2.

Preferably, complete genome sequence of the pMC.BE-SPX plasmid is described in Chen Z Y et al., A robust system for production of minicircle DNA vectors, Nature Biotechnology, 2010, Volume 28, Number 12, 1289-1291.

Preferably, the promoter comprises cytomegalovirus CMV promoter, Rous sarcoma virus RSV promoter, ubiquitin UBC promoter, and elongation factor EF1α promoter.

More preferably, the promoter is the cytomegalovirus CMV promoter.

Preferably, nucleotide sequence of the cytomegalovirus CMV promoter is shown in SEQ ID NO: 23.

The promoter of the present invention can be a eukaryotic promoter, such as cytomegalovirus CMV, RSV, UBC and EF1α, etc. In the present invention, CMV promoter is more preferred for construction of a minicircle DNA parental plasmid. The present invention constructs minicircle DNA parented plasmid by employing different promoters according to different host cells.

Immunoglobulin κ chain signal peptides provided by the present invention is of benefit to secretion of the genetically engineered antibody genes.

Preferably, the base sequence encoding immunoglobulin κ chain signal peptide is shown in SEQ ID NO: 24.

Flag tag provided in the present invention is of benefit to expression of genetically engineered antibody genes, and is better than other commonly used labels such as c-myc, glutathione-S transferase (GST), influenza virus hemagglutinin epitope (HA) and green fluorescent protein (GFP).

Preferably, base sequence of the Flag tag is shown in SEQ ID NO: 25.

His6 tag provided in the present invention is a six-histidine peptide which is of benefit to purification and validation of antibodies in vitro.

Preferably, base sequence of the His6 tag is shown in SEQ ID NO: 26.

Flag tag and histidine tag provided in the present invention are located at upstream and downstream of the genetically engineered antibody genes, respectively. In a particular vector construction process, their positions can be exchanged.

Preferably, base sequence of the stop codon is TTA.

Preferably, the polyA tailing signal is bovine growth hormone polynucleotide bpA or SV40.

Further preferably, the polyA tailing signal is bovine growth hormone polynucleotide bpA.

Preferably, base sequence of the bovine growth hormone polynucleotide bpA is shown in SEQ ID NO: 27.

The polyA tailing signal of the present invention can be SV40, etc. In the present invention, bpA tailing signal is more preferred for construction of a minicircle DNA parental plasmid. The present invention constructs minicircle DNA parented plasmid by employing different tailing signals according to different host cells.

Preferably, the genetically engineered antibody genes have base sequence encoding bispecific single chain antibody amino acid sequence, and connection form of amino acid sequence of the bispecific single chain antibody is one selected from the group consisting of (a)-(h):

(a) $V_L$CD19-linker1-$V_H$CD19-linker2-$V_L$CD3-linker1-$V_H$CD3,
(b) $V_H$CD19-linker1-$V_L$CD19-linker2-$V_L$CD3-linker1-$V_H$CD3,
(c) $V_L$CD19-linker1-$V_H$CD19-linker2-$V_H$CD3-linker1-$V_L$CD3,
(d) $V_H$CD19-linker1-$V_L$CD19-linker2-$V_H$CD3-linker1-$V_L$CD3,
(e) $V_L$CD20-linker1-$V_H$CD20-linker2-$V_L$CD3-linker1-$V_H$CD3,
(f) $V_H$CD20-linker1-$V_L$CD20-linker2-$V_L$CD3-linker1-$V_H$CD3,
(g) $V_L$CD20-linker1-$V_H$CD20-linker2-$V_H$CD3-linker1-$V_L$CD3,
(h) $V_H$CD20-linker1-$V_L$CD20-linker2-$V_H$CD3-linker1-$V_L$CD3, where amino acid sequence of the $V_L$CD19 is shown in SEQ ID NO: 1; amino acid sequence of the $V_H$CD19 is shown in SEQ ID NO: 2; amino acid sequence of the $V_L$CD3 is one selected from the sequences shown in SEQ ID NO: 3 and SEQ ID NO: 4; amino acid sequence of the $V_H$CD3 is one selected from the sequences shown in SEQ ID NO:5, SEQ ID NO:6 and SEQ ID NO:7; amino acid sequence of the linker1 is one selected from the sequences shown in SEQ ID NO:8, SEQ ID NO:9 and SEQ ID NO:10; amino acid sequence of the linker2 is shown in SEQ ID NO: 11; amino acid sequence of the $V_L$CD20 is shown in SEQ ID NO: 29; amino acid sequence of the $V_H$CD20 is shown in SEQ ID NO: 30.

The notation "-" shown between bases, amino acid sequences and polypeptides hereinafter represents sequential linking between bases, amino acid sequences and polypeptides.

Preferably, the bispecific single chain antibody amino acid sequence is an amino acid sequence which shows more than 95% identity (preferably ≥98%) to any sequence represented by (a)-(e).

More preferably, genetically engineered antibody gene provided in the present invention encodes genetically engineered antibody containing amino acid sequence as follows:

(a) amino acid sequence of $V_L$CD19-linker1-$V_H$CD19-linker2-$V_L$CD3-linker1-$V_H$CD3:
SEQ ID NO:1-SEQ ID NO:9-SEQ ID NO:2-SEQ ID NO:11-SEQ ID NO:4-SEQ ID NO:10-SEQ ID NO:6;

(b) amino acid sequence of $V_H$CD19-linker1-$V_L$CD19-linker2-$V_L$CD3-linker1-$V_H$CD3:
SEQ ID NO:2-SEQ ID NO:10-SEQ ID NO:1-SEQ ID NO:11-SEQ ID NO:3-SEQ ID NO:8-SEQ ID NO:5;

(c) amino acid sequence of $V_L$CD19-linker1-$V_H$CD19-linker2-$V_H$CD3-linker1-$V_L$CD3:
SEQ ID NO:1-SEQ ID NO:10-SEQ ID NO:2-SEQ ID NO:11-SEQ ID NO:5-SEQ ID NO:8-SEQ ID NO:3;

(d) amino acid sequence of $V_H$CD19-linker1-$V_L$CD19-linker2-$V_H$CD3-linker1-$V_L$CD3:
SEQ ID NO:2-SEQ ID NO:8-SEQ ID NO:1-SEQ ID NO:11-SEQ ID NO:7-SEQ ID NO:9-SEQ ID NO:4;

(e) amino acid sequence of $V_H$CD20-linker1-$V_L$CD20-linker2-$V_H$CD3-linker1-$V_L$CD3:
SEQ ID NO: 29-SEQ ID NO:10-SEQ ID NO:30-SEQ ID NO:11-SEQ ID NO:7-SEQ ID NO:9-SEQ ID NO:4;

where the notation "-" represents sequential linking between amino acid sequences.

More preferably, genetically engineered antibody genes of the present invention have the base sequence shown below:

(a') base sequence encoding $V_L$CD19-linker1-$V_H$CD19-linker2-$V_L$CD3-linker1-$V_H$CD3:
SEQ ID NO:12-SEQ ID NO:20-SEQ ID NO:13-SEQ ID NO:22-SEQ ID NO:15-SEQ ID NO:21-SEQ ID NO:17;

(b') base sequence encoding $V_HCD19$-linker1-$V_LCD19$-linker2-$V_LCD3$-linker1-$V_HCD3$:
  SEQ ID NO:13-SEQ ID NO:21-SEQ ID NO:12-SEQ ID NO:22-SEQ ID NO:14-SEQ ID NO:19-SEQ ID NO:16;
(c') base sequence encoding $V_LCD19$-linker1-$V_HCD19$-linker2-$V_HCD3$-linker1-$V_LCD3$:
  SEQ ID NO:12-SEQ ID NO:21-SEQ ID NO:13-SEQ ID NO:22-SEQ ID NO:16-SEQ ID NO:19-SEQ ID NO:14;
(d') base sequence encoding $V_HCD19$-linker1-$V_LCD19$-linker2-$V_HCD3$-linker1-$V_LCD3$:
  SEQ ID NO:13-SEQ ID NO:19-SEQ ID NO:12-SEQ ID NO:22-SEQ ID NO:18-SEQ ID NO:20-SEQ ID NO:15;
(e') base sequence encoding $V_LCD20$-linker1-$V_HCD20$-linker2-$V_HCD3$-linker1-$V_LCD3$:
  SEQ ID NO:33-SEQ ID NO:21-SEQ ID NO:34-SEQ ID NO:22-SEQ ID NO:18-SEQ ID NO:20-SEQ ID NO:15;
  where the base sequence encoding SEQ ID NO:29 (amino acid sequence of $V_LCD20$) is SEQ ID NO:33; base sequence encoding SEQ ID NO:30 (amino acid sequence of $V_HCD20$) is SEQ ID NO:34.

All the base sequences represented by (a'), (b'), (c'), (d'), (e') and (f') herein are nucleotide sequence of one strand of two single-stranded genes (DNA fragments), and the notation "-" represents sequential linking between base sequences.

It is understood that one of ordinary skill in the art may adjust the base due to the possibility that nucleotide sequences degenerate or mutate. Although the change of base would lead to changes in codon, it would not cause changes in the amino acid translated by the codon. Commonly encountered leucine codons have various codons, such as UUA, UUG, and CUU.

Preferably, the genetically engineered antibody genes is a base sequence which shows more than 95% identity (preferably ?98%) to any sequence represented by (a')-(e').

Preferably, the genetically engineered antibody genes is a base sequence which shows more than 95% identity (preferably ?98%) to any sequence represented by (a')-(e'). Further, the coding amino acid sequence of the genetically engineered antibody genes is completely or basically identical to coding amino acid sequence of any sequence represented by (a')-(e').

Preferably, the genetically engineered antibody genes are obtained from total gene synthesis or PCR cloning approach.

Preferably, minicircle DNA recombinant parental plasmid having genetically engineered antibody gene expression cassette of the present invention has the genes encoding bispecific single chain antibody, wherein the bispecific single chain antibody has four different domains, namely variable domain of the light chain of binding to human CD19 antigens ($V_LCD19$), variable domain of the heavy chain of binding to human CD19 antigens ($V_HCD19$), variable domain of the light chain of binding to human CD3 antigens ($V_LCD3$), variable domain of the heavy chain of binding to human CD3 antigens ($V_HCD3$). Coding genes of $V_LCD19$, $V_HCD19$, $V_LCD3$ and $V_HCD3$ polypeptide is obtained by screening antibody library, wherein $V_LCD19$ and $V_HCD19$ constitutes functional domain binding to human CD19 antigens, $V_LCD3$ and $V_HCD3$ constitutes functional domain binding to human CD3 antigens, therefore the genetically engineered antibody of the present invention is preferably an anti-CD19×CD3 bispecific single chain antibody (i.e., anti-CD19×CD3 BiTE);

Preferably, preferred structure forms of the anti-CD19× CD3 bispecific single chain antibody are:
$V_LCD19$-linker1-$V_HCD19$-linker2-$V_HCD3$-linker1-$V_LCD3$, where Linker is a linker peptide employing polypeptide sequence that is mainly constituted by glycine and serine. Glycine is the smallest amino acid, and it can increase flexibility of side chain due to its minimal side chain. As the most hydrophilic amino acid, serine could increase hydrophilicity of peptide chain.

Secondly, the genetically engineered antibody gene expression cassette of the present invention has base sequence encoding immunoglobulin κ chain signal peptides and base sequence encoding Flag tag, which makes it possible to add immunoglobulin light κ chain secretion signal peptides and Flag tag at the N-terminal of the genetically engineered antibody. It ensures that antibody is expressed and secreted outside the host cell. In addition, a His6 tag connects the genetically engineered antibody at C-terminal, which is of benefit to purifying antibody by nickel column affinity chromatography.

The anti-CD20×CD3 bispecific single chain antibody (i.e. CD20×CD3 BiTE) has four different domains, namely variable domain of the light chain of binding to human CD20 antigens ($V_LCD20$), variable domain of the heavy chain of binding to human CD20 antigens ($V_HCD20$), variable domain of the light chain of binding to human CD3 antigens ($V_LCD3$), variable domain of the heavy chain of binding to human CD3 antigens ($V_LCD20$).

It is understood that base sequences described herein represent the nucleotide sequence of the gene.

In a second aspect, the present invention provides a method for preparing minicircle DNA recombinant parental plasmid having genetically engineered antibody gene expression cassette, comprising:

(1) providing or preparing DNA fragment having a gene sequence of genetically engineered antibody gene expression cassette, the genetically engineered antibody gene expression cassette comprising genetically engineered antibody gene;

(2) inserting the DNA fragment obtained from step (1) into multiple cloning sites of a minicircle DNA empty plasmid to obtain a minicircle DNA recombinant parental plasmid having genetically engineered antibody gene expression cassette.

As used herein, "minicircle DNA empty plasmid" refers to a plasmid vector having site-specific recombination sites.

As used herein, "plasmid vector" in genetically engineered research refers to a DNA structure possible to insert exogenous DNA and capable of replicating in a recipient cell.

As used herein, the terms "plasmid" and "plasmid vector" are used interchangeably.

As used herein, "minicircle DNA recombinant parental plasmid" has site-specific recombination sites, and "minicircle DNA recombinant parental plasmid" refers to a recombinant parental plasmid that can produce minicircle DNA and backbone DNA through a site-specific recombination of site-specific recombination sites.

As used herein, the terms "minicircle DNA recombinant parental plasmid" and "minicircle DNA parental plasmid" are used interchangeably.

As used herein, "minicircle DNA" refers to a vector that exists mainly in a superhelical structure and is devoid of prokaryotic plasmid backbone DNA sequences. The minicircle DNA, which is free from chromosomal DNA of human and mammalian cells, could provide stable and persistent expression of transcription or target genes.

As used herein, "target gene" is preferably a genetically engineered antibody gene, and the genetically engineered antibody gene is a gene coding for genetically engineered antibody.

As used herein, the terms "minicircle DNA" and "minicircle DNA vector" are used interchangeably.

Compared with viral vectors and plasmid vectors, minicircle DNA reduce the possibility of occurrence of inflammation and silencing of gene expression in vitro or in vivo due to the removal of backbone DNA sequences derived from bacterial, thus providing a more long-term and stronger expression. In addition, clinical safety is improved for the lack of bacterial sequences including resistance marker genes and replication origin in minicircle DNA.

As used herein, "backbone DNA sequences" have DNA sequences functioning replication of bacterial plasmid in a standard plasmid or screening for host containing plasmid. Such DNA sequences include bacterial replication sequences, resistance genes, unmethylated CpG gene sequences, etc.

As used herein the terms "backbone DNA" and "backbone DNA vector" are used interchangeably.

In a preferred embodiment, minicircle DNA parental plasmid is transformed into a host cell, after the induction, the minicircle DNA parental plasmid produces minicircle DNA and backbone DNA through site-specific recombination event of site-specific recombination sites.

Preferably, the host cell is *E. coli*.

Preferably, the site-specific recombination sites are phiC31 site-specific recombination sites, parA site-specific recombination sites or Cre site-specific recombination sites.

As used herein, "site-specific recombination" preferably employs the phiC31 (ΦC31) recombinase system, parA recombinase system or Cre recombinase system reported by Hu Chunsheng, etc. in "Letters in Biotechnology (22 (1): 104-109 (2011))".

Preferably, the backbone DNA contains at least one DNA endonuclease site.

Further preferably, the DNA endonuclease is I-Sce1 endonuclease.

Under such preferred conditions, the backbone DNA is able to be cut and degraded by DNA endonuclease in the host cell, thereby facilitating purification of minicircle DNA. Furthermore, the unrecombined minicircle DNA parental plasmid is also able to be cut and degraded by DNA endonuclease in the host cell because it likewise has DNA endonuclease sites.

In another preferred embodiment, phiC31 recombinase is employed to prepare minicircle DNA, wherein site-specific recombination sites of the minicircle DNA empty plasmid are attB and attP sites. Preferred attB and attP sites are minimal recognition sequences that can be recognized by phiC31 recombinase (attB, attP minimal recognition sequences are shown as SEQ ID NO: 31 and SEQ ID NO: 32).

In yet another preferred embodiment, minicircle DNA parental plasmid constructed herein has attB and attP sites, and the attB and attP sites are presented between the nucleotide sequences of backbone DNA and minicircle DNA.

In particular, the attB and attP sites can be recombinated in the presence of ΦC31 recombinase, making minicircle parental plasmid non-reversibly produce plasmid backbone DNA containing attL site and minicircle DNA containing attR site.

The skilled person in the art can select an appropriate recombinase system as needed, and select appropriate host strains capable of expressing corresponding recombinase, and construct minicircle DNA empty vector that has corresponding site-specific recombination sites.

Preferably, the ΦC31 recombinase expression cassette may be located on minicircle DNA empty plasmid or minicircle DNA recombinant parental plasmid, expressed by minicircle DNA recombinant parental plasmid during the minicircle DNA preparation.

Preferably, the ΦC31 recombinase expression cassette may be located in the host cell genes and expressed by the host cell.

Preferably, the minicircle DNA empty plasmid is p2ΦC31 plasmid or pMC.BESPX plasmid.

As used herein, "p2ΦC31 empty plasmid" has attB and attP sites that can be recombinated in the presence of ΦC31 recombinase.

In particular, methods for constructing empty plasmid p2ΦC31 can be found in Chen Z Y et al., Molecular Therapy, 8 (3), 495-500 (2003); Chen Z Y, et al., Human Gene Therapy, 16 (1), 126-131 (2005) and U.S. Pat. No. 7,897,380 B2.

As used herein, "pMC.BESPX empty plasmid" has attB and attP sites that can be recombinated in the presence of ΦC31 recombinase.

In particular, methods for constructing empty plasmid pMC.BESPX and complete genome sequence can be found in Chen Z Y et al., Nature Biotechnology, 28, (12), 1289-1291 (2010).

The p2ΦC31 plasmid and pMC.BESPX plasmid employed in the preferred embodiments of the present invention differ in that: p2ΦC31 vector has nucleotide sequence encoding ΦC31 recombinase and I-Sce1 endonuclease, while pMC.BESPX vector has no nucleotide sequence encoding ΦC31 recombinase and I-Sce1 endonuclease, such that minicircle DNA parental plasmids prepared by employing pMC.BESPX vector have better quality and reduce contaminations of nucleotide sequence of recombinase and endonuclease. However, pMC.BESPX vector should be used with the *E. coli* ZYCY10P3S2T engineered bacteria having function to encode ΦC31 recombinase and I-Sce1 endonuclease. The pMC.BESPX without nucleotide sequence encoding ΦC31 recombinase (i.e. phiC31 recombinase) and I-Sce1 endonuclease should be used with ZYCY10P3S2T engineered bacteria to generate in vivo site-specific recombination (*E. coli* TOP 10 has no such function) and ultimately produce a minicircle DNA. Accordingly, the p2ΦC31 vector should be used with TOP 10 to generate site-specific recombination in TOP 10, and ultimately produce a minicircle DNA.

As used herein, "genetically engineered antibody gene" encodes genetically engineered antibody, and the genetically engineered antibody includes, but is not limited to natural antibody and recombinant antibody.

As used herein, "genetically engineered antibody gene" encodes genetically engineered antibody, and the genetically engineered antibody includes, but is not limited to human and murine antibody.

As used herein, "genetically engineered antibody gene" encodes genetically engineered antibody, and the genetically engineered antibody includes, but is not limited to therapeutic antibody.

As used herein, "genetically engineered antibody gene" encodes genetically engineered antibody, and the genetically engineered antibody can be single targeting antibody, dual-targeting antibody or multi-targeting antibody.

By "targeting" it is meant an antibody specifically binds to an antigen. By "dual-targeting" it is meant an antibody has two antigen specific binding sites. By "multi-targeting" it is meant an antibody has more than two antigen specific binding sites.

As used herein, "backbone DNA" and "backbone DNA vector" are used interchangeably.

Preferably, the genetically engineered antibody gene expression cassette comprises a promoter operably linked to genetically engineered antibody gene.

More preferably, the promoter is operably linked to genetically engineered antibody gene by at least one of gene sequence of signal peptides and gene sequence of tag.

Still more preferably, the signal peptides are immunoglobulin κ chain signal peptides.

Still more preferably, the tag is at least one of a His tag, GST tag, c-myc tag and Flag tag.

Above signal peptides and tags are preferred in the present invention. The skilled person in the art can select an appropriate signal peptide and label as needed.

As used herein, "genetically engineered antibody gene expression cassette" refers to a gene expression system containing all the necessary elements required for expression of the target polypeptide (genetically engineered antibody in the present invention). The gene expression system normally includes the following elements: promoter, gene sequences encoding polypeptide and terminator. Moreover, coding sequences of signal peptide may be optionally included. These elements are operably linked.

As used herein, "operably linked" refers to a functional arrangement of two or more nucleic acid region or nucleic acid sequences. For example: a promoter region is positioned in certain specific positions with respect to the target nucleic acid sequences, such that the promoter region directs the transcription of the nucleic acid sequences, and the promoter region is "operably linked" to the nucleic acid sequences.

As a preferred form of the second aspect of the present invention, the present invention provides a method for preparing minicircle DNA recombinant parental plasmid having genetically engineered antibody gene expression cassette, comprising:

(1) providing or preparing DNA fragment having a gene sequence of genetically engineered antibody gene expression cassette, the genetically engineered antibody gene expression cassette comprising genetically engineered antibody gene;

(2) inserting the DNA fragment obtained from step (1) into multiple cloning sites of a minicircle DNA empty plasmid to obtain a minicircle DNA recombinant parental plasmid having genetically engineered antibody gene expression cassette;

and the minicircle DNA empty plasmid is p2ΦC31 plasmid or pMC.BESPX plasmid, and said genetically engineered antibody gene expression cassette comprises a nucleotide sequence selected from the group consisting of:

(a) A-a-B-d-e
(b) A-b-B-d-e
(c) A -B-c-d -e
(d) A-a- b-B-c-d-e
(e) A- a -B-c-d-e
(f) A- a- b-B -d-e
(g) A- b -B-c -d-e where A is a nucleotide sequence encoding a promoter, B is a nucleotide sequence encoding genetically engineered antibody; a, b, c, d, e represent base sequence encoding signal peptides, base sequence encoding Flag tag, base sequence encoding His6 tag, stop codon and polyA tailing signal, respectively; "-" represents "operatively linked" between the gene fragments represented by each base sequence.

DNA is deoxyribonucleic acid that consists of four deoxynucleotides (dAMP, dGMP, dCMT and dTMP) connected together by 3,5-phosphodiester bonds. It is understood that "base sequence" is used to represent the nucleotide sequence of genes.

As another preferred form of the second aspect of the present invention, the present invention provides a method for preparing minicircle DNA recombinant parental plasmid having genetically engineered antibody gene expression cassette, comprising:

(1) providing or preparing DNA fragment having base sequence encoding immunoglobulin chain signal peptides, base sequence encoding Flag tag, genetically engineered antibody gene, base sequence encoding His6 tag and stop codon linked sequentially;

(2) inserting the DNA fragment obtained from step (1) into multiple cloning sites of expression vector to obtain recombinant expression vector having genetically engineered antibody gene expression cassette, a promoter and polyA tailing signal presenting at the ends of the multiple cloning sites of expression vector;

(3) cutting the recombinant expression vector obtained from step (2) with two enzymes to produce DNA fragments containing genetically engineered antibody gene expression cassette, and then inserting the DNA fragments containing genetically engineered antibody gene expression cassette into p2ΦC31 plasmid or pMC.BESPX plasmid to obtain minicircle DNA recombinant parental plasmid having genetically engineered antibody gene expression cassette, where the genetically engineered antibody gene expression cassette comprises a promoter, base sequence encoding immunoglobulin κ chain signal peptide, base sequence encoding Flag tag, genetically engineered antibody genes, base sequence encoding His6 tag, stop codon and polyA tailing signal linked sequentially. Preferably, the genetically engineered antibody genes have base sequence encoding genetically engineered antibody, and the genetically engineered antibody is a dual-targeting specific antibody, and the dual-targeting specific antibody has targeting immune effector cell antigen epitope binding sites and tumor cell antigen epitope binding sites.

More preferably, the immune effector cell is one selected from the group consisting of T lymphocytes, natural killer cells and macrophages.

Further preferably, the tumor cell is one selected from the group consisting of B lymphocytes of tumor cells, leukemia cells, lung cancer cells, gastric cancer cells, colorectal cancer cells, liver cancer cells, esophageal cancer cells, breast cancer cells, pancreatic cancer cells, bladder cancer cells and thyroid cancer cells.

More preferably, the dual-targeting specific antibody combines with at least one antigen epitope of the tumor cells.

Preferably, in step (2), the promoter expression vector comprises cytomegalovirus CMV promoter, Rous sarcoma virus RSV promoter, ubiquitin UBC promoter, and elongation factor EF1α promoter.

More preferably, in step (2), the promoter expression vector is the cytomegalovirus CMV promoter.

Preferably, in step (2), the polyA tailing signal expression vector is bovine growth hormone polynucleotide bpA or SV40.

Further preferably, in step (2), the polyA tailing signal expression vector is bovine growth hormone polynucleotide bpA.

The promoter of the present invention can be a eukaryotic promoter, such as cytomegalovirus CMV, RSV, UBC and EF1α, etc. In the present invention, CMV promoter is more preferred for construction of a minicircle DNA parental plasmid. The present invention constructs minicircle DNA parental plasmid by employing different promoters according to different host cells. The polyA tailing signal of the present invention can be SV40, etc. In the present invention, bpA tailing signal is more preferred for construction of a minicircle DNA parental plasmid. The present invention constructs minicircle DNA parental plasmid by employing different tailing signals according to different host cells.

Preferably, in step (2), the expression vector carries cytomegalovirus CMV promoter and bovine growth hormone polynucleotide bpA tailing signal. Multiple cloning sites present between the CMV and bpA of the expression vector, and may be inserted gene fragment of interest.

As used herein, "multiple cloning sites" refers to a synthesis sequence of vector that contains multiple restriction endonuclease recognition sites and provides multiple inserting sites and solutions for exogenous DNA.

By "gene fragment of interest" it is meant targeting gene.

Preferably, the target gene is a gene coding for genetically engineered antibody.

As used herein, "genetically engineered antibody" includes, but is not limited to natural antibody, antigen, and antigen epitope, and recombinant antibody, antigen, and antigen epitope.

As used herein, "genetically engineered antibody" includes, but is not limited to human and murine antibody.

As used herein, "genetically engineered antibody gene" includes, but is not limited to therapeutic antibody.

As used herein, "genetically engineered antibody gene" can be single targeting antibody, dual-targeting antibody or multi-targeting antibody.

By "targeting" it is meant an antibody specifically binds to an antigen. By "dual-targeting" it is meant an antibody has two antigen specific binding sites. By "multi-targeting" it is meant an antibody has more than two antigen specific binding sites. Preferably, in step (2), the expression vector is pCMV.bpA expression vector.

The term "pCMV.bpA expression vector" as described herein refers to a plasmid vector capable of replicating and amplifying gene fragments that are inserted into multiple cloning sites of colon bacillus. The "pCMV.bpA expression vector" multiple cloning site have CMV promotor in upstream and bpA tailing signal in downstream.

It is understood that the skilled person in the art can select an alternative expression vector of pCMV.bpA as needed, thus adding different promotor to upstream of the DNA fragments from step (1).

Preferably, CMV upstream of the pCMV.bpA expression vector and downstream of the bpA tailing signal have SpeI and OMI endonuclease sites (shown in FIG. 1-b), respectively. The SpeI and OMI endonuclease sites are constructed according to the method described in Molecular Cloning: A Laboratory Manual (version 4). More preferably, the method for constructing pCMV.bpA expression vector containing CMV promotor, bpA tailing signal, SpeI and OMI endonuclease sites comprises the following steps: (a) selecting an empty plasmid vector; (b) inserting CMV promotor and bpA tailing signal into different multiple cloning sites, wherein there are multiple cloning sites for exogenous genes between the CMV promoter and the bpA tailing signal; upstream of the CMV promotor have SpeI endonuclease sites, while downstream of the bpA tailing signal have Psp OMI endonuclease sites.

In a preferred embodiment of the present invention, the pCMV.bpA expression vector has SpeI endonuclease sites and Psp OMI endonuclease sites. There are nucleotide sequence of CMV promotor and nucleotide sequence of bpA tailing signal between SpeI endonuclease sites and Psp OMI endonuclease sites. There are HindIII endonuclease sites and EcoRI endonuclease sites between nucleotide sequence of CMV promotor and nucleotide sequence of bpA tailing signal.

In another preferred embodiment of the present invention, the step of providing or preparing DNA fragments (step (1)) involves:

(1-1) synthesizing DNA fragments by using complete genome sequence or PCR cloning approach, the DNA fragments comprise HindIII enzyme sites, base sequence encoding immunoglobulin κ chain signal peptide, base sequence encoding Flag tag, genetically engineered antibody genes, base sequence encoding His6 tag, stop codon and EcoRI enzyme linked sequentially;

(1-2) inserting the DNA fragments obtained from (1-1) into HindIII and EcoRI sites of pUC57 vector (plasmid map see FIG. 1-a) to amplify, cutting the target fragment with two enzymes and recovering the DNA fragment.

Preferably, in step (2), the DNA fragment obtained from step (1) is inserted into HindIII and EcoRI sites of pCMV. bpA vector to obtain pCMV.bpA. Bab recombinant expression vector.

Preferably, in step (3), the recombinant expression vector obtained from step (2) is cut with two enzymes to obtain DNA fragment having genetically engineered antibody gene cassette. The step of inserting the DNA fragment having genetically engineered antibody gene cassette into p2ΦC31 plasmid or pMC.BESPX plasmid comprises:

(1-4) providing p2ΦC31 plasmid or pMC.BESPX plasmid;

(1-5) cutting the p2ΦC31 plasmid or pMC.BESPX plasmid with SpeI and Psp OMI endonuclease, and recovering linear plasmid;

(1-6) cutting pCMV. bpA. Bab recombinant expression vector with SpeI and Psp OMI endonuclease, and recovering DNA fragment having genetically engineered antibody gene cassette;

(1-7) connecting the linear plasmid recovered from step (1-5) with the DNA fragment recovered from step (1-6) using DNA ligase to obtain minicircle DNA recombinant parental plasmid p2ΦC31.Bab or pMC.Bab having genetically engineered antibody gene cassette, wherein the genetically engineered antibody gene cassette comprises cytomegalovirus CMV promoter, base sequence encoding immunoglobulin κ chain signal peptide, base sequence encoding Flag tag, genetically engineered antibody genes, base sequence encoding His6 tag, stop codon, polyA tailing signal and bovine growth hormone polynucleotide bpA tailing signal linked sequentially.

Preferably, in step (1-7), the DNA ligase is T4 DNA ligase.

Preferably, the genetically engineered antibody genes have base sequence encoding bispecific single chain antibody amino acid sequence, and connection form of amino acid sequence of the bispecific single chain antibody is one selected from the group consisting of (a)-(h):

(a) V$_L$CD19-linker1-V$_H$CD19-linker2-V$_L$CD3-linker1-V$_H$CD3,
(b) V$_H$CD19-linker1-V$_L$CD19-linker2-V$_L$CD3-linker1-V$_H$CD3,
(c) V$_L$CD19-linker1-V$_H$CD19-linker2-V$_H$CD3-linker1-V$_L$CD3,
(d) V$_H$CD19-linker1-V$_L$CD19-linker2-V$_H$CD3-linker1-V$_L$CD3,
(e) V$_L$CD20-linker1-V$_H$CD20-linker2-V$_L$CD3-linker1-V$_H$CD3,
(f) V$_H$CD20-linker1-V$_L$CD20-linker2-V$_L$CD3-linker1-V$_H$CD3,
(g) V$_L$CD20-linker1-V$_H$CD20-linker2-V$_H$CD3-linker1-V$_L$CD3,
(h) V$_H$CD20-linker1-V$_L$CD20-linker2-V$_H$CD3-linker1-V$_L$CD3, where amino acid sequence of the V$_L$CD19 is shown in SEQ ID NO: 1; amino acid sequence of the V$_H$CD19 is shown in SEQ ID NO: 2; amino acid sequence of the V$_L$CD3 is one selected from the sequences shown in SEQ ID NO: 3 and SEQ ID NO: 4; amino acid sequence of the V$_H$CD3 is one selected from the sequences shown in SEQ ID NO:5, SEQ ID NO:6 and SEQ ID NO:7; amino acid sequence of the linker1 is one selected from the sequences shown in SEQ ID NO:8, SEQ ID NO:9 and SEQ ID NO:10; amino acid sequence of the linker2 is shown in SEQ ID NO: 11; amino acid sequence of the V$_L$CD20 is shown in SEQ ID NO: 29; amino acid sequence of the V$_H$CD20 is shown in SEQ ID NO: 30.

Preferably, the bispecific single chain antibody amino acid sequence is an amino acid sequence which shows more than 95% identity (preferably ≥98%) to any sequence represented by (a)-(e).

More preferably, genetically engineered antibody gene provided in the present invention encodes genetically engineered antibody containing amino acid sequence as follows:
(a) amino acid sequence of V$_L$CD19-linker1-V$_H$CD19-linker2-V$_L$CD3-linker1-V$_H$CD3:
    SEQ ID NO:1-SEQ ID NO:9-SEQ ID NO:2-SEQ ID NO:11-SEQ ID NO:4-SEQ ID NO:10-SEQ ID NO:6;
(b) amino acid sequence of V$_H$CD19-linker1-V$_L$CD19-linker2-V$_L$CD3-linker1-V$_H$CD3:
    SEQ ID NO:2-SEQ ID NO:10-SEQ ID NO:1-SEQ ID NO:11-SEQ ID NO:3-SEQ ID NO:8-SEQ ID NO:5;
(c) amino acid sequence of V$_L$CD19-linker1-V$_H$CD19-linker2-V$_H$CD3-linker1-V$_L$CD3:
    SEQ ID NO:1-SEQ ID NO:10-SEQ ID NO:2-SEQ ID NO:11-SEQ ID NO:5-SEQ ID NO:8-SEQ ID NO:3;
(d) amino acid sequence of V$_H$CD19-linker1-V$_L$CD19-linker2-V$_H$CD3-linker1-V$_L$CD3:
    SEQ ID NO:2-SEQ ID NO:8-SEQ ID NO:1-SEQ ID NO:11-SEQ ID NO:7-SEQ ID NO:9-SEQ ID NO:4.
(e) amino acid sequence of V$_H$CD20-linker1-V$_L$CD20-linker2-V$_H$CD3-linker1-V$_L$CD3:
    SEQ ID NO: 29-SEQ ID NO:10-SEQ ID NO:30-SEQ ID NO:11-SEQ ID NO:7-SEQ ID NO:9-SEQ ID NO:4.

where the notation "-" represents sequential linking between amino acid sequences.

More preferably, genetically engineered antibody genes of the present invention have the base sequence shown below:
(a') base sequence encoding V$_L$CD19-linker1-V$_H$CD19-linker2-V$_L$CD3-linker1-V$_H$CD3:
    SEQ ID NO:12-SEQ ID NO:20-SEQ ID NO:13-SEQ ID NO:22-SEQ ID NO:15-SEQ ID NO:21-SEQ ID NO:17;
(b') base sequence encoding V$_H$CD19-linker1-V$_L$CD19-linker2-V$_L$CD3-linker1-V$_H$CD3:
    SEQ ID NO:13-SEQ ID NO:21-SEQ ID NO:12-SEQ ID NO:22-SEQ ID NO:14-SEQ ID NO:19-SEQ ID NO:16;
(c') base sequence encoding V$_L$CD19-linker1-V$_H$CD19-linker2-V$_H$CD3-linker1-V$_L$CD3:
    SEQ ID NO:12-SEQ ID NO:21-SEQ ID NO:13-SEQ ID NO:22-SEQ ID NO:16-SEQ ID NO:19-SEQ ID NO:14;
(d') base sequence encoding V$_H$CD19-linker1-V$_L$CD19-linker2-V$_H$CD3-linker1-V$_L$CD3:
    SEQ ID NO:13-SEQ ID NO:19-SEQ ID NO:12-SEQ ID NO:22-SEQ ID NO:18-SEQ ID NO:20-SEQ ID NO:15;
(e') base sequence encoding V$_L$CD20-linker1-V$_H$CD20-linker2-V$_H$CD3-linker1-V$_L$CD3:
    SEQ ID NO:33-SEQ ID NO:21-SEQ ID NO:34-SEQ ID NO:22-SEQ ID NO:18-SEQ ID NO:20-SEQ ID NO:15;

where the base sequence encoding SEQ ID NO:29 (amino acid sequence of V$_L$CD20) is SEQ ID NO:33; base sequence encoding SEQ ID NO:30 (amino acid sequence of V$_H$CD20) is SEQ ID NO:34.

All the base sequences represented by (a'), (b'), (c'), (d'), (e') and (f') herein are nucleotide sequence of one strand of two single-stranded genes (DNA fragments), and the notation "-" represents sequential linking between base sequences.

It is understood that one of ordinary skill in the art may adjust the base due to the possibility that nucleotide sequences degenerate or mutate. Although the change of base would lead to changes in codon, it would not cause changes in the amino acid translated by the codon. Commonly encountered leucine codons have various codons, such as UUA, UUG, and CUU.

Preferably, the genetically engineered antibody genes is a base sequence which shows more than 95% identity (preferably ?98%) to any sequence represented by (a')-(e').

Preferably, the genetically engineered antibody genes is a base sequence which shows more than 95% identity (preferably ?98%) to any sequence represented by (a')-(e'). Further, the coding amino acid sequence of the genetically engineered antibody genes is completely or basically identical to coding amino acid sequence of any sequence represented by (a')-(e').

Preferably, the genetically engineered antibody genes are obtained from total gene synthesis or PCR cloning approach.

Preferably, minicircle DNA recombinant parental plasmid having genetically engineered antibody gene expression cassette of the present invention has the genes encoding bispecific single chain antibody, wherein the bispecific single chain antibody has four different domains, namely variable domain of the light chain of binding to human CD19 antigens (V$_L$CD19), variable domain of the heavy chain of binding to human CD19 antigens (V$_H$CD19), variable domain of the light chain of binding to human CD3 antigens (V$_L$CD3), variable domain of the heavy chain of binding to human CD3 antigens (V$_H$CD3). Coding genes of V$_L$CD19, V$_H$CD19, V$_L$CD3 and V$_H$CD3 polypeptide is obtained by screening antibody library, wherein V$_L$CD19 and V$_H$CD19 constitutes functional domain binding to human CD19 antigens, V$_L$CD3 and V$_H$CD3 constitutes functional domain binding to human CD3 antigens, therefore the genetically engineered antibody of the present invention is preferably an anti-CD19×CD3 bispecific single chain antibody (i.e., anti-CD19×CD3 BiTE);

Preferably, preferred structure forms of the anti-CD19× CD3 bispecific single chain antibody are:

$V_L$CD19-linker1-$V_H$CD19-linker2-$V_H$CD3-linker1-$V_L$CD3, where Linker is a linker peptide employing polypeptide sequence that is mainly constituted by glycine and serine. Glycine is the smallest amino acid, and it can increase flexibility of side chain due to its minimal side chain. As the most hydrophilic amino acid, serine could increase hydrophilicity of peptide chain.

Secondly, the genetically engineered antibody gene expression cassette of the present invention has base sequence encoding immunoglobulin κ chain signal peptides and base sequence encoding Flag tag, which makes it possible to add immunoglobulin light κ chain secretion signal peptides and Flag tag at the N-terminal of the genetically engineered antibody. It ensures that antibody is expressed and secreted outside the host cell. In addition, a His6 tag connects the genetically engineered antibody at C-terminal, which is of benefit to purifying antibody by nickel column affinity chromatography.

The anti-CD20×CD3 bispecific single chain antibody (i.e. CD20×CD3 BiTE) has four different domains, namely variable domain of the light chain of binding to human CD20 antigens ($V_L$CD20), variable domain of the heavy chain of binding to human CD20 antigens ($V_H$CD20), variable domain of the light chain of binding to human CD3 antigens ($V_L$CD3), variable domain of the heavy chain of binding to human CD3 antigens ($V_L$CD20).

It is understood that base sequences described herein represent the nucleotide sequence of the gene.

The p2ΦC31 plasmid and pMC.BESPX plasmid of the present invention differ in that: p2ΦC31 vector has nucleotide sequence encoding ΦC31 recombinase and I-SceI endonuclease, while pMC.BESPX vector has no nucleotide sequence encoding ΦC31 recombinase and I-SceI endonuclease, such that minicircle DNA parental plasmids prepared by employing pMC.BESPX vector have better quality and reduce contaminations of nucleotide sequence of recombinase and endonuclease. However, pMC.BESPX vector should be used with the E. coli ZYCY10P3S2T engineered bacteria having function to encode ΦC31 recombinase and I-SceI endonuclease. The pMC.BESPX without nucleotide sequence encoding ΦC31 recombinase (i.e. phiC31 recombinase) and I-SceI endonuclease should be used with ZYCY10P3S2T engineered bacteria to generate in vivo site-specific recombination (E. coli TOP 10 has no such function) and ultimately produce a minicircle DNA. Accordingly, the p2ΦC31 vector should be used with TOP 10 to generate site-specific recombination in TOP10, and ultimately produce a minicircle DNA.

Preferably, the minicircle DNA having genetically engineered antibody gene expression cassette of the present invention can be used for preparing medicines for cancers.

Preferably, the minicircle DNA having genetically engineered antibody gene expression cassette of the present invention can be used for preparing medicines for CD19 positive cancer disease.

In a third aspect, the present invention provides a minicircle DNA having genetically engineered antibody gene expression cassette, wherein said minicircle DNA is circular DNA having genetically engineered antibody gene expression cassette, and said genetically engineered antibody gene expression cassette comprises genetically engineered antibody gene.

As used herein, "minicircle DNA" refers to a vector that exists mainly in a superhelical structure and is devoid of prokaryotic plasmid backbone DNA sequences. The minicircle DNA, which is free from chromosomal DNA of human and mammalian cells, could provide stable and persistent expression of transcription or target genes.

As used herein, the terms "minicircle DNA" and "minicircle DNA vector" are used interchangeably.

Compared with viral vectors and plasmid vectors, minicircle DNA reduce the possibility of occurrence of inflammation and silencing of gene expression in vitro or in vivo due to the removal of backbone DNA sequences derived from bacterial, thus providing a more long-term and stronger expression. In addition, clinical safety is improved for the lack of bacterial sequences including resistance marker genes and replication origin in minicircle DNA.

In a preferred embodiment, the minicircle DNA is produced from minicircle DNA recombinant parental plasmid through a site-specific recombination of site-specific recombination sites.

As used herein, the minicircle DNA recombinant parental plasmid is obtained by inserting a gene sequence of genetically engineered antibody gene expression cassette into multiple cloning sites of a minicircle DNA empty plasmid, and said genetically engineered antibody gene expression cassette comprises genetically engineered antibody gene.

As used herein, "minicircle DNA empty plasmid" refers to a plasmid vector having site-specific recombination sites.

As used herein, "plasmid vector" in genetically engineered research refers to a DNA structure possible to insert exogenous DNA and capable of replicating in a recipient cell.

As used herein, the terms "plasmid" and "plasmid vector" are used interchangeably.

As used herein, "minicircle DNA recombinant parental plasmid" has site-specific recombination sites, and "minicircle DNA recombinant parental plasmid" refers to a recombinant parental plasmid that can produce minicircle DNA and backbone DNA through a site-specific recombination of site-specific recombination sites.

As used herein, the terms "minicircle DNA recombinant parental plasmid" and "minicircle DNA parental plasmid" are used interchangeably.

As used herein, "backbone DNA sequences" have DNA sequences functioning replication of bacterial plasmid in a standard plasmid or screening for host containing plasmid. Such DNA sequences include bacterial replication sequences, resistance genes, unmethylated CpG gene sequences, etc.

As used herein the terms "backbone DNA" and "backbone DNA vector" are used interchangeably.

In a preferred embodiment, minicircle DNA parental plasmid is transformed into a host cell, after the induction, the minicircle DNA parental plasmid produces minicircle DNA and backbone DNA through site-specific recombination event of site-specific recombination sites.

Preferably, the host cell is E. coli.

Preferably, the site-specific recombination sites are phiC31 site-specific recombination sites, parA site-specific recombination sites or Cre site-specific recombination sites.

As used herein, "site-specific recombination" preferably employs the phiC31 ΦC31) recombinase system, parA recombinase system or Cre recombinase system reported by Hu Chunsheng, etc. in "Letters in Biotechnology (22 (1): 104-109 (2011))".

Preferably, the backbone DNA contains at least one DNA endonuclease site.

Further preferably, the DNA endonuclease is I-SceI endonuclease.

Under such preferred conditions, the backbone DNA is able to be cut and degraded by DNA endonuclease in the host cell, thereby facilitating purification of minicircle DNA. Furthermore, the unrecombined minicircle DNA parental plasmid is also able to be cut and degraded by DNA endonuclease in the host cell because it likewise has DNA endonuclease sites.

In another preferred embodiment, phiC31 recombinase is employed to prepare minicircle DNA, wherein site-specific recombination sites of the minicircle DNA empty plasmid are attB and attP sites. Preferred attB and attP sites are minimal recognition sequences that can be recognized by phiC31 recombinase (attB, attP minimal recognition sequences are shown as SEQ ID NO: 31 and SEQ ID NO: 32).

In yet another preferred embodiment, minicircle DNA parental plasmid constructed herein has attB and attP sites, and the attB and attP sites are presented between the nucleotide sequences of backbone DNA and minicircle DNA.

In particular, the attB and attP sites can be recombinated in the presence of ΦC31 recombinase, making minicircle parental plasmid non-reversibly produce plasmid backbone DNA containing attL site and minicircle DNA containing attR site.

The skilled person in the art can select an appropriate recombinase system as needed, and select appropriate host strains capable of expressing corresponding recombinase, and construct minicircle DNA empty vector that has corresponding site-specific recombination sites.

Preferably, the ΦC31 recombinase expression cassette may be located on minicircle DNA empty plasmid or minicircle DNA recombinant parental plasmid, expressed by minicircle DNA recombinant parental plasmid during the minicircle DNA preparation.

Preferably, the ΦC31 recombinase expression cassette may be located in the host cell genes and expressed by the host cell.

Preferably, the minicircle DNA empty plasmid is p2ΦC31 plasmid or pMC.BESPX plasmid.

As used herein, "p2ΦC31 empty plasmid" has attB and attP sites that can be recombinated in the presence of ΦC31 recombinase.

In particular, methods for constructing empty plasmid p2ΦC31 can be found in Chen Z Y et al., Molecular Therapy, 8 (3), 495-500 (2003); Chen Z Y, et al., Human Gene Therapy, 16 (1), 126-131 (2005) and U.S. Pat. No. 7,897,380 B2.

As used herein, "pMC.BESPX empty plasmid" has attB and attP sites that can be recombinated in the presence of ΦC31 recombinase.

In particular, methods for constructing empty plasmid pMC.BESPX and complete genome sequence can be found in Chen Z Y et al., Nature Biotechnology, 28, (12), 1289-1291 (2010).

The p2ΦC31 plasmid and pMC.BESPX plasmid employed in the preferred embodiments of the present invention differ in that: p2ΦC31 vector has nucleotide sequence encoding ΦC31 recombinase and I-Sce1 endonuclease, while pMC.BESPX vector has no nucleotide sequence encoding ΦC31 recombinase and I-Sce1 endonuclease, such that minicircle DNA parental plasmids prepared by employing pMC.BESPX vector have better quality and reduce contaminations of nucleotide sequence of recombinase and endonuclease. However, pMC.BESPX vector should be used with the *E. coli* ZYCY10P3S2T engineered bacteria having function to encode ΦC31 recombinase and I-Sce1 endonuclease. The pMC.BESPX without nucleotide sequence encoding ΦC31 recombinase (i.e. phiC31 recombinase) and I-Sce1 endonuclease should be used with ZYCY10P3S2T engineered bacteria to generate in vivo site-specific recombination (*E. coli* TOP 10 has no such function) and ultimately produce a minicircle DNA. Accordingly, the p2ΦC31 vector should be used with TOP 10 to generate site-specific recombination in TOP10, and ultimately produce a minicircle DNA.

As used herein, "genetically engineered antibody gene" encodes genetically engineered antibody, and the genetically engineered antibody includes, but is not limited to natural antibody and recombinant antibody.

As used herein, "genetically engineered antibody gene" encodes genetically engineered antibody, and the genetically engineered antibody includes, but is not limited to human and murine antibody.

As used herein, "genetically engineered antibody gene" encodes genetically engineered antibody, and the genetically engineered antibody includes, but is not limited to therapeutic antibody.

As used herein, "genetically engineered antibody gene" encodes genetically engineered antibody, and the genetically engineered antibody can be single targeting antibody, dual-targeting antibody or multi-targeting antibody.

By "targeting" it is meant an antibody specifically binds to an antigen. By "dual-targeting" it is meant an antibody has two antigen specific binding sites. By "multi-targeting" it is meant an antibody has more than two antigen specific binding sites.

As used herein, "backbone DNA" and "backbone DNA vector" are used interchangeably.

Preferably, the genetically engineered antibody gene expression cassette comprises a promoter operably linked to genetically engineered antibody gene.

More preferably, the promoter is operably linked to genetically engineered antibody gene by at least one of gene sequence of signal peptides and gene sequence of tag.

Still more preferably, the signal peptides are immunoglobulin κ chain signal peptides.

Still more preferably, the tag is at least one of a His tag, GST tag, c-myc tag and Flag tag.

Above signal peptides and tags are preferred in the present invention. The skilled person in the art can select an appropriate signal peptide and label as needed.

As used herein, "genetically engineered antibody gene expression cassette" refers to a gene expression system containing all the necessary elements required for expression of the target polypeptide (genetically engineered antibody in the present invention). The gene expression system normally includes the following elements: promoter, gene sequences encoding polypeptide and terminator. Moreover, coding sequences of signal peptide may be optionally included. These elements are operably linked.

As used herein, "operably linked" refers to a functional arrangement of two or more nucleic acid region or nucleic acid sequences. For example: a promoter region is positioned in certain specific positions with respect to the target nucleic acid sequences, such that the promoter region directs the transcription of the nucleic acid sequences, and the promoter region is "operably linked" to the nucleic acid sequences.

As a preferred form of the third aspect of the present invention, the present invention provides a minicircle DNA having genetically engineered antibody gene expression cassette, wherein the minicircle DNA is circular DNA having attR site and genetically engineered antibody gene expression cassette, and said gene expression cassette comprises a nucleotide sequence selected from the group consisting of:
(a) A-a-B-d-e
(b) A-b-B-d-e
(c) A -B-c-d -e
(d) A-a- b-B-c-d-e
(e) A- a -B-c-d-e
(f) A- a- b-B -d-e
(g) A- b -B-c -d-e where A is a nucleotide sequence encoding a promoter, B is a nucleotide sequence encoding genetically engineered antibody; a, b, c, d, e represent base sequence encoding signal peptides, base sequence encoding Flag tag, base sequence encoding His6 tag, stop codon and polyA tailing signal, respectively; "-" represents "operatively linked" between the gene fragments represented by each base sequence.

DNA is deoxyribonucleic acid that consists of four deoxynucleotides (dAMP, dGMP, dCMT and dTMP) connected together by 3,5-phosphodiester bonds. It is understood that "base sequence" is used to represent the nucleotide sequence of genes.

As a preferred form of the third aspect of the present invention, the present invention provides a minicircle DNA having genetically engineered antibody gene expression cassette, wherein the minicircle DNA is circular DNA having attR site and genetically engineered antibody gene expression cassette, and said gene expression cassette comprises a promoter, base sequence encoding immunoglobulin κ chain signal peptide, base sequence encoding Flag tag, genetically engineered antibody genes, base sequence encoding His6 tag, stop codon and polyA tailing signal linked sequentially.

Preferably, the genetically engineered antibody genes have base sequence encoding genetically engineered antibody, and the genetically engineered antibody is a dual-targeting specific antibody, and the dual-targeting specific antibody has targeting immune effector cell antigen epitope binding sites and tumor cell antigen epitope binding sites.

More preferably, the immune effector cell is one selected from the group consisting of T lymphocytes, natural killer cells and macrophages.

Further preferably, the tumor cell is one selected from the group consisting of B lymphocytes of tumor cells, leukemia cells, lung cancer cells, gastric cancer cells, colorectal cancer cells, liver cancer cells, esophageal cancer cells, breast cancer cells, pancreatic cancer cells, bladder cancer cells and thyroid cancer cells.

More preferably, the dual-targeting specific antibody combines with at least one antigen epitope of the tumor cells.

Preferably, the promoter comprises cytomegalovirus CMV promoter, RSV promoter, UBC promoter, and EF1α promoter.

More preferably, the promoter is the cytomegalovirus CMV promoter.

Preferably, the polyA tailing signal is bovine growth hormone polynucleotide bpA or SV40.

Further preferably, the polyA tailing signal is bovine growth hormone polynucleotide bpA.

The promoter of the present invention can be a eukaryotic promoter, such as cytomegalovirus CMV, RSV, UBC and EF1α, etc. In the present invention, CMV promoter is more preferred for construction of a minicircle DNA. The present invention constructs minicircle DNA by employing different promoters according to different host cells. The polyA tailing signal of the present invention can be SV40, etc. In the present invention, bpA tailing signal is more preferred for construction of a minicircle DNA. The present invention constructs minicircle DNA by employing different tailing signals according to different host cells.

Preferably, the genetically engineered antibody genes have base sequence encoding bispecific single chain antibody amino acid sequence, and the bispecific single chain antibody genes have base sequence encoding bispecific single chain antibody amino acid sequence, and connection form of amino acid sequence of the bispecific single chain antibody is one selected from the group consisting of (a)-(h):

(a) $V_L$CD19-linker1-$V_H$CD19-linker2-$V_L$CD3-linker1-$V_H$CD3,
(b) $V_H$CD19-linker1-$V_L$CD19-linker2-$V_L$CD3-linker1-$V_H$CD3,
(c) $V_L$CD19-linker1-$V_H$CD19-linker2-$V_H$CD3-linker1-$V_L$CD3,
(d) $V_H$CD19-linker1-$V_L$CD19-linker2-$V_H$CD3-linker1-$V_L$CD3,
(e) $V_L$CD20-linker1-$V_H$CD20-linker2-$V_L$CD3-linker1-$V_H$CD3,
(f) $V_H$CD20-linker1-$V_L$CD20-linker2-$V_L$CD3-linker1-$V_H$CD3,
(g) $V_L$CD20-linker1-$V_H$CD20-linker2-$V_H$CD3-linker1-$V_L$CD3,
(h) $V_H$CD20-linker1-$V_L$CD20-linker2-$V_H$CD3-linker1-$V_L$CD3, where amino acid sequence of the $V_L$CD19 is shown in SEQ ID NO: 1; amino acid sequence of the $V_H$CD19 is shown in SEQ ID NO: 2; amino acid sequence of the $V_L$CD3 is one selected from the sequences shown in SEQ ID NO: 3 and SEQ ID NO: 4; amino acid sequence of the $V_H$CD3 is one selected from the sequences shown in SEQ ID NO:5, SEQ ID NO:6 and SEQ ID NO:7; amino acid sequence of the linker1 is one selected from the sequences shown in SEQ ID NO:8, SEQ ID NO:9 and SEQ ID NO:10; amino acid sequence of the linker2 is shown in SEQ ID NO: 11; amino acid sequence of the $V_L$CD20 is shown in SEQ ID NO: 29; amino acid sequence of the $V_H$CD20 is shown in SEQ ID NO: 30.

Preferably, the bispecific single chain antibody amino acid sequence is an amino acid sequence which shows more than 95% identity (preferably ?98%) to any sequence represented by (a)-(e).

Preferably, the minicircle DNA having genetically engineered antibody gene expression cassette is produced from minicircle DNA recombinant parental plasmid through a site-specific recombination in host strains.

Preferably, base sequence of the attR site is shown in SEQ ID NO:28.

More preferably, genetically engineered antibody gene provided in the present invention encodes genetically engineered antibody containing amino acid sequence as follows:
(a) amino acid sequence of $V_L$CD19-linker1-$V_H$CD19-linker2-$V_L$CD3-linker1-$V_H$CD3:
  SEQ ID NO:1-SEQ ID NO:9-SEQ ID NO:2-SEQ ID NO:11-SEQ ID NO:4-SEQ ID NO:10-SEQ ID NO:6;
(b) amino acid sequence of $V_H$CD19-linker1-$V_L$CD19-linker2-$V_L$CD3-linker1-$V_H$CD3:
  SEQ ID NO:2-SEQ ID NO:10-SEQ ID NO:1-SEQ ID NO:11-SEQ ID NO:3-SEQ ID NO:8-SEQ ID NO:5;
(c) amino acid sequence of $V_L$CD19-linker1-$V_H$CD19-linker2-$V_H$CD3-linker1-$V_L$CD3:
  SEQ ID NO:1-SEQ ID NO:10-SEQ ID NO:2-SEQ ID NO:11-SEQ ID NO:5-SEQ ID NO:8-SEQ ID NO:3;

(d) amino acid sequence of $V_HCD19$-linker1-$V_LCD19$-linker2-$V_HCD3$-linker1-$V_LCD3$:
  SEQ ID NO:2-SEQ ID NO:8-SEQ ID NO:1-SEQ ID NO:11-SEQ ID NO:7-SEQ ID NO:9-SEQ ID NO:4;
(e) amino acid sequence of $V_HCD20$-linker1-$V_LCD20$-linker2-$V_HCD3$-linker1-$V_LCD3$:
  SEQ ID NO: 29-SEQ ID NO:10-SEQ ID NO:30-SEQ ID NO:11-SEQ ID NO:7-SEQ ID NO:9-SEQ ID NO:4;
  where the notation "-" represents sequential linking between amino acid sequences.

More preferably, genetically engineered antibody genes of the present invention have the base sequence shown below:

(a') base sequence encoding $V_LCD19$-linker1-$V_HCD19$-linker2-$V_LCD3$-linker1-$V_HCD3$:
  SEQ ID NO:12-SEQ ID NO:20-SEQ ID NO:13-SEQ ID NO:22-SEQ ID NO:15-SEQ ID NO:21-SEQ ID NO:17;
(b') base sequence encoding $V_HCD19$-linker1-$V_LCD19$-linker2-$V_LCD3$-linker1-$V_HCD3$:
  SEQ ID NO:13-SEQ ID NO:21-SEQ ID NO:12-SEQ ID NO:22-SEQ ID NO:14-SEQ ID NO:19-SEQ ID NO:16;
(c') base sequence encoding $V_LCD19$-linker1-$V_HCD19$-linker2-$V_HCD3$-linker1-$V_LCD3$:
  SEQ ID NO:12-SEQ ID NO:21-SEQ ID NO:13-SEQ ID NO:22-SEQ ID NO:16-SEQ ID NO:19-SEQ ID NO:14;
(d') base sequence encoding $V_HCD19$-linker1-$V_LCD19$-linker2-$V_HCD3$-linker1-$V_LCD3$:
  SEQ ID NO:13-SEQ ID NO:19-SEQ ID NO:12-SEQ ID NO:22-SEQ ID NO:18-SEQ ID NO:20-SEQ ID NO:15;
(e') base sequence encoding $V_LCD20$-linker1-$V_HCD20$-linker2-$V_HCD3$-linker1-$V_LCD3$:
  SEQ ID NO:33-SEQ ID NO:21-SEQ ID NO:34-SEQ ID NO:22-SEQ ID NO:18-SEQ ID NO:20-SEQ ID NO:15;
  where the base sequence encoding SEQ ID NO:29 (amino acid sequence of $V_LCD20$) is SEQ ID NO:33; base sequence encoding SEQ ID NO:30 (amino acid sequence of $V_HCD20$) is SEQ ID NO:34.

All the base sequences represented by (a'), (b'), (c'), (d'), (e') and (f') herein are nucleotide sequence of one strand of two single-stranded genes (DNA fragments), and the notation "-" represents sequential linking between base sequences.

It is understood that one of ordinary skill in the art may adjust the base due to the possibility that nucleotide sequences degenerate or mutate. Although the change of base would lead to changes in codon, it would not cause changes in the amino acid translated by the codon. Commonly encountered leucine codons have various codons, such as UUA, UUG, and CUU.

Preferably, the genetically engineered antibody genes is a base sequence which shows more than 95% identity (preferably ?98%) to any sequence represented by (a')-(e').

Preferably, the genetically engineered antibody genes is a base sequence which shows more than 95% identity (preferably ?98%) to any sequence represented by (a')-(e'). Further, the coding amino acid sequence of the genetically engineered antibody genes is completely or basically identical to coding amino acid sequence of any sequence represented by (a')-(e').

Preferably, the genetically engineered antibody genes are obtained from total gene synthesis or PCR cloning approach.

Preferably, minicircle DNA recombinant parental plasmid having genetically engineered antibody gene expression cassette of the present invention has the genes encoding bispecific single chain antibody, wherein the bispecific single chain antibody has four different domains, namely variable domain of the light chain of binding to human CD19 antigens ($V_LCD19$), variable domain of the heavy chain of binding to human CD19 antigens ($V_HCD19$), variable domain of the light chain of binding to human CD3 antigens ($V_LCD3$), variable domain of the heavy chain of binding to human CD3 antigens ($V_HCD3$). Coding genes of $V_LCD19$, $V_HCD19$, $V_LCD3$ and $V_HCD3$ polypeptide is obtained by screening antibody library, wherein $V_LCD19$ and $V_HCD19$ constitutes functional domain binding to human CD19 antigens, $V_LCD3$ and $V_HCD3$ constitutes functional domain binding to human CD3 antigens, therefore the genetically engineered antibody of the present invention is preferably an anti-CD19×CD3 bispecific single chain antibody (i.e., anti-CD19×CD3 BiTE);

Preferably, preferred structure forms of the anti-CD19×CD3 bispecific single chain antibody are:
$V_LCD19$-linker1-$V_HCD19$-linker2-$V_HCD3$-linker1-$V_LCD3$, where Linker is a linker peptide employing polypeptide sequence that is mainly constituted by glycine and serine. Glycine is the smallest amino acid, and it can increase flexibility of side chain due to its minimal side chain. As the most hydrophilic amino acid, serine could increase hydrophilicity of peptide chain.

Secondly, the genetically engineered antibody gene expression cassette of the present invention has base sequence encoding immunoglobulin κ chain signal peptides and base sequence encoding Flag tag, which makes it possible to add immunoglobulin light κ chain secretion signal peptides and Flag tag at the N-terminal of the genetically engineered antibody. It ensures that antibody is expressed and secreted outside the host cell. In addition, a His6 tag connects the genetically engineered antibody at C-terminal, which is of benefit to purifying antibody by nickel column affinity chromatography.

The anti-CD20×CD3 bispecific single chain antibody (i.e. CD20×CD3 BiTE) has four different domains, namely variable domain of the light chain of binding to human CD20 antigens ($V_LCD20$), variable domain of the heavy chain of binding to human CD20 antigens ($V_HCD20$), variable domain of the light chain of binding to human CD3 antigens ($V_LCD3$), variable domain of the heavy chain of binding to human CD3 antigens ($V_LCD3$).

It is understood that base sequences described herein represent the nucleotide sequence of the gene.

Compared with traditional plasmid vectors, minicircle DNA having genetically engineered antibody of the present invention improve the clinical safety for the lack of bacterial sequences including resistance marker genes and replication origin in minicircle DNA, thus improving clinical safety and providing a more long-term and stronger expression of genetically engineered antibody genes. Compared with virus vectors, the minicircle DNA without the risk of insertion mutagenesis and immunogenicity is low-cost. Therefore, minicircle DNA containing genetically engineered antibody of the present invention is a kind of safe, efficient and economical therapy vector.

In a forth aspect, the present invention provides a method for preparing a minicircle DNA having genetically engineered antibody gene expression cassette, comprising:

(1) providing or preparing minicircle DNA recombinant parental plasmid having genetically engineered antibody gene expression cassette, said minicircle DNA recombinant parental plasmid is obtained by inserting a gene sequence of genetically engineered antibody gene expression cassette into multiple cloning sites of a minicircle DNA empty plasmid, the minicircle DNA recombinant parental plasmid having site-specific recombination sites;

(2) transforming host strains with the minicircle DNA recombinant parental plasmid having genetically engineered antibody gene expression cassette obtained from step (1), producing minicircle DNA and backbone DNA through a site-specific recombination of site-specific recombination sites in the presence of a recombinase;

(3) isolating and purifying the minicircle DNA and backbone DNA obtained from step (2), the minicircle DNA is circular DNA having genetically engineered antibody gene expression cassette, and said genetically engineered antibody gene expression cassette comprises genetically engineered antibody gene.

As used herein, "minicircle DNA" refers to a vector that exists mainly in a superhelical structure and is devoid of prokaryotic plasmid backbone DNA sequences. The minicircle DNA, which is free from chromosomal DNA of human and mammalian cells, could provide stable and persistent expression of transcription or target genes.

As used herein, the terms "minicircle DNA" and "minicircle DNA vector" are used interchangeably.

Compared with viral vectors and plasmid vectors, minicircle DNA reduce the possibility of occurrence of inflammation and silencing of gene expression in vitro or in vivo due to the removal of backbone DNA sequences derived from bacterial, thus providing a more long-term and stronger expression. In addition, clinical safety is improved for the lack of bacterial sequences including resistance marker genes and replication origin in minicircle DNA.

As used herein, the minicircle DNA recombinant parental plasmid is obtained by inserting a gene sequence of genetically engineered antibody gene expression cassette into multiple cloning sites of a minicircle DNA empty plasmid, and said genetically engineered antibody gene expression cassette comprises genetically engineered antibody gene.

As used herein, "minicircle DNA empty plasmid" refers to a plasmid vector having site-specific recombination sites.

As used herein, "plasmid vector" in genetically engineered research refers to a DNA structure possible to insert exogenous DNA and capable of replicating in a recipient cell.

As used herein, the terms "plasmid" and "plasmid vector" are used interchangeably.

As used herein, "minicircle DNA recombinant parental plasmid" has site-specific recombination sites, and "minicircle DNA recombinant parental plasmid" refers to a recombinant parental plasmid that can produce minicircle DNA and backbone DNA through a site-specific recombination of site-specific recombination sites.

As used herein, the terms "minicircle DNA recombinant parental plasmid" and "minicircle DNA parental plasmid" are used interchangeably.

As used herein, "backbone DNA sequences" have DNA sequences functioning replication of bacterial plasmid in a standard plasmid or screening for host containing plasmid. Such DNA sequences include bacterial replication sequences, resistance genes, unmethylated CpG gene sequences, etc.

As used herein the terms "backbone DNA" and "backbone DNA vector" are used interchangeably.

When bacteria or fungus are employed as host cells, the "host cell" and "host strains" are used interchangeably.

Preferably, the host cell is *E. coli*.

Preferably, the site-specific recombination sites are phiC31 site-specific recombination sites, parA site-specific recombination sites or Cre site-specific recombination sites.

As used herein, "site-specific recombination" preferably employs the phiC31 (ΦC31) recombinase system, parA recombinase system or Cre recombinase system reported by Hu Chunsheng, etc. in "Letters in Biotechnology (22 (1): 104-109 (2011))".

Preferably, the backbone DNA contains at least one DNA endonuclease site.

Further preferably, the DNA endonuclease is I-Sce1 endonuclease.

Under such preferred conditions, the backbone DNA is able to be cut and degraded by DNA endonuclease in the host cell, thereby facilitating purification of minicircle DNA. Furthermore, the unrecombined minicircle DNA parental plasmid is also able to be cut and degraded by DNA endonuclease in the host cell because it likewise has DNA endonuclease sites.

In another preferred embodiment, phiC31 recombinase is employed to prepare minicircle DNA, wherein site-specific recombination sites of the minicircle DNA empty plasmid are attB and attP sites. Preferred attB and attP sites are minimal recognition sequences that can be recognized by phiC31 recombinase (attB, attP minimal recognition sequences are shown as SEQ ID NO: 31 and SEQ ID NO: 32).

In yet another preferred embodiment, minicircle DNA parental plasmid constructed herein has attB and attP sites, and the attB and attP sites are presented between the nucleotide sequences of backbone DNA and minicircle DNA.

In particular, the attB and attP sites can be recombinated in the presence of ΦC31 recombinase, making minicircle parental plasmid non-reversibly produce plasmid backbone DNA containing attL site and minicircle DNA containing attR site.

The skilled person in the art can select an appropriate recombinase system as needed, and select appropriate host strains capable of expressing corresponding recombinase, and construct minicircle DNA empty vector that has corresponding site-specific recombination sites.

Preferably, the ΦC31 recombinase expression cassette may be located on minicircle DNA empty plasmid or minicircle DNA recombinant parental plasmid, expressed by minicircle DNA recombinant parental plasmid during the minicircle DNA preparation.

Preferably, the ΦC31 recombinase expression cassette may be located in the host cell genes and expressed by the host cell.

Preferably, the minicircle DNA empty plasmid is p2ΦC31 plasmid or pMC.BESPX plasmid.

As used herein, "p2ΦC31 empty plasmid" has attB and attP sites that can be recombinated in the presence of ΦC31 recombinase.

In particular, methods for constructing empty plasmid p2ΦC31 can be found in Chen Z Y et al., Molecular Therapy, 8 (3), 495-500 (2003); Chen Z Y, et al., Human Gene Therapy, 16 (1), 126-131 (2005) and U.S. Pat. No. 7,897,380 B2.

As used herein, "pMC.BESPX empty plasmid" has attB and attP sites that can be recombinated in the presence of ΦC31 recombinase.

In particular, methods for constructing empty plasmid pMC.BESPX and complete genome sequence can be found in Chen Z Y et al., Nature Biotechnology, 28, (12), 1289-1291 (2010).

The p2ΦC31 plasmid and pMC.BESPX plasmid employed in the preferred embodiments of the present invention differ in that: p2ΦC31 vector has nucleotide sequence encoding ΦC31 recombinase and I-SceI endonuclease, while pMC.BESPX vector has no nucleotide sequence encoding ΦC31 recombinase and I-SceI endonuclease, such that minicircle DNA parental plasmids prepared by employing pMC.BESPX vector have better quality and reduce contaminations of nucleotide sequence of recombinase and endonuclease. However, pMC.BESPX vector should be used with the E. coli ZYCY10P3S2T engineered bacteria having function to encode ΦC31 recombinase and I-SceI endonuclease. The pMC.BESPX without nucleotide sequence encoding ΦC31 recombinase (i.e. phiC31 recombinase) and I-SceI endonuclease should be used with ZYCY10P3S2T engineered bacteria to generate in vivo site-specific recombination (E. coli TOP 10 has no such function) and ultimately produce a minicircle DNA. Accordingly, the p2ΦC31 vector should be used with TOP 10 to generate site-specific recombination in TOP 10, and ultimately produce a minicircle DNA.

As used herein, "genetically engineered antibody gene" encodes genetically engineered antibody, and the genetically engineered antibody includes, but is not limited to natural antibody and recombinant antibody.

As used herein, "genetically engineered antibody gene" encodes genetically engineered antibody, and the genetically engineered antibody includes, but is not limited to human and murine antibody.

As used herein, "genetically engineered antibody gene" encodes genetically engineered antibody, and the genetically engineered antibody includes, but is not limited to therapeutic antibody.

As used herein, "genetically engineered antibody gene" encodes genetically engineered antibody, and the genetically engineered antibody can be single targeting antibody, dual-targeting antibody or multi-targeting antibody.

By "targeting" it is meant an antibody specifically binds to an antigen. By "dual-targeting" it is meant an antibody has two antigen specific binding sites. By "multi-targeting" it is meant an antibody has more than two antigen specific binding sites.

As used herein, "backbone DNA" and "backbone DNA vector" are used interchangeably.

Preferably, the genetically engineered antibody gene expression cassette comprises a promoter operably linked to genetically engineered antibody gene.

More preferably, the promoter is operably linked to genetically engineered antibody gene by at least one of gene sequence of signal peptides and gene sequence of tag.

Still more preferably, the signal peptides are immunoglobulin κ chain signal peptides.

Still more preferably, the tag is at least one of a His tag, GST tag, c-myc tag and Flag tag.

Above signal peptides and tags are preferred in the present invention. The skilled person in the art can select an appropriate signal peptide and label as needed.

As used herein, "genetically engineered antibody gene expression cassette" refers to a gene expression system containing all the necessary elements required for expression of the target polypeptide (genetically engineered antibody in the present invention). The gene expression system normally includes the following elements: promoter, gene sequences encoding polypeptide and terminator. Moreover, coding sequences of signal peptide may be optionally included. These elements are operably linked.

As used herein, "operably linked" refers to a functional arrangement of two or more nucleic acid region or nucleic acid sequences. For example: a promoter region is positioned in certain specific positions with respect to the target nucleic acid sequences, such that the promoter region directs the transcription of the nucleic acid sequences, and the promoter region is "operably linked" to the nucleic acid sequences.

As a preferred form of the forth aspect of the present invention, the present invention provides a method for preparing minicircle DNA having genetically engineered antibody gene expression cassette, wherein the site-specific recombination sites are attB and attP sites, and said genetically engineered antibody gene expression cassette comprises a nucleotide sequence selected from the group consisting of:
  (a) A-a-B-d-e
  (b) A-b-B-d-e
  (c) A -B-c-d -e
  (d) A-a- b-B-c-d-e
  (e) A- a -B-c-d-e
  (f) A- a- b-B -d-e
  (g) A- b -B-c -d-e where A is a nucleotide sequence encoding a promoter, B is a nucleotide sequence encoding genetically engineered antibody; a, b, c, d, e represent base sequence encoding signal peptides, base sequence encoding Flag tag, base sequence encoding His6 tag, stop codon and polyA tailing signal, respectively; "-" represents "operatively linked" between the gene fragments represented by each base sequence.

DNA is deoxyribonucleic acid that consists of four deoxynucleotides (dAMP, dGMP, dCMT and dTMP) connected together by 3,5-phosphodiester bonds. It is understood that "base sequence" is used to represent the nucleotide sequence of genes.

As another preferred form of the forth aspect of the present invention, the present invention provides a method for preparing minicircle DNA having genetically engineered antibody gene expression cassette, comprising:

(1) providing or preparing minicircle DNA recombinant parental plasmid having genetically engineered antibody gene expression cassette, said minicircle DNA recombinant parental plasmid is obtained by inserting a gene sequence of genetically engineered antibody gene expression cassette into multiple cloning sites of a minicircle DNA empty plasmid, and the minicircle DNA empty plasmid is p2ΦC31 plasmid or pMC.BESPX plasmid, and said genetically engineered antibody gene expression cassette comprises a promoter, base sequence encoding immunoglobulin κ chain signal peptide, base sequence encoding Flag tag, genetically engineered antibody genes, base sequence encoding His6 tag, stop codon and polyA tailing signal linked sequentially;

(2) transforming host strains with the minicircle DNA recombinant parental plasmid having genetically engineered antibody gene expression cassette obtained from step (1), non-reversibly producing bacteria plasmid DNA containing attL site and minicircle DNA containing attR site in the presence of ΦC31 recombinase;

(3) cutting the bacteria plasmid DNA containing attL site and obtained from step (2) with I-Sce endonuclease to produce linear DNA fragments; after the plasmid is degraded in host strains, purifying the minicircle DNA containing attR site with normal plasmid purification kits; the minicircle DNA is circular DNA having attR site and genetically engineered antibody gene expression cassette, and the genetically engineered antibody gene expression cassette comprises a promoter, base sequence encoding immunoglobulin κ chain signal peptide, base sequence encoding Flag tag, genetically engineered antibody genes, base sequence encoding His6 tag, stop codon and polyA tailing signal linked sequentially.

Preferably, the genetically engineered antibody genes have base sequence encoding genetically engineered antibody, and the genetically engineered antibody is a dual-targeting specific antibody, and the dual-targeting specific antibody has targeting immune effector cell antigen epitope binding sites and tumor cell antigen epitope binding sites.

More preferably, the immune effector cell is one selected from the group consisting of T lymphocytes, natural killer cells and macrophages.

Further preferably, the tumor cell is one selected from the group consisting of B lymphocytes of tumor cells, leukemia cells, lung cancer cells, gastric cancer cells, colorectal cancer cells, liver cancer cells, esophageal cancer cells, breast cancer cells, pancreatic cancer cells, bladder cancer cells and thyroid cancer cells.

More preferably, the dual-targeting specific antibody combines with at least one antigen epitope of the tumor cells.

Preferably, the promoter comprises cytomegalovirus CMV promoter, RSV promoter, UBC promoter, and EF1α promoter.

More preferably, the promoter is the cytomegalovirus CMV promoter.

Preferably, the polyA tailing signal is bovine growth hormone polynucleotide bpA or SV40.

Further preferably, the polyA tailing signal is bovine growth hormone polynucleotide bpA.

The promoter of the present invention can be a eukaryotic promoter, such as cytomegalovirus CMV, RSV, UBC and EF1α, etc. In the present invention, CMV promoter is more preferred for construction of a minicircle DNA. The present invention constructs minicircle DNA by employing different promoters according to different host cells. The polyA tailing signal of the present invention can be SV40, etc. In the present invention, bpA tailing signal is more preferred for construction of a minicircle DNA. The present invention constructs minicircle DNA by employing different tailing signals according to different host cells.

Preferably, the genetically engineered antibody genes have base sequence encoding bispecific single chain antibody amino acid sequence, and connection form of amino acid sequence of the bispecific single chain antibody is one selected from the group consisting of (a)-(h):

(a) $V_L CD19$-linker1-$V_H CD19$-linker2-$V_L CD3$-linker1-$V_H CD3$,
(b) $V_H CD19$-linker1-$V_L CD19$-linker2-$V_L CD3$-linker1-$V_H CD3$,
(c) $V_L CD19$-linker1-$V_H CD19$-linker2-$V_H CD3$-linker1-$V_L CD3$,
(d) $V_H CD19$-linker1-$V_L CD19$-linker2-$V_H CD3$-linker1-$V_L CD3$,
(e) $V_L CD20$-linker1-$V_H CD20$-linker2-$V_L CD3$-linker1-$V_H CD3$,
(f) $V_H CD20$-linker1-$V_L CD20$-linker2-$V_L CD3$-linker1-$V_H CD3$,
(g) $V_L CD20$-linker1-$V_H CD20$-linker2-$V_H CD3$-linker1-$V_L CD3$,
(h) $V_H CD20$-linker1-$V_L CD20$-linker2-$V_H CD3$-linker1-$V_L CD3$, where amino acid sequence of the $V_L CD19$ is shown in SEQ ID NO: 1; amino acid sequence of the $V_H CD19$ is shown in SEQ ID NO: 2; amino acid sequence of the $V_L CD3$ is one selected from the sequences shown in SEQ ID NO: 3 and SEQ ID NO: 4; amino acid sequence of the $V_H CD3$ is one selected from the sequences shown in SEQ ID NO:5, SEQ ID NO:6 and SEQ ID NO:7; amino acid sequence of the linker1 is one selected from the sequences shown in SEQ ID NO:8, SEQ ID NO:9 and SEQ ID NO:10; amino acid sequence of the linker2 is shown in SEQ ID NO: 11; amino acid sequence of the $V_L CD20$ is shown in SEQ ID NO: 29; amino acid sequence of the $V_H CD20$ is shown in SEQ ID NO: 30.

Preferably, the bispecific single chain antibody amino acid sequence is an amino acid sequence which shows more than 95% identity (preferably ≥98%) to any sequence represented by (a)-(e).

Preferably, the bispecific single chain antibody amino acid sequence is an amino acid sequence which shows more than 95% identity (preferably ≥98%) to any sequence represented by (a)-(e).

Preferably, base sequence of the attR site is shown in SEQ ID NO:28.

More preferably, genetically engineered antibody gene provided in the present invention encodes genetically engineered antibody containing amino acid sequence as follows:

(a) amino acid sequence of $V_L CD19$-linker1-$V_H CD19$-linker2-$V_L CD3$-linker1-$V_H CD3$:
SEQ ID NO:1-SEQ ID NO:9-SEQ ID NO:2-SEQ ID NO:11-SEQ ID NO:4-SEQ ID NO:10-SEQ ID NO:6;

(b) amino acid sequence of $V_H CD19$-linker1-$V_L CD19$-linker2-$V_L CD3$-linker1-$V_H CD3$:
SEQ ID NO:2-SEQ ID NO:10-SEQ ID NO:1-SEQ ID NO:11-SEQ ID NO:3-SEQ ID NO:8-SEQ ID NO:5;

(c) amino acid sequence of $V_L CD19$-linker1-$V_H CD19$-linker2-$V_H CD3$-linker1-$V_L CD3$:
SEQ ID NO:1-SEQ ID NO:10-SEQ ID NO:2-SEQ ID NO:11-SEQ ID NO:5-SEQ ID NO:8-SEQ ID NO:3;

(d) amino acid sequence of $V_H CD19$-linker1-$V_L CD19$-linker2-$V_H CD3$-linker1-$V_L CD3$:
SEQ ID NO:2-SEQ ID NO:8-SEQ ID NO:1-SEQ ID NO:11-SEQ ID NO:7-SEQ ID NO:9-SEQ ID NO:4;

(e) amino acid sequence of $V_H CD20$-linker1-$V_L CD20$-linker2-$V_H CD3$-linker1-$V_L CD3$:
SEQ ID NO: 29-SEQ ID NO:10-SEQ ID NO:30-SEQ ID NO:11-SEQ ID NO:7-SEQ ID NO:9-SEQ ID NO:4;

where the notation "-" represents sequential linking between amino acid sequences.

More preferably, genetically engineered antibody genes of the present invention have the base sequence shown below:

(a') base sequence encoding $V_L CD19$-linker1-$V_H CD19$-linker2-$V_L CD3$-linker1-$V_H CD3$:
SEQ ID NO:12-SEQ ID NO:20-SEQ ID NO:13-SEQ ID NO:22-SEQ ID NO:15-SEQ ID NO:21-SEQ ID NO:17;

(b') base sequence encoding $V_H CD19$-linker1-$V_L CD19$-linker2-$V_L CD3$-linker1-$V_H CD3$:
SEQ ID NO:13-SEQ ID NO:21-SEQ ID NO:12-SEQ ID NO:22-SEQ ID NO:14-SEQ ID NO:19-SEQ ID NO:16;

(c') base sequence encoding $V_L CD19$-linker1-$V_H CD19$-linker2-$V_H CD3$-linker1-$V_L CD3$:
SEQ ID NO:12-SEQ ID NO:21-SEQ ID NO:13-SEQ ID NO:22-SEQ ID NO:16-SEQ ID NO:19-SEQ ID NO:14;

(d') base sequence encoding $V_HCD19$-linker1-$V_LCD19$-linker2-$V_HCD3$-linker1-$V_LCD3$:
SEQ ID NO:13-SEQ ID NO:19-SEQ ID NO:12-SEQ ID NO:22-SEQ ID NO:18-SEQ ID NO:20-SEQ ID NO:15;

(e') base sequence encoding $V_LCD20$-linker1-$V_HCD20$-linker2-$V_HCD3$-linker1-$V_LCD3$:
SEQ ID NO:33-SEQ ID NO:21-SEQ ID NO:34-SEQ ID NO:22-SEQ ID NO:18-SEQ ID NO:20-SEQ ID NO:15;

where the base sequence encoding SEQ ID NO:29 (amino acid sequence of $V_LCD20$) is SEQ ID NO:33; base sequence encoding SEQ ID NO:30 (amino acid sequence of $V_HCD20$) is SEQ ID NO:34.

All the base sequences represented by (a'), (b'), (c'), (d'), (e') and (f') herein are nucleotide sequence of one strand of two single-stranded genes (DNA fragments), and the notation "-" represents sequential linking between base sequences.

It is understood that one of ordinary skill in the art may adjust the base due to the possibility that nucleotide sequences degenerate or mutate. Although the change of base would lead to changes in codon, it would not cause changes in the amino acid translated by the codon. Commonly encountered leucine codons have various codons, such as UUA, UUG, and CUU.

Preferably, the genetically engineered antibody genes is a base sequence which shows more than 95% identity (preferably ≥98%) to any sequence represented by (a')-(e').

Preferably, the genetically engineered antibody genes is a base sequence which shows more than 95% identity (preferably ?98%) to any sequence represented by (a')-(e'). Further, the coding amino acid sequence of the genetically engineered antibody genes is completely or basically identical to coding amino acid sequence of any sequence represented by (a')-(e').

Preferably, the genetically engineered antibody genes are obtained from total gene synthesis or PCR cloning approach.

Preferably, minicircle DNA recombinant parental plasmid having genetically engineered antibody gene expression cassette of the present invention has the genes encoding bispecific single chain antibody, wherein the bispecific single chain antibody has four different domains, namely variable domain of the light chain of binding to human CD19 antigens ($V_LCD19$), variable domain of the heavy chain of binding to human CD19 antigens ($V_HCD19$), variable domain of the light chain of binding to human CD3 antigens ($V_LCD3$), variable domain of the heavy chain of binding to human CD3 antigens ($V_HCD3$). Coding genes of $V_LCD19$, $V_HCD19$, $V_LCD3$ and $V_HCD3$ polypeptide is obtained by screening antibody library, wherein $V_LCD19$ and $V_HCD19$ constitutes functional domain binding to human CD19 antigens, $V_LCD3$ and $V_HCD3$ constitutes functional domain binding to human CD3 antigens, therefore the genetically engineered antibody of the present invention is preferably an anti-CD19×CD3 bispecific single chain antibody (i.e., anti-CD19×CD3 BiTE);

Preferably, preferred structure forms of the anti-CD19×CD3 bispecific single chain antibody are:
$V_LCD19$-linker1-$V_HCD19$-linker2-$V_HCD3$-linker1-$V_LCD3$, where Linker is a linker peptide employing polypeptide sequence that is mainly constituted by glycine and serine. Glycine is the smallest amino acid, and it can increase flexibility of side chain due to its minimal side chain. As the most hydrophilic amino acid, serine could increase hydrophilicity of peptide chain.

Secondly, the genetically engineered antibody gene expression cassette of the present invention has base sequence encoding immunoglobulin κ chain signal peptides and base sequence encoding Flag tag, which makes it possible to add immunoglobulin light κ chain secretion signal peptides and Flag tag at the N-terminal of the genetically engineered antibody. It ensures that antibody is expressed and secreted outside the host cell. In addition, a His6 tag connects the genetically engineered antibody at C-terminal, which is of benefit to purifying antibody by nickel column affinity chromatography.

The anti-CD20×CD3 bispecific single chain antibody (i.e. CD20×CD3 BiTE) has four different domains, namely variable domain of the light chain of binding to human CD20 antigens ($V_LCD20$), variable domain of the heavy chain of binding to human CD20 antigens ($V_HCD20$), variable domain of the light chain of binding to human CD3 antigens ($V_LCD3$), variable domain of the heavy chain of binding to human CD3 antigens ($V_LCD20$).

It is understood that base sequences described herein represent the nucleotide sequence of the gene.

Preferably, the recombinase is ΦC31 recombinase.
Preferably, the host strains are Top10.
Preferably, the host strains are ZYCY10P3S2T engineered bacteria.

Preferably, the process of the site-specific recombination event of the minicircle DNA recombinant parental plasmid having genetically engineered antibody gene expression cassette occurs in host strains and comprises: recombinant expression vector having genetically engineered antibody gene expression cassette contains attB and attP sites that can be recombinated in the presence of ΦC31 recombinase, making minicircle parental plasmid non-reversibly produce bacteria plasmid DNA containing attL site and minicircle DNA containing attR site. The minicircle DNA containing attR site is devoid of sequence of pronucleus plasmid and free from chromosomal DNA of human and mammalian cells, providing stable and persistent expression of genetically engineered antibody. The bacteria plasmid DNA containing attL site is cut with I-Sce endonuclease to produce linear DNA, and the plasmid is degraded in host strains.

The present invention further provides a method for administrating the minicircle DNA having genetically engineered antibody gene expression cassette of the third aspect or the method for preparing a minicircle DNA having genetically engineered antibody gene expression cassette of the forth aspect, wherein the method is one selected from (1)-(4):

(1) administrating the minicircle DNA alone;
(2) administrating the minicircle DNA in combination with one of chemotherapy, radiotherapy, surgery, biotherapy and immunotherapy, or with their combinations.
(3) delivering the minicircle DNA into a patient for therapy by a targeted delivery approach;
(4) transfecting immune effector cell with the minicircle DNA by an in vitro transfection technique, and then transporting the immune effector cell transfected with the minicircle DNA into a patient for therapy.

Preferably, in method (4), the immune effector cell is one selected from the group consisting of T lymphocytes, natural killer cells, macrophages and stem cells.

In method (4), the immune effector cell is CIK cell or D-CIK cell.

The minicircle DNA containing attR site is devoid of sequence of pronucleus plasmid and free from chromosomal DNA of human and mammalian cells, providing stable and persistent expression of genetically engineered antibody.

The minicircle DNA can be used alone for targeted therapy, such as delivery to a patient for expression of genetically engineered antibody, leading T cell to specifically kill tumor cell.

The minicircle DNA of the present invention can be used for transfecting immune effector cell of a patient in vitro, and then the immune effector cell transfected with the minicircle DNA is transported into the patient for therapy.

The minicircle DNA of the present invention can be used for therapy in combination with chemotherapy, radiotherapy, surgery, biotherapy and immunotherapy.

In a fifth aspect, the present invention provides a host comprising the minicircle DNA as described in the third aspect or forth aspect.

Preferably, the host is human or mammal.

Preferably, the host is human or mammalian cell.

More preferably, the mammalian cell is CHO cell.

In a sixth aspect, the present invention provides a genetically engineered antibody which is a dual-targeting specific antibody, and the dual-targeting specific antibody has targeting immune effector cell antigen epitope binding sites and tumor cell antigen epitope binding sites.

As used herein, "genetically engineered antibody" includes, but is not limited to natural antibody and recombinant antibody.

As used herein, "genetically engineered antibody" includes, but is not limited to human and murine antibody.

As used herein, "genetically engineered antibody gene" includes, but is not limited to therapeutic antibody.

As used herein, "genetically engineered antibody gene" can be single targeting antibody, dual-targeting antibody or multi-targeting antibody.

By "targeting" it is meant an antibody specifically binds to an antigen. By "dual-targeting" it is meant an antibody has two antigen specific binding sites. By "multi-targeting" it is meant an antibody has more than two antigen specific binding sites.

Preferably, the immune effector cell is one selected from the group consisting of T lymphocytes, natural killer cells and macrophages.

Preferably, the tumor cell is one selected from the group consisting of B lymphocytes of tumor cells, leukemia cells, lung cancer cells, gastric cancer cells, colorectal cancer cells, liver cancer cells, esophageal cancer cells, breast cancer cells, pancreatic cancer cells, bladder cancer cells and thyroid cancer cells.

Preferably, the dual-targeting specific antibody combines with at least one antigen epitope of the tumor cells.

Preferably, the genetically engineered antibody is a bispecific single chain antibody, and connection form of amino acid sequence of the bispecific single chain antibody is one selected from the group consisting of (a)-(h):

(a) $V_L$CD19-linker1-$V_H$CD19-linker2-$V_L$CD3-linker1-$V_H$CD3, (b) $V_H$CD19-linker1-$V_L$CD19-linker2-$V_L$CD3-linker1-$V_H$CD3, (c) $V_L$CD19-linker1-$V_H$CD19-linker2-$V_H$CD3-linker1-$V_L$CD3, (d) $V_H$CD19-linker1-$V_L$CD19-linker2-$V_H$CD3-linker1-$V_L$CD3, (e) $V_L$CD20-linker1-$V_H$CD20-linker2-$V_L$CD3-linker1-$V_H$CD3, (f) $V_H$CD20-linker1-$V_L$CD20-linker2-$V_L$CD3-linker1-$V_H$CD3, (g) $V_L$CD20-linker1-$V_H$CD20-linker2-$V_H$CD3-linker1-$V_L$CD3, (h) $V_H$CD20-linker1-$V_L$CD20-linker2-$V_H$CD3-linker1-$V_L$CD3, where amino acid sequence of the $V_L$CD19 is shown in SEQ ID NO: 1; amino acid sequence of the $V_H$CD19 is shown in SEQ ID NO: 2; amino acid sequence of the $V_L$CD3 is one selected from the sequences shown in SEQ ID NO: 3 and SEQ ID NO: 4; amino acid sequence of the $V_H$CD3 is one selected from the sequences shown in SEQ ID NO:5, SEQ ID NO:6 and SEQ ID NO:7; amino acid sequence of the linker1 is one selected from the sequences shown in SEQ ID NO:8, SEQ ID NO:9 and SEQ ID NO:10; amino acid sequence of the linker2 is shown in SEQ ID NO: 11; amino acid sequence of the $V_L$CD20 is shown in SEQ ID NO: 29; amino acid sequence of the $V_H$CD20 is shown in SEQ ID NO: 30.

Preferably, the bispecific single chain antibody amino acid sequence is an amino acid sequence which shows more than 95% identity (preferably ≥98%) to any sequence represented by (a)-(e).

More preferably, genetically engineered antibody gene provided in the present invention has amino acid sequence as follows:

(a) amino acid sequence of $V_L$CD19-linker1-$V_H$CD19-linker2-$V_L$CD3-linker1-$V_H$CD3:
SEQ ID NO:1-SEQ ID NO:9-SEQ ID NO:2-SEQ ID NO:11-SEQ ID NO:4-SEQ ID NO:10-SEQ ID NO:6;

(b) amino acid sequence of $V_H$CD19-linker1-$V_L$CD19-linker2-$V_L$CD3-linker1-$V_H$CD3:
SEQ ID NO:2-SEQ ID NO:10-SEQ ID NO:1-SEQ ID NO:11-SEQ ID NO:3-SEQ ID NO:8-SEQ ID NO:5;

(c) amino acid sequence of $V_L$CD19-linker1-$V_H$CD19-linker2-$V_H$CD3-linker1-$V_L$CD3:
SEQ ID NO:1-SEQ ID NO:10-SEQ ID NO:2-SEQ ID NO:11-SEQ ID NO:5-SEQ ID NO:8-SEQ ID NO:3;

(d) amino acid sequence of $V_H$CD19-linker1-$V_L$CD19-linker2-$V_H$CD3-linker1-$V_L$CD3:
SEQ ID NO:2-SEQ ID NO:8-SEQ ID NO:1-SEQ ID NO:11-SEQ ID NO:7-SEQ ID NO:9-SEQ ID NO:4;

(e) amino acid sequence of $V_H$CD20-linker1-$V_L$CD20-linker2-$V_H$CD3-linker1-$V_L$CD3:
SEQ ID NO: 29-SEQ ID NO:10-SEQ ID NO:30-SEQ ID NO:11-SEQ ID NO:7-SEQ ID NO:9-SEQ ID NO:4;

where the notation "-" represents sequential linking between amino acid sequences.

More preferably, genetically engineered antibody genes of the present invention have the base sequence shown below:

(a') base sequence encoding $V_L$CD19-linker1-$V_H$CD19-linker2-$V_L$CD3-linker1-$V_H$CD3:
SEQ ID NO:12-SEQ ID NO:20-SEQ ID NO:13-SEQ ID NO:22-SEQ ID NO:15-SEQ ID NO:21-SEQ ID NO:17;

(b') base sequence encoding $V_H$CD19-linker1-$V_L$CD19-linker2-$V_L$CD3-linker1-$V_H$CD3:
SEQ ID NO:13-SEQ ID NO:21-SEQ ID NO:12-SEQ ID NO:22-SEQ ID NO:14-SEQ ID NO:19-SEQ ID NO:16;

(c') base sequence encoding $V_L$CD19-linker1-$V_H$CD19-linker2-$V_H$CD3-linker1-$V_L$CD3:
SEQ ID NO:12-SEQ ID NO:21-SEQ ID NO:13-SEQ ID NO:22-SEQ ID NO:16-SEQ ID NO:19-SEQ ID NO:14;

(d') base sequence encoding $V_H$CD19-linker1-$V_L$CD19-linker2-$V_H$CD3-linker1-$V_L$CD3:
SEQ ID NO:13-SEQ ID NO:19-SEQ ID NO:12-SEQ ID NO:22-SEQ ID NO:18-SEQ ID NO:20-SEQ ID NO:15;

(e') base sequence encoding $V_LCD20$-linker1-$V_HCD20$-linker2-$V_HCD3$-linker1-$V_LCD3$:

SEQ ID NO:33-SEQ ID NO:21-SEQ ID NO:34-SEQ ID NO:22-SEQ ID NO:18-SEQ ID NO:20-SEQ ID NO:15;

where the base sequence encoding SEQ ID NO:29 (amino acid sequence of $V_LCD20$) is SEQ ID NO:33; base sequence encoding SEQ ID NO:30 (amino acid sequence of $V_HCD20$) is SEQ ID NO:34.

All the base sequences represented by (a'), (b'), (c'), (d'), (e') and (f') herein are nucleotide sequence of one strand of two single-stranded genes (DNA fragments), and the notation "-" represents sequential linking between base sequences.

It is understood that one of ordinary skill in the art may adjust the base due to the possibility that nucleotide sequences degenerate or mutate. Although the change of base would lead to changes in codon, it would not cause changes in the amino acid translated by the codon. Commonly encountered leucine codons have various codons, such as UUA, UUG, and CUU.

Preferably, the genetically engineered antibody genes is a base sequence which shows more than 95% identity (preferably ?98%) to any sequence represented by (a')-(e').

Preferably, the genetically engineered antibody genes is a base sequence which shows more than 95% identity (preferably ?98%) to any sequence represented by (a')-(e'). Further, the coding amino acid sequence of the genetically engineered antibody genes is completely or basically identical to coding amino acid sequence of any sequence represented by (a')-(e').

Preferably, the genetically engineered antibody genes are obtained from total gene synthesis or PCR cloning approach.

Preferably, minicircle DNA recombinant parental plasmid having genetically engineered antibody gene expression cassette of the present invention has the genes encoding bispecific single chain antibody, wherein the bispecific single chain antibody has four different domains, namely variable domain of the light chain of binding to human CD19 antigens ($V_LCD19$), variable domain of the heavy chain of binding to human CD19 antigens ($V_HCD19$), variable domain of the light chain of binding to human CD3 antigens ($V_LCD3$), variable domain of the heavy chain of binding to human CD3 antigens ($V_HCD3$). Coding genes of $V_LCD19$, $V_HCD19$, $V_LCD3$ and $V_HCD3$ polypeptide is obtained by screening antibody library, wherein $V_LCD19$ and $V_HCD19$ constitutes functional domain binding to human CD19 antigens, $V_LCD3$ and $V_HCD3$ constitutes functional domain binding to human CD3 antigens, therefore the genetically engineered antibody of the present invention is preferably an anti-CD19×CD3 bispecific single chain antibody (i.e., anti-CD19×CD3 BiTE);

Preferably, preferred structure forms of the anti-CD19×CD3 bispecific single chain antibody are:

$V_LCD19$-linker1-$V_HCD19$-linker2-$V_HCD3$-linker1-$V_LCD3$, where Linker is a linker peptide employing polypeptide sequence that is mainly constituted by glycine and serine. Glycine is the smallest amino acid, and it can increase flexibility of side chain due to its minimal side chain. As the most hydrophilic amino acid, serine could increase hydrophilicity of peptide chain.

Secondly, the genetically engineered antibody gene expression cassette of the present invention has base sequence encoding immunoglobulin κ chain signal peptides and base sequence encoding Flag tag, which makes it possible to add immunoglobulin light κ chain secretion signal peptides and Flag tag at the N-terminal of the genetically engineered antibody. It ensures that antibody is expressed and secreted outside the host cell. In addition, a His6 tag connects the genetically engineered antibody at C-terminal, which is of benefit to purifying antibody by nickel column affinity chromatography.

The anti-CD20×CD3 bispecific single chain antibody (i.e. CD20×CD3 BiTE) has four different domains, namely variable domain of the light chain of binding to human CD20 antigens ($V_LCD20$), variable domain of the heavy chain of binding to human CD20 antigens ($V_HCD20$), variable domain of the light chain of binding to human CD3 antigens ($V_LCD3$), variable domain of the heavy chain of binding to human CD3 antigens ($V_LCD20$).

It is understood that base sequences described herein represent the nucleotide sequence of the gene.

In a seventh aspect, the present invention provides a method for preparing genetically engineered antibody, comprising:

(1) providing or preparing minicircle DNA, the minicircle DNA is circular DNA having genetically engineered antibody gene expression cassette, and the genetically engineered antibody gene expression cassette comprises genetically engineered antibody gene;

(2) transfecting host cell with the minicircle DNA having genetically engineered antibody gene expression cassette obtained from step (1), expressing and producing genetically engineered antibody in the host cell.

As used herein, "minicircle DNA" refers to a vector that exists mainly in a superhelical structure and is devoid of prokaryotic plasmid backbone DNA sequences. The minicircle DNA, which is free from chromosomal DNA of human and mammalian cells, could provide stable and persistent expression of transcription or target genes.

As used herein, the terms "minicircle DNA" and "minicircle DNA vector" are used interchangeably.

Compared with viral vectors and plasmid vectors, minicircle DNA reduce the possibility of occurrence of inflammation and silencing of gene expression in vitro or in vivo due to the removal of backbone DNA sequences derived from bacterial, thus providing a more long-term and stronger expression. In addition, clinical safety is improved for the lack of bacterial sequences including resistance marker genes and replication origin in minicircle DNA.

In a preferred embodiment, the minicircle DNA is produced from minicircle DNA recombinant parental plasmid through a site-specific recombination of site-specific recombination sites.

As used herein, the minicircle DNA recombinant parental plasmid is obtained by inserting a gene sequence of genetically engineered antibody gene expression cassette into multiple cloning sites of a minicircle DNA empty plasmid, and said genetically engineered antibody gene expression cassette comprises genetically engineered antibody gene.

As used herein, "minicircle DNA empty plasmid" refers to a plasmid vector having site-specific recombination sites.

As used herein, "plasmid vector" in genetically engineered research refers to a DNA structure possible to insert exogenous DNA and capable of replicating in a recipient cell.

As used herein, the terms "plasmid" and "plasmid vector" are used interchangeably.

As used herein, "minicircle DNA recombinant parental plasmid" has site-specific recombination sites, and "minicircle DNA recombinant parental plasmid" refers to a recombinant parental plasmid that can produce minicircle DNA and backbone DNA through a site-specific recombination of site-specific recombination sites.

As used herein, the terms "minicircle DNA recombinant parental plasmid" and "minicircle DNA parental plasmid" are used interchangeably.

As used herein, "backbone DNA sequences" have DNA sequences functioning replication of bacterial plasmid in a standard plasmid or screening for host containing plasmid. Such DNA sequences include bacterial replication sequences, resistance genes, unmethylated CpG gene sequences, etc.

As used herein the terms "backbone DNA" and "backbone DNA vector" are used interchangeably.

In a preferred embodiment, minicircle DNA parental plasmid is transformed into a host cell, after the induction, the minicircle DNA parental plasmid produces minicircle DNA and backbone DNA through site-specific recombination event of site-specific recombination sites.

Preferably, the host cell is E. coli.

Preferably, the site-specific recombination sites are phiC31 site-specific recombination sites, parA site-specific recombination sites or Cre site-specific recombination sites.

As used herein, "site-specific recombination" preferably employs the phiC31 (ΦC31) recombinase system, parA recombinase system or Cre recombinase system reported by Hu Chunsheng, etc. in "Letters in Biotechnology (22 (1): 104-109 (2011))".

Preferably, the backbone DNA contains at least one DNA endonuclease site.

Further preferably, the DNA endonuclease is I-SceI endonuclease.

Under such preferred conditions, the backbone DNA is able to be cut and degraded by DNA endonuclease in the host cell, thereby facilitating purification of minicircle DNA. Furthermore, the unrecombined minicircle DNA parental plasmid is also able to be cut and degraded by DNA endonuclease in the host cell because it likewise has DNA endonuclease sites.

In another preferred embodiment, phiC31 recombinase is employed to prepare minicircle DNA, wherein site-specific recombination sites of the minicircle DNA empty plasmid are attB and attP sites. Preferred attB and attP sites are minimal recognition sequences that can be recognized by phiC31 recombinase (attB, attP minimal recognition sequences are shown as SEQ ID NO: 31 and SEQ ID NO: 32).

In yet another preferred embodiment, minicircle DNA parental plasmid constructed herein has attB and attP sites, and the attB and attP sites are presented between the nucleotide sequences of backbone DNA and minicircle DNA.

In particular, the attB and attP sites can be recombinated in the presence of ΦC31 recombinase, making minicircle parental plasmid non-reversibly produce plasmid backbone DNA containing attL site and minicircle DNA containing attR site.

The skilled person in the art can select an appropriate recombinase system as needed, and select appropriate host strains capable of expressing corresponding recombinase, and construct minicircle DNA empty vector that has corresponding site-specific recombination sites.

Preferably, the ΦC31 recombinase expression cassette may be located on minicircle DNA empty plasmid or minicircle DNA recombinant parental plasmid, expressed by minicircle DNA recombinant parental plasmid during the minicircle DNA preparation.

Preferably, the ΦC31 recombinase expression cassette may be located in the host cell genes and expressed by the host cell.

Preferably, the minicircle DNA empty plasmid is p2ΦC31 plasmid or pMC.BESPX plasmid.

As used herein, "p2ΦC31 empty plasmid" has attB and attP sites that can be recombinated in the presence of ΦC31 recombinase.

In particular, methods for constructing empty plasmid p2ΦC31 can be found in Chen Z Y et al., Molecular Therapy, 8 (3), 495-500 (2003); Chen Z Y, et al., Human Gene Therapy, 16 (1), 126-131 (2005) and U.S. Pat. No. 7,897,380 B2.

As used herein, "pMC.BESPX empty plasmid" has attB and attP sites that can be recombinated in the presence of ΦC31 recombinase.

In particular, methods for constructing empty plasmid pMC.BESPX and complete genome sequence can be found in Chen Z Y et al., Nature Biotechnology, 28, (12), 1289-1291 (2010).

The p2ΦC31 plasmid and pMC.BESPX plasmid employed in the preferred embodiments of the present invention differ in that: p2ΦC31 vector has nucleotide sequence encoding ΦC31 recombinase and I-SceI endonuclease, while pMC.BESPX vector has no nucleotide sequence encoding ΦC31 recombinase and I-SceI endonuclease, such that minicircle DNA parental plasmids prepared by employing pMC.BESPX vector have better quality and reduce contaminations of nucleotide sequence of recombinase and endonuclease. However, pMC.BESPX vector should be used with the E. coli ZYCY10P3S2T engineered bacteria having function to encode ΦC31 recombinase and I-SceI endonuclease. The pMC.BESPX without nucleotide sequence encoding ΦC31 recombinase (i.e. phiC31 recombinase) and I-SceI endonuclease should be used with ZYCY10P3S2T engineered bacteria to generate in vivo site-specific recombination (E. coli TOP 10 has no such function) and ultimately produce a minicircle DNA. Accordingly, the p2ΦC31 vector should be used with TOP 10 to generate site-specific recombination in TOP10, and ultimately produce a minicircle DNA.

As used herein, "genetically engineered antibody" includes, but is not limited to natural antibody and recombinant antibody.

As used herein, "genetically engineered antibody" includes, but is not limited to human and murine antibody.

As used herein, "genetically engineered antibody gene" includes, but is not limited to therapeutic antibody.

As used herein, "genetically engineered antibody gene" can be single targeting antibody, dual-targeting antibody or multi-targeting antibody.

By "targeting" it is meant an antibody specifically binds to an antigen. By "dual-targeting" it is meant an antibody has two antigen specific binding sites. By "multi-targeting" it is meant an antibody has more than two antigen specific binding sites.

As used herein the terms "backbone DNA" and "backbone DNA vector" are used interchangeably.

Preferably, the genetically engineered antibody gene expression cassette comprises a promoter operably linked to genetically engineered antibody gene.

More preferably, the promoter is operably linked to genetically engineered antibody gene by at least one of gene sequence of signal peptides and gene sequence of tag.

Still more preferably, the signal peptides are immunoglobulin κ chain signal peptides.

Still more preferably, the tag is at least one of a His tag, GST tag, c-myc tag and Flag tag.

Above signal peptides and tags are preferred in the present invention. The skilled person in the art can select an appropriate signal peptide and label as needed.

As used herein, "genetically engineered antibody gene expression cassette" refers to a gene expression system containing all the necessary elements required for expression of the target polypeptide (genetically engineered antibody in the present invention). The gene expression system normally includes the following elements: promoter, gene sequences encoding polypeptide and terminator. Moreover, coding sequences of signal peptide may be optionally included. These elements are operably linked.

As used herein, "operably linked" refers to a functional arrangement of two or more nucleic acid region or nucleic acid sequences. For example: a promoter region is positioned in certain specific positions with respect to the target nucleic acid sequences, such that the promoter region directs the transcription of the nucleic acid sequences, and the promoter region is "operably linked" to the nucleic acid sequences.

As a preferred form of the seventh aspect of the present invention, the present invention provides a method for preparing genetically engineered antibody, comprising:

(1) providing or preparing minicircle DNA, the minicircle DNA is circular DNA having attR site and genetically engineered antibody gene expression cassette, and said gene expression cassette comprises a nucleotide sequence selected from the group consisting of:

(a) A-a-B-d-e
(b) A-b-B-d-e
(c) A -B-c-d -e
(d) A-a- b-B-c-d-e
(e) A- a -B-c-d-e
(f) A- a- b-B -d-e
(g) A- b -B-c -d-e where A is a nucleotide sequence encoding a promoter, B is a nucleotide sequence encoding genetically engineered antibody; a, b, c, d, e represent base sequence encoding signal peptides, base sequence encoding Flag tag, base sequence encoding His6 tag, stop codon and polyA tailing signal, respectively; "-" represents "operatively linked" between the gene fragments represented by each base sequence;

(2) transfecting host cell with the minicircle DNA having genetically engineered antibody gene expression cassette obtained from step (1), expressing and producing genetically engineered antibody in the host cell.

DNA is deoxyribonucleic acid that consists of four deoxynucleotides (dAMP, dGMP, dCMT and dTMP) connected together by 3,5-phosphodiester bonds. It is understood that "base sequence" is used to represent the nucleotide sequence of genes.

As another preferred form of the seventh aspect of the present invention, the present invention provides a method for preparing genetically engineered antibody, comprising:

(1) providing or preparing minicircle DNA having genetically engineered antibody gene expression cassette, and the minicircle DNA is circular DNA having attR site and genetically engineered antibody gene expression cassette, and the genetically engineered antibody gene expression cassette comprises a promoter, base sequence encoding immunoglobulin κ chain signal peptide, base sequence encoding Flag tag, genetically engineered antibody genes, base sequence encoding His6 tag, stop codon and polyA tailing signal linked sequentially;

(2) transfecting host cell with the minicircle DNA having genetically engineered antibody gene expression cassette obtained from step (1), expressing and producing genetically engineered antibody in the host cell.

Preferably, the genetically engineered antibody genes have base sequence encoding genetically engineered antibody, and the genetically engineered antibody is a dual-targeting specific antibody, and the dual-targeting specific antibody has targeting immune effector cell antigen epitope binding sites and tumor cell antigen epitope binding sites.

More preferably, the immune effector cell is one selected from the group consisting of T lymphocytes, natural killer cells and macrophages.

Further preferably, the tumor cell is one selected from the group consisting of B lymphocytes of tumor cells, leukemia cells, lung cancer cells, gastric cancer cells, colorectal cancer cells, liver cancer cells, esophageal cancer cells, breast cancer cells, pancreatic cancer cells, bladder cancer cells and thyroid cancer cells.

More preferably, the dual-targeting specific antibody combines with at least one antigen epitope of the tumor cells.

Preferably, the genetically engineered antibody is a bispecific single chain antibody, and connection form of amino acid sequence of the bispecific single chain antibody is one selected from the group consisting of (a)-(h):

(a) $V_L$CD19-linker1-$V_H$CD19-linker2-$V_L$CD3-linker1-$V_H$CD3,
(b) $V_H$CD19-linker1-$V_L$CD19-linker2-$V_L$CD3-linker1-$V_H$CD3,
(c) $V_L$CD19-linker1-$V_H$CD19-linker2-$V_H$CD3-linker1-$V_L$CD3,
(d) $V_H$CD19-linker1-$V_L$CD19-linker2-$V_H$CD3-linker1-$V_L$CD3,
(e) $V_L$CD20-linker1-$V_H$CD20-linker2-$V_L$CD3-linker1-$V_H$CD3,
(f) $V_H$CD20-linker1-$V_L$CD20-linker2-$V_L$CD3-linker1-$V_H$CD3,
(g) $V_L$CD20-linker1-$V_H$CD20-linker2-$V_H$CD3-linker1-$V_L$CD3,
(h) $V_H$CD20-linker1-$V_L$CD20-linker2-$V_H$CD3-linker1-$V_L$CD3, where amino acid sequence of the $V_L$CD19 is shown in SEQ ID NO: 1; amino acid sequence of the $V_H$CD19 is shown in SEQ ID NO: 2; amino acid sequence of the $V_L$CD3 is one selected from the sequences shown in SEQ ID NO: 3 and SEQ ID NO: 4; amino acid sequence of the $V_H$CD3 is one selected from the sequences shown in SEQ ID NO:5, SEQ ID NO:6 and SEQ ID NO:7; amino acid sequence of the linker1 is one selected from the sequences shown in SEQ ID NO:8, SEQ ID NO:9 and SEQ ID NO:10; amino acid sequence of the linker2 is shown in SEQ ID NO: 11.

Preferably, the bispecific single chain antibody amino acid sequence is an amino acid sequence which shows more than 95% identity (preferably ?98%) to any sequence represented by (a)-(e).

Preferably, the minicircle DNA having genetically engineered antibody gene expression cassette is produced from minicircle DNA recombinant parental plasmid through a site-specific recombination in host strains.

Preferably, base sequence of the attR site is shown in SEQ ID NO:28.

More preferably, genetically engineered antibody gene provided in the present invention has amino acid sequence as follows:

(a) amino acid sequence of $V_L$CD19-linker1-$V_H$CD19-linker2-$V_L$CD3-linker1-$V_H$CD3:
SEQ ID NO:1-SEQ ID NO:9-SEQ ID NO:2-SEQ ID NO:11-SEQ ID NO:4-SEQ ID NO:10-SEQ ID NO:6;

(b) amino acid sequence of V_HCD19-linker1-V_LCD19-linker2-V_LCD3-linker1-V_HCD3:
SEQ ID NO:2-SEQ ID NO:10-SEQ ID NO:1-SEQ ID NO:11-SEQ ID NO:3-SEQ ID NO:8-SEQ ID NO:5;
(c) amino acid sequence of V_LCD19-linker1-V_HCD19-linker2-V_HCD3-linker1-V_LCD3:
SEQ ID NO:1-SEQ ID NO:10-SEQ ID NO:2-SEQ ID NO:11-SEQ ID NO:5-SEQ ID NO:8-SEQ ID NO:3;
(d) amino acid sequence of V_HCD19-linker1-V_LCD19-linker2-V_HCD3-linker1-V_LCD3:
SEQ ID NO:2-SEQ ID NO:8-SEQ ID NO:1-SEQ ID NO:11-SEQ ID NO:7-SEQ ID NO:9-SEQ ID NO:4;
(e) amino acid sequence of V_HCD20-linker1-V_LCD20-linker2-V_HCD3-linker1-V_LCD3:
SEQ ID NO: 29-SEQ ID NO:10-SEQ ID NO:30-SEQ ID NO:11-SEQ ID NO:7-SEQ ID NO:9-SEQ ID NO:4;
where the notation "-" represents sequential linking between amino acid sequences.

More preferably, genetically engineered antibody genes of the present invention have the base sequence shown below:
(a') base sequence encoding V_LCD19-linker1-V_HCD19-linker2-V_LCD3-linker1-V_HCD3:
SEQ ID NO:12-SEQ ID NO:20-SEQ ID NO:13-SEQ ID NO:22-SEQ ID NO:15-SEQ ID NO:21-SEQ ID NO:17;
(b') base sequence encoding V_HCD19-linker1-V_LCD19-linker2-V_LCD3-linker1-V_HCD3:
SEQ ID NO:13-SEQ ID NO:21-SEQ ID NO:12-SEQ ID NO:22-SEQ ID NO:14-SEQ ID NO:19-SEQ ID NO:16;
(c') base sequence encoding V_LCD19-linker1-V_HCD19-linker2-V_HCD3-linker1-V_LCD3:
SEQ ID NO:12-SEQ ID NO:21-SEQ ID NO:13-SEQ ID NO:22-SEQ ID NO:16-SEQ ID NO:19-SEQ ID NO:14;
(d') base sequence encoding V_HCD19-linker1-V_LCD19-linker2-V_HCD3-linker1-V_LCD3:
SEQ ID NO:13-SEQ ID NO:19-SEQ ID NO:12-SEQ ID NO:22-SEQ ID NO:18-SEQ ID NO:20-SEQ ID NO:15;
(e') base sequence encoding V_LCD20-linker1-V_HCD20-linker2-V_HCD3-linker1-V_LCD3:
SEQ ID NO:33-SEQ ID NO:21-SEQ ID NO:34-SEQ ID NO:22-SEQ ID NO:18-SEQ ID NO:20-SEQ ID NO:15;
where the base sequence encoding SEQ ID NO:29 (amino acid sequence of V_LCD20) is SEQ ID NO:33; base sequence encoding SEQ ID NO:30 (amino acid sequence of V_HCD20) is SEQ ID NO:34.

All the base sequences represented by (a'), (b'), (c'), (d'), (e') and (f') herein are nucleotide sequence of one strand of two single-stranded genes (DNA fragments), and the notation "-" represents sequential linking between base sequences.

It is understood that one of ordinary skill in the art may adjust the base due to the possibility that nucleotide sequences degenerate or mutate. Although the change of base would lead to changes in codon, it would not cause changes in the amino acid translated by the codon. Commonly encountered leucine codons have various codons, such as UUA, UUG, and CUU.

Preferably, the genetically engineered antibody genes is a base sequence which shows more than 95% identity (preferably ?98%) to any sequence represented by (a')-(e').

Preferably, the genetically engineered antibody genes is a base sequence which shows more than 95% identity (preferably ?98%) to any sequence represented by (a')-(e'). Further, the coding amino acid sequence of the genetically engineered antibody genes is completely or basically identical to coding amino acid sequence of any sequence represented by (a')-(e').

Preferably, the genetically engineered antibody genes are obtained from total gene synthesis or PCR cloning approach.

Preferably, minicircle DNA recombinant parental plasmid having genetically engineered antibody gene expression cassette of the present invention has the genes encoding bispecific single chain antibody, wherein the bispecific single chain antibody has four different domains, namely variable domain of the light chain of binding to human CD19 antigens (V_LCD19), variable domain of the heavy chain of binding to human CD19 antigens (V_HCD19), variable domain of the light chain of binding to human CD3 antigens (V_LCD3), variable domain of the heavy chain of binding to human CD3 antigens (V_HCD3). Coding genes of V_LCD19, V_HCD19, V_LCD3 and V_HCD3 polypeptide is obtained by screening antibody library, wherein V_LCD19 and V_HCD19 constitutes functional domain binding to human CD19 antigens, V_LCD3 and V_HCD3 constitutes functional domain binding to human CD3 antigens, therefore the genetically engineered antibody of the present invention is preferably an anti-CD19×CD3 bispecific single chain antibody (i.e., anti-CD19×CD3 BiTE);

Preferably, preferred structure forms of the anti-CD19× CD3 bispecific single chain antibody are:
V_LCD19-linker1-V_HCD19-linker2-V_HCD3-linker1-V_LCD3, where Linker is a linker peptide employing polypeptide sequence that is mainly constituted by glycine and serine. Glycine is the smallest amino acid, and it can increase flexibility of side chain due to its minimal side chain. As the most hydrophilic amino acid, serine could increase hydrophilicity of peptide chain.

Secondly, the genetically engineered antibody gene expression cassette of the present invention has base sequence encoding immunoglobulin κ chain signal peptides and base sequence encoding Flag tag, which makes it possible to add immunoglobulin light κ chain secretion signal peptides and Flag tag at the N-terminal of the genetically engineered antibody. It ensures that antibody is expressed and secreted outside the host cell. In addition, a His6 tag connects the genetically engineered antibody at C-terminal, which is of benefit to purifying antibody by nickel column affinity chromatography.

The anti-CD20×CD3 bispecific single chain antibody (i.e. CD20×CD3 BiTE) has four different domains, namely variable domain of the light chain of binding to human CD20 antigens (V_LCD20), variable domain of the heavy chain of binding to human CD20 antigens (V_HCD20), variable domain of the light chain of binding to human CD3 antigens (V_LCD3), variable domain of the heavy chain of binding to human CD3 antigens (V_LCD3).

It is understood that base sequences described herein represent the nucleotide sequence of the gene.

Preferably, the promoter comprises cytomegalovirus CMV promoter, RSV promoter, UBC promoter, and EF1α promoter.

More preferably, the promoter is the cytomegalovirus CMV promoter.

Preferably, the polyA tailing signal is bovine growth hormone polynucleotide bpA or SV40.

Further preferably, the polyA tailing signal is bovine growth hormone polynucleotide bpA.

The promoter of the present invention can be a eukaryotic promoter, such as cytomegalovirus CMV, RSV, UBC and EF1α, etc. In the present invention, CMV promoter is more preferred for construction of a minicircle DNA. The present invention constructs minicircle DNA by employing different promoters according to different host cells. The polyA tailing signal of the present invention can be SV40, etc. In the present invention, bpA tailing signal is more preferred for construction of a minicircle DNA. The present invention constructs minicircle DNA by employing different tailing signals according to different host cells.

In the anti-CD19×CD3 bispecific single chain antibodies, $V_L$CD19 and $V_H$CD19 constitute functional domains binding to human CD19 antigen, while $V_L$CD3 and $V_H$CD3 constitute functional domains binding to human CD3 antigen. Therefore the anti-CD19×CD3 bispecific single chain antibody can effectively combine T cells (with CD3 antigen) and CD19 positive cancer cells, activating T lymphocytes and releasing cytokines, perforin, particle enzyme and Fas/FasL to kill tumor cells. It is not bound by MHC I molecules, and does not require co-stimulatory molecules.

In an eighth aspect, the present invention provides use of the minicircle DNA having genetically engineered antibody gene expression cassette as described in the third aspect, use of the preparation method of the minicircle DNA having genetically engineered antibody gene expression cassette as described in the forth aspect, use of the host as described in the fifth aspect, use of the genetically engineered antibody as described in the sixth aspect, and use of the preparation method of the genetically engineered antibody as described in the seventh aspect.

Preferably, the minicircle DNA having genetically engineered antibody gene expression cassette as described in the third aspect, the preparation method of the minicircle DNA having genetically engineered antibody gene expression cassette as described in the forth aspect, the host as described in the fifth aspect, the genetically engineered antibody as described in the sixth aspect, and the preparation method of the genetically engineered antibody as described in the seventh aspect can be used in preparing medicines for cancers.

More preferably, the minicircle DNA having genetically engineered antibody gene expression cassette as described in the third aspect, the preparation method of the minicircle DNA having genetically engineered antibody gene expression cassette as described in the forth aspect, the host as described in the fifth aspect, the genetically engineered antibody as described in the sixth aspect, and the preparation method of the genetically engineered antibody as described in the seventh aspect can be used in preparing medicines for CD19 or CD20 positive cancer disease.

In a ninth aspect, the present invention provides a method for administrating the genetically engineered antibody of the seventh aspect, comprising any one or more methods selected from the group consisting of:

(1) administrating the minicircle DNA alone;

(2) administrating the minicircle DNA with one of chemotherapy, radiotherapy, surgery, biotherapy and immunotherapy, or with their combinations.

(3) delivering the minicircle DNA into a patient for therapy by a targeted delivery approach;

(4) transfecting immune effector cell with the minicircle DNA by an in vitro transfection technique, and then transporting the immune effector cell transfected with the minicircle DNA into a patient for therapy.

Preferably, in method (4), the immune effector cell is one selected from the group consisting of T lymphocytes, natural killer cells, macrophages and stem cells Preferably, in method (4), the immune effector cell is CIK cell or D-CIK cell.

In a tenth aspect, the present invention provides methods for using genetically engineered antibody to treat cancer or tumor, comprising any one method selected from the group consisting of:

(1) administrating the minicircle DNA alone to treat cancer or tumor;

(2) administrating the minicircle DNA with one of chemotherapy, radiotherapy, surgery, biotherapy and immunotherapy, or with their combinations to treat cancer or tumor;

(3) delivering the minicircle DNA into a patient for therapy by a targeted delivery approach to treat cancer or tumor;

(4) transfecting immune effector cell with the minicircle DNA by an in vitro transfection technique, and then transporting the immune effector cell transfected with the minicircle DNA into a patient to treat cancer or tumor.

Preferably, the genetically engineered antibody is as described in the seventh aspect of the present invention, or the genetically engineered antibody is prepared by the method as described in the eighth aspect of the present invention.

Preferably, in method (4), the immune effector cell is one selected from the group consisting of T lymphocytes, natural killer cells, macrophages and stem cells.

In method (4), the immune effector cell is CIK cell or D-CIK cell.

Preferably, in method (4), genetically engineered antibodies of 0.01-0.04 ug/ul are mixed with immune effector cells of $4\times10^4\sim16\times10^4$.

More preferably, the genetically engineered antibody is at least one of anti-CD20×CD3 genetically engineered antibody and CD19×CD3 genetically engineered antibody.

Preferably, in method (4), the genetically engineered antibody is at least one genetically engineered antibody described in the seventh aspect of the present invention.

Preferably, in method (4), the genetically engineered antibody is at least one genetically engineered antibody prepared as the method described in the eighth aspect of the present invention.

Under such preferred conditions, ratio of the number of the immune effector cell to targeted cells is in a range of 2-8:1, wherein the targeted cells are cancer cells or tumor cells.

The minicircle DNA containing attR site is devoid of sequence of pronucleus plasmid and free from chromosomal DNA of human and mammalian cells, providing stable and persistent expression of genetically engineered antibody. The minicircle DNA can be used alone for targeted therapy, such as delivery to a patient for expression of genetically engineered antibody, leading T cell to specifically kill tumor cell.

The minicircle DNA of the present invention can be used for transfecting immune effector cell of a patient in vitro, and then the immune effector cell transfected with the minicircle DNA is transported into the patient for therapy.

The minicircle DNA of the present invention can be used for therapy in combination with chemotherapy, radiotherapy, surgery, biotherapy and immunotherapy.

The present invention provides the following advantages:

(1) The minicircle DNA recombinant parental plasmid having genetically engineered antibody gene expression cassette provided by the present invention completes the process of recombination in host strains, eliminating prokaryotic plasmid elements to form minicircle DNA having genetically engineered antibody.

(2) The minicircle DNA having genetically engineered antibody gene cassette provides a long-term and stable expression of genetically engineered antibody gene in host cells. The minicircle DNA is a kind of effective, safe, economical gene therapy vector, since it is safer, more economical than virus vectors, more effective than normal vectors. In addition, the minicircle DNA expresses genetically engineered antibody with Flag tag and his6 tag, benefiting purification and subsequent research.

(3) The genetically engineered antibody of the present invention is capable of combining T cells (with CD3 antigen) with tumor cells, and guiding T cells to kill tumor cells.

(4) The minicircle DNA having genetically engineered antibody gene cassette, host containing the minicircle DNA, and genetically engineered antibody expressed by the minicircle DNA can be used alone, or combined with one or more therapy approaches of chemotherapy, radiation, surgery, biotherapy and immunotherapy, for cancer patients.

DETAILED DESCRIPTION OF ILLUSTRATED EMBODIMENTS

The invention will now be described in detail on the basis of preferred embodiments. It is to be understood that various changes may be made without departing from the spirit and scope of the inventions.

The plasmid vector pUC57, pCMV.bpA, strains DH5α and *E. coli* TOP10 employed in the embodiments of the present invention were purchased from Invitrogen Company. The ZYCY10P3S2T engineered strains (*E. coli*) was purchased from SBI Company. The empty p2ΦC31 was constructed according to the methods described in Chen Z Y et al., Minicircle DNA vectors devoid of bacterial DNA result in persistent and high-level transgene expression in vivo, Molecular Therapy, 2003, Volume 8, Number 3, 495-500; Chen Z Y et al., Improved production and purification of minicircle DNA vector free of plasmid bacterial sequences and capable of persistent transgene expression in vivo, Human Gene Therapy, 2005, Volume 16, Number 1, 126-131 and U.S. Pat. No. 7,897,380 B2. Methods for constructing empty plasmid pMC.BESPX and complete genome sequence can be found in Chen Z Y et al., A robust system for production of minicircle DNA vectros, Nature Biotechnology, 2010, Volume 28, Number 12, 1289-1291. All the reagents used herein can be purchased from the market.

Example 1

A method for constructing minicircle DNA recombinant parental plasmid p2ΦC31.Bab having genetically engineered antibody gene expression cassette comprises the following steps.

Figure 1:
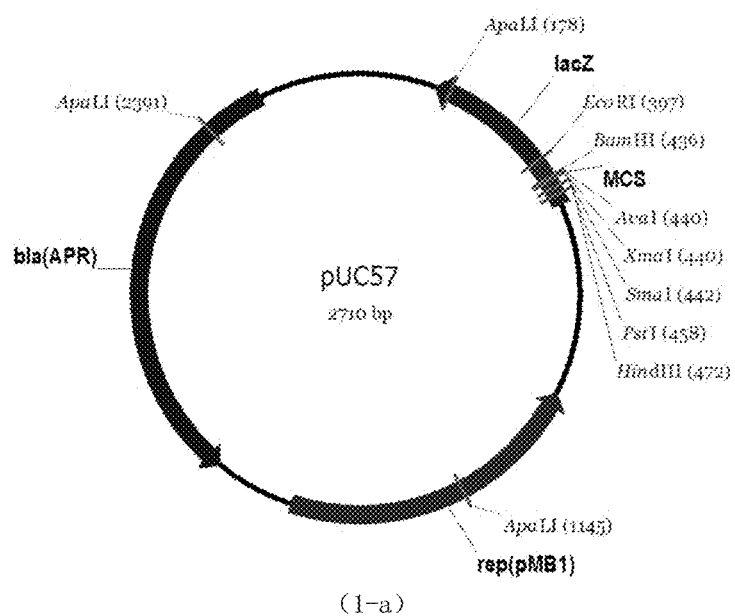
FIG. 1 shows pUC57 and pCMV.bpA vector provided in Example 1.
Figure 1:
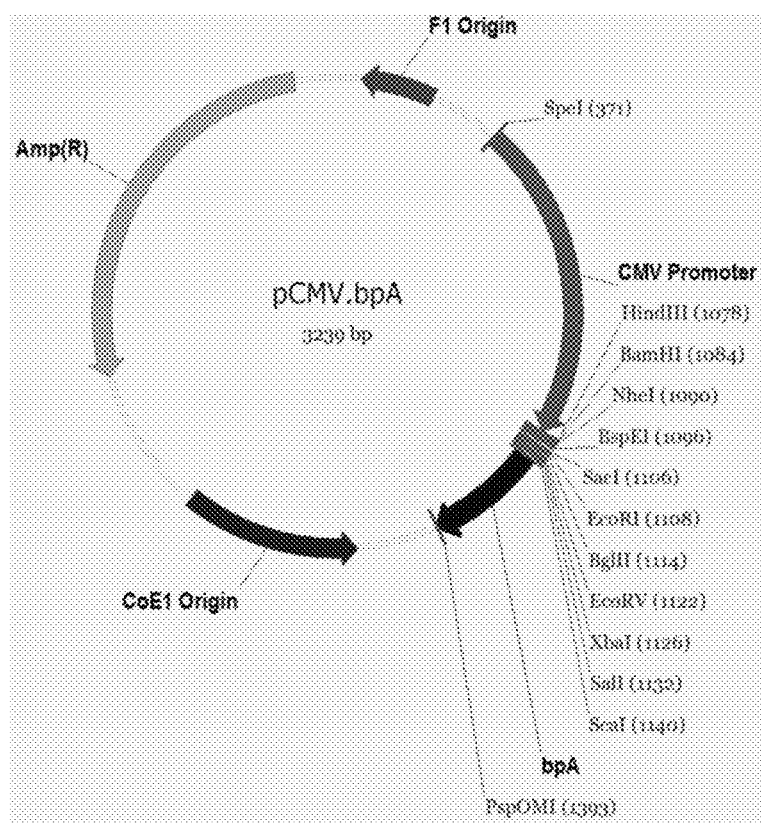
Figure 2:
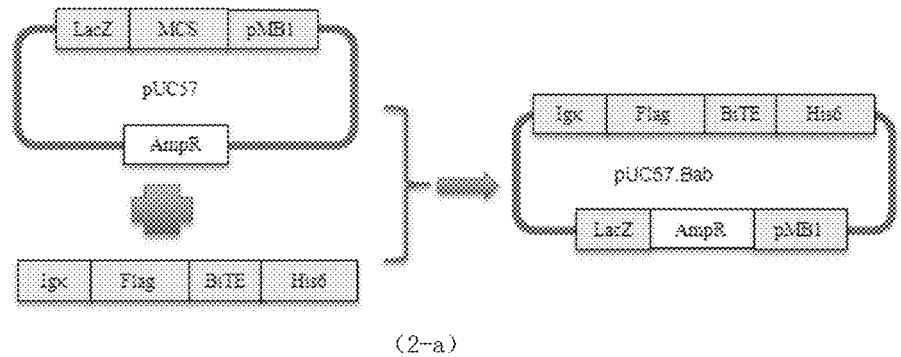
FIG. 2 shows process of constructing the minicircle DNA recombinant parental plasmid p2ΦC31.Bab having genetically engineered antibody gene expression cassette provided in Example 1.
Figure 2:
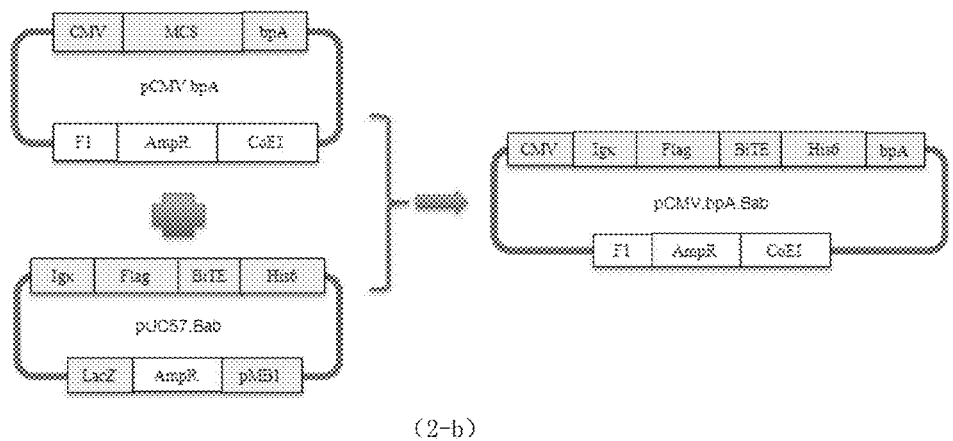
Figure 2:
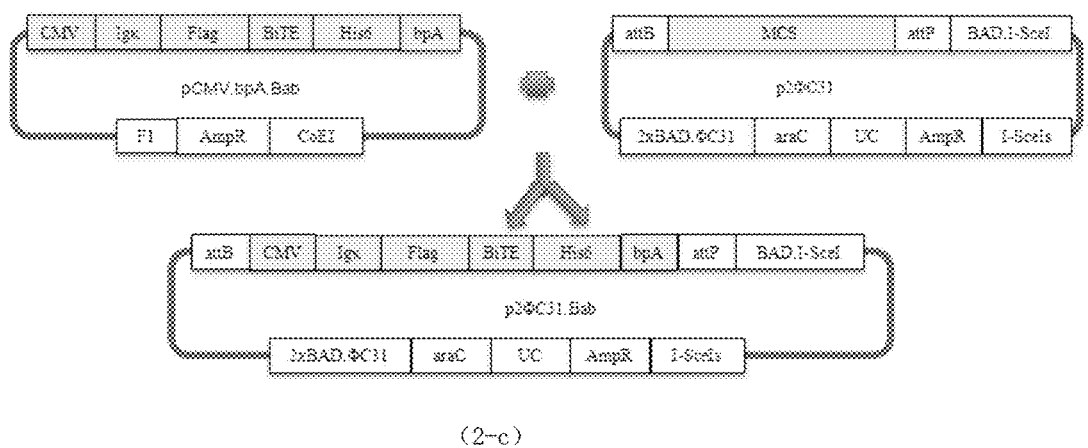

(1) Construction of recombinant vector pUC57.Bab having genetically engineered antibody anti-CD19×CD3 gene (i.e. CD19×CD3 BiTE) as shown in FIG. 2-*a*.

(1a) We synthesized HindIII enzyme site-base sequence encoding immunoglobulin chain signal peptide (SEQ ID NO:24)-base sequence encoding Flag tag (SEQ ID NO:25)-gene sequence of BiTE (SEQ ID NO:12-SEQ ID NO:21-SEQ ID NO:13-SEQ ID NO:22-SEQ ID NO:16-SEQ ID NO:19-SEQ ID NO:14)-base sequence encoding His6 tag (SEQ ID NO:26)-stop codon (TTA)-base sequence of EcoRI enzyme site linked sequentially, in the manner of complete genome sequence synthesis, wherein SEQ ID NO:12-SEQ ID NO:21-SEQ ID NO:13-SEQ ID NO:22-SEQ ID NO:16-SEQ ID NO:19-SEQ ID NO:14 correspond to $V_L$CD19-linker1-$V_H$CD19-linker2-$V_H$CD3-linker1-$V_L$CD3 base sequences encoding BiTE, respectively. The base sequences linked sequentially is only one strain of the double strains of complete genome synthesis genes (DNA fragment), and the other strain is complementary to the base sequences linked sequentially.

(1b) pUC57 vector and the base sequences synthesized from step (1a) were cut with HindIII and EcoRI. The results were characterized by agarose gel electrophoresis. The linear pUC57 vectors and nucleotide fragments were recovered.

Figure 3:
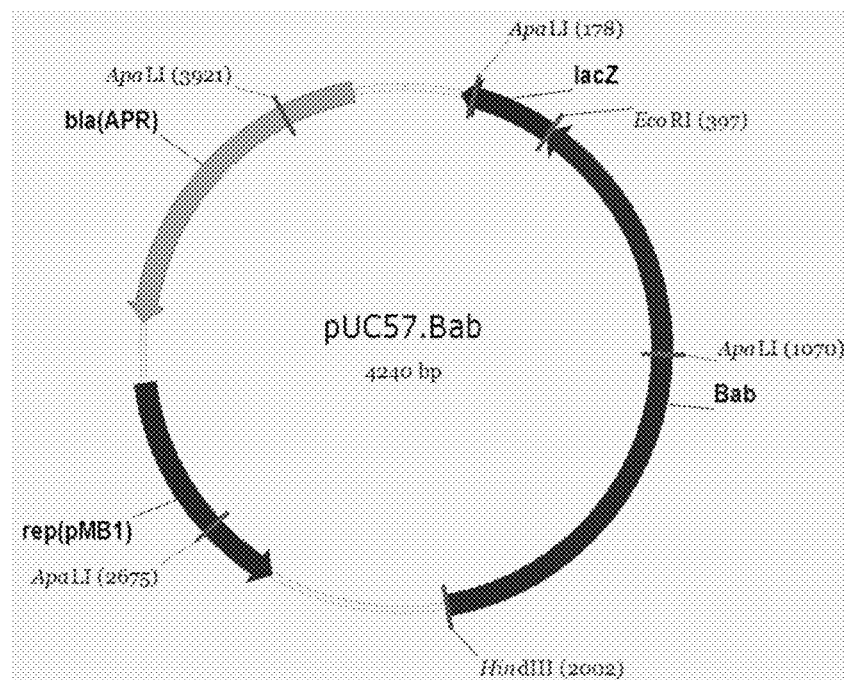
FIG. 3 shows the minicircle DNA recombinant parental plasmid pUC57.Bab provided in Example 1.

(1c) We connected the nucleotide fragments and linear pUC57 vectors obtained from step (1b) in a molar ratio of 3:1 with T4 DNA ligase at 16° C. overnight or at room temperature for 2 hours, followed by adding the product to *E. coli* DH5α strains competent cells suspensions for transformation, and inoculated into a LB plate containing ampicillin. The reaction was incubated at 37° C. overnight. Single colonies were picked up for recombinant plasmid vector verification with two enzymes (HindIII and EcoRI). We further confirmed the positive cloning by sequencing. The vector inserted with nucleotide fragment identical to the base sequences synthesized from step (1a) was named as pUC57.Bab (4240 bp), of which the plasmid map is shown in FIG. 3.

(2) Construction of recombinant expression vector pCMV. bpA. Bab having genetically engineered antibody gene expression cassette as shown in FIG. 2-*b*.

(2a) pCMV. bpA vector and pUC57.Bad were cut with HindIII and EcoRI. The results were characterized by agarose gel electrophoresis. The linear pCMV.bpA vectors and nucleotide fragments were recovered.

Figure 4:
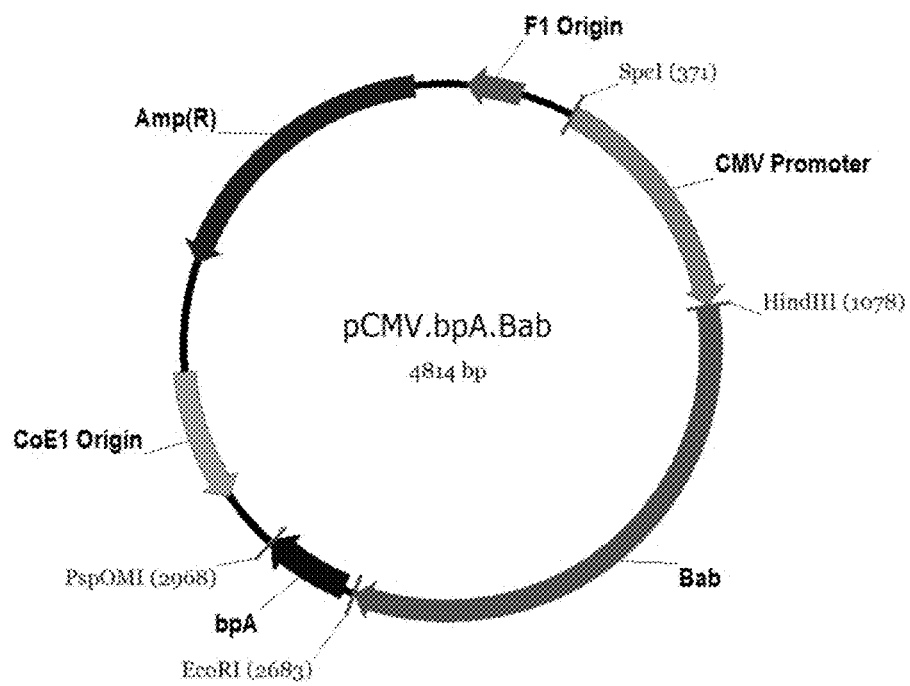
FIG. 4 shows the recombination expression vector pCMV.bpA. Bab provided in Example 1.

(2b) We connected the nucleotide fragments and linear pCMV.bpA vectors obtained from step (2a) in a molar ratio of 3:1 with T4 DNA ligase at 16° C. overnight or at room temperature for 2 hours, followed by adding the product to *E. coli* DH5a strains competent cells suspensions for transformation, and inoculated into a LB plate containing ampicillin. The reaction was incubated at 37° C. overnight. Single colonies were picked up for recombinant plasmid vector verification with two enzymes (HindIII and EcoRI). We further confirmed the positive cloning by sequencing. The vector inserted with nucleotide fragment identical to the base sequences synthesized from step (1a) was named as pCMV. bpA. Bab(4814 bp), of which the plasmid map is shown in FIG. 4.

(3) Construction of minicircle DNA recombinant parental plasmid p2ΦC31.Bab having genetically engineered antibody gene expression cassette as shown in FIG. 2-*c*.

(3a) The positive cloning picked up from step (1c) was incubated. The pCMV.bpA. Bab recombinant expression vectors were purified using plasmid purification kits (OMEGA Company).

(3b) p2ΦC31 vector and pCMV. bpA. Bab recombinant expression vector obtained from step (2a) were cut with SpeI and Psp OMI endonuclease. The results were characterized by agarose gel electrophoresis. The linear p2ΦC31 vectors and nucleotide fragments (DNA fragments containing genetically engineered antibody gene expression cassette) were recovered.

Figure 5:
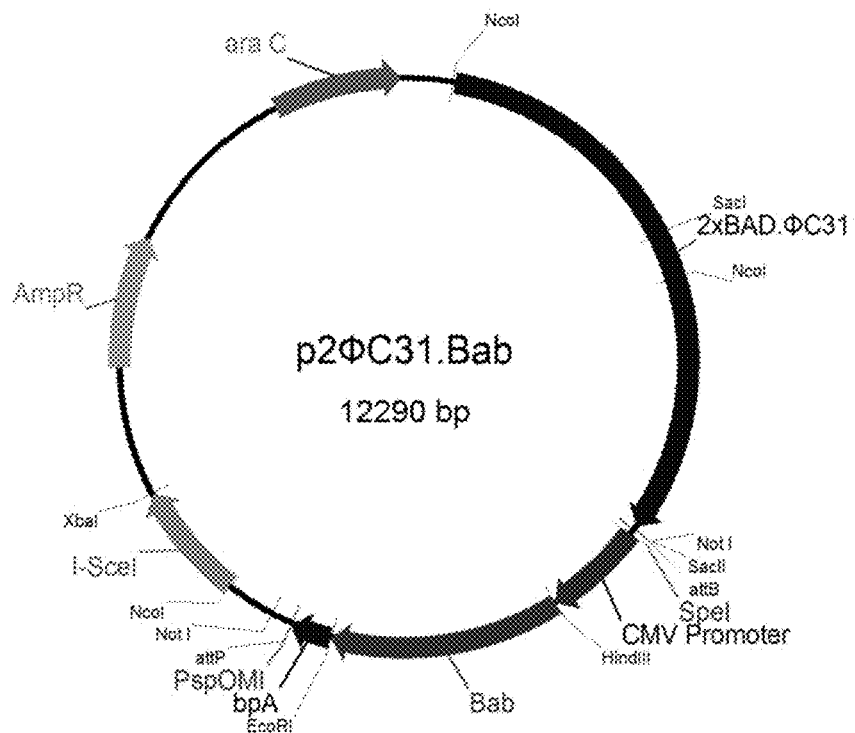
FIG. 5 shows the minicircle DNA recombinant parental plasmid p2ΦC31.Bab provided in Example 1.

(3c) We connected the nucleotide fragments and linear p2ΦC31 plasmid obtained from step (2) in a molar ratio of 3:1 with T4 DNA ligase at 16° C. overnight or at room temperature for 2 hours, followed by adding the product to *E. coli* DH5a strains competent cells suspensions for transformation, and inoculated into a LB plate containing ampicillin. The reaction was incubated at 37° C. overnight. Single colonies were picked up for recombinant plasmid vector verification with two enzymes (HindIII and EcoRI). We further confirmed the positive cloning by sequencing. p2ΦC31.Bab (12290 bp) was obtained. The p2ΦC31.Bab is the minicircle DNA recombinant parental plasmid having genetically engineered antibody gene expression cassette, of which the plasmid map is shown in FIG. 5.

Example 2

Figure 6:
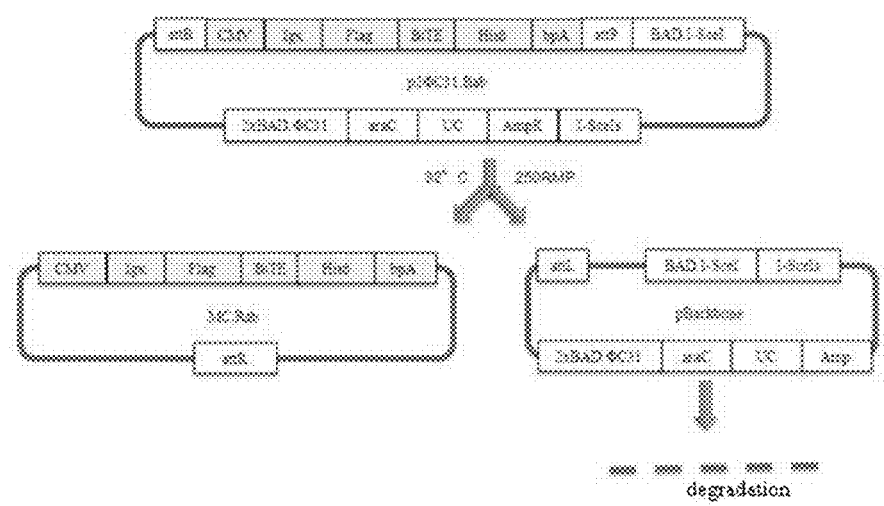
FIG. 6 shows process of preparing the minicircle DNA MC.Rab with the minicircle DNA recombinant parental plasmid p2ΦC31.Bab provided in Example 2.

Combined with the flowchart of minicircle DNA having genetically engineered antibody gene cassette as shown in FIG. 6, the embodiment provides a method for preparing minicircle DNA having genetically engineered antibody gene cassette, comprising the following steps.

(1a) TOP 10 was transformed with p2ΦC31.Bab plasmid obtained from the Example 1, and incubated overnight.

(1b) The bacteria of the culture medium obtained from step (1a) were suspended in fresh inducing medium containing 1% arabinose and incubated at 32° C. with shaking at 250 rpm for 2 hours. We induced the expression of ΦC31 recombinase to mediate the formation of bacterial plasmid (pBackbone) DNA containing attL site and minicircle DNA containing attR site.

Figure 7:
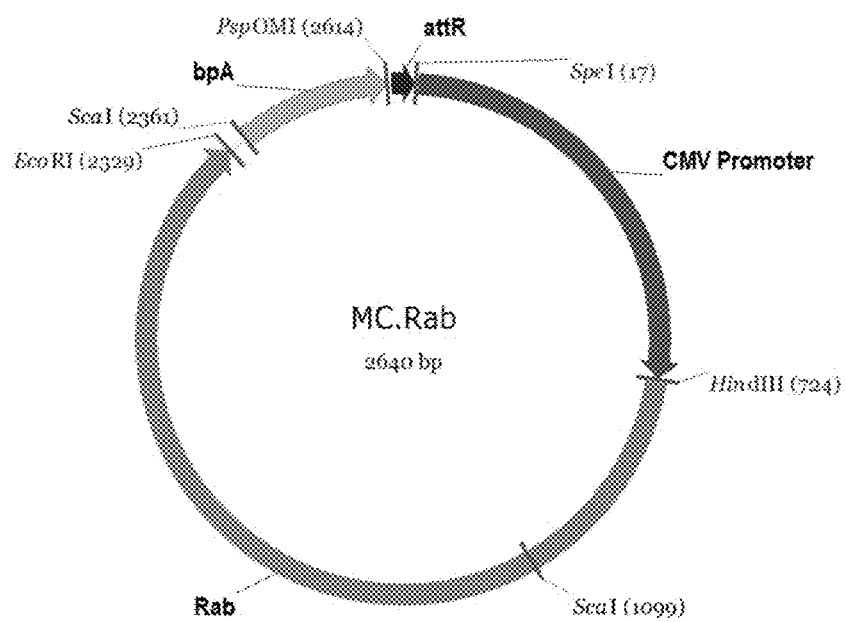
FIG. 7 shows minicircle DNA MC.Rab provided in Example 2.

(1c) The incubation temperature was then elevated to 37° C. We induced I-Sce1 endonuclease to cut pBackbone at I-Sce1 sites. The pBackbone DNA chain was rapidly degraded by exonuclease of bacteria. Minicircle DNA, as the only extrachromosomal circular DNA, was extracted with affinity column. The plasmid map of minicircle DNA having genetically engineered gene expression cassette (MC.Rab(2640 bp)) is shown in FIG. 7.

In order to fully illustrate the beneficial effects of the present invention, we also provide Examples 3 to 5, wherein Example 3 differs from Example 1 in that the base sequences of BiTE in Example 3 (step (1a)) are as follows:
SEQ ID NO:12-SEQ ID NO:20-SEQ ID NO:13-SEQ ID NO:22-SEQ ID NO:15-SEQ ID NO:21-SEQ ID NO:17

Example 4 differs from Example 1 in that the base sequences of BiTE in Example 4 (step (1a)) are as follows:
SEQ ID NO:13-SEQ ID NO:21-SEQ ID NO:12-SEQ ID NO:22-SEQ ID NO:14-SEQ ID NO:19-SEQ ID NO:16

Example 5 differs from Example 1 in that the base sequences of BiTE in Example 5 (step (1a)) are as follows:
SEQ ID NO:13-SEQ ID NO:19-SEQ ID NO:12-SEQ ID NO:22-SEQ ID NO:18-SEQ ID NO:20-SEQ ID NO:15;

In Examples 3-5, minicircle DNA parental plasmid having genetically engineered antibody gene expression cassette were constructed according to the method described in Example 2.

Construction of Minicircle DNA Parental Plasmid Containing CD20×CD3 BiTE

In order to fully illustrate the beneficial effects of the present invention, we also provide an embodiment of constructing minicircle DNA containing genetically engineered antibody (CD20×CD3 BiTE), wherein this embodiment differs from Example 1 in that the base sequences of BiTE of this embodiment (step (1a)) are as follows:
SEQ ID NO:33-SEQ ID NO:21-SEQ ID NO:34-SEQ ID NO:22-SEQ ID NO:18-SEQ ID NO:20-SEQ ID NO:15

Specifically, synthesizing HindIII enzyme site-base sequence encoding immunoglobulin κ chain signal peptide (SEQ ID NO:24)-base sequence encoding Flag tag (SEQ ID NO:25)-gene sequence of BiTE (SEQ ID NO:33-SEQ ID NO:21-SEQ ID NO:34-SEQ ID NO:22-SEQ ID NO:18-SEQ ID NO:20-SEQ ID NO:15)-base sequence encoding His6 tag (SEQ ID NO:26)-stop codon (TTA)-base sequence of EcoRI enzyme site linked sequentially, in the manner of complete genome sequence synthesis, wherein SEQ ID NO:33-SEQ ID NO:21-SEQ ID NO:34-SEQ ID NO:22-SEQ ID NO:18-SEQ ID NO:20-SEQ ID NO:15 correspond to $V_L$CD20-linker1-$V_H$CD20-linker2-$V_H$CD3-linker1-$V_L$CD3 base sequences encoding BiTE, respectively. The base sequences linked sequentially was only one strain of the double strains of complete genome synthesis genes (DNA fragment), and the other strain is complementary to the base sequences linked sequentially.

Construction of Minicircle DNA Containing CD20×CD3 BiTE

The obtained minicircle DNA parental plasmid having CD20×CD3 BiTE were constructed according to the method described in Example 2.

Example 6

A method for constructing minicircle DNA recombinant parental plasmid pMC.Bab having genetically engineered antibody gene expression cassette comprises the following steps.

(1) Construction of pUC57.Bab recombinant vector having anti-CD19×CD3 genetically engineered antibody (BiTE) gene, according to the method described in Example 1 (step 1).

(2) Construction of pCMV. bpA. Bab recombinant vector having genetically engineered antibody gene expression cassette, according to the method described in Example 1 (step 2).

Figure 8:
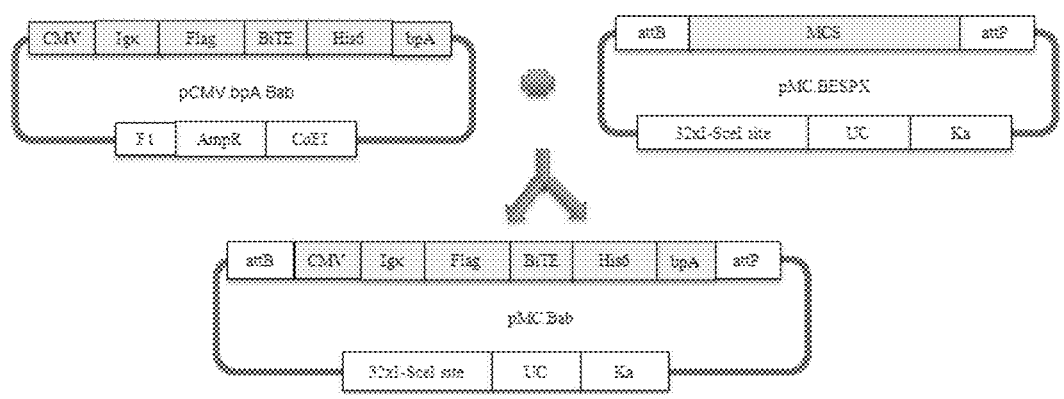
FIG. 8 shows process of constructing the minicircle DNA recombinant parental plasmid pMC.Bab having genetically engineered antibody gene expression cassette provided in Example 6.

(3) Construction of minicircle DNA recombinant parental plasmid pMC.Bab having genetically engineered antibody gene expression cassette as shown in FIG. 8.

(3a) The positive cloning picked up from step (1c) was incubated. The pCMV.bpA. Bab recombinant expression vectors were purified using plasmid purification kits (OMEGA Company).

(3b) pMC.BESPX vector and pCMV. bpA. Bap recombinant expression vector obtained from step (2a) were cut with SpeI and Psp OMI endonuclease. The results were characterized by agarose gel electrophoresis. The linear pMC.BESPX vectors and nucleotide fragments were recovered.

Figure 9:
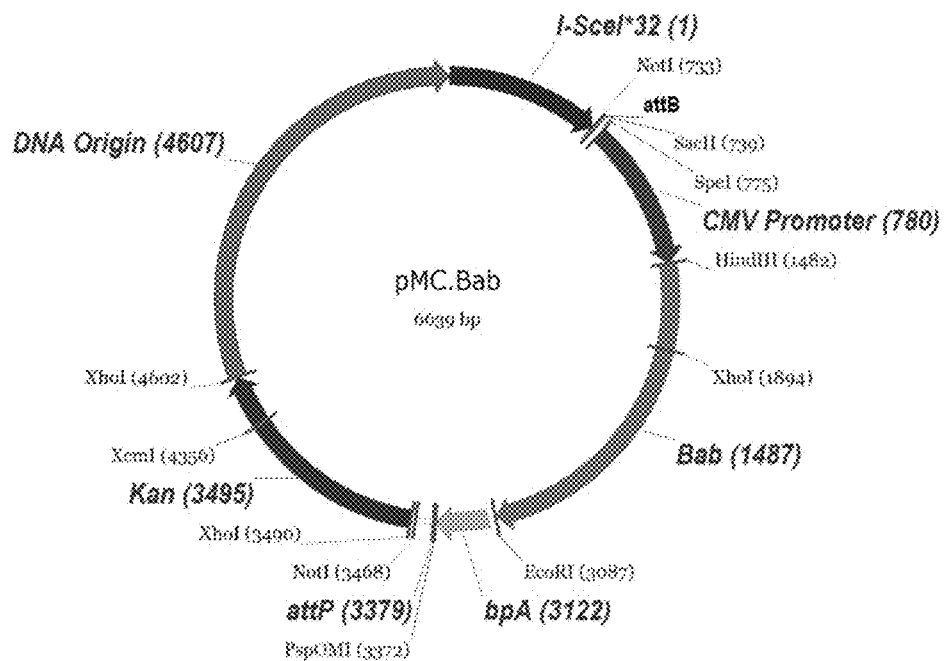
FIG. 9 shows the minicircle DNA recombinant parental plasmid pMC.Bab provided in Example 6.

(3c) We connected the nucleotide fragments and linear pMC.BESPX plasmids obtained from step (2) in a molar ratio of 3:1 with T4 DNA ligase at 16° C. overnight or at room temperature for 2 hours, followed by adding the product to *E. coli* DH5a strains competent cells suspensions for transformation, and inoculated into a LB plate containing ampicillin. The reaction was incubated at 37° C. overnight. Single colonies were picked up for recombinant plasmid vector verification with two enzymes (HindIII and EcoRI). We further confirmed the positive cloning by sequencing. pMC.Bab (6639 bp) was obtained. The pMC.Bab is the minicircle DNA recombinant parental plasmid having genetically engineered antibody gene expression cassette, of which the plasmid map is shown in FIG. 9.

Example 7

Figure 10:
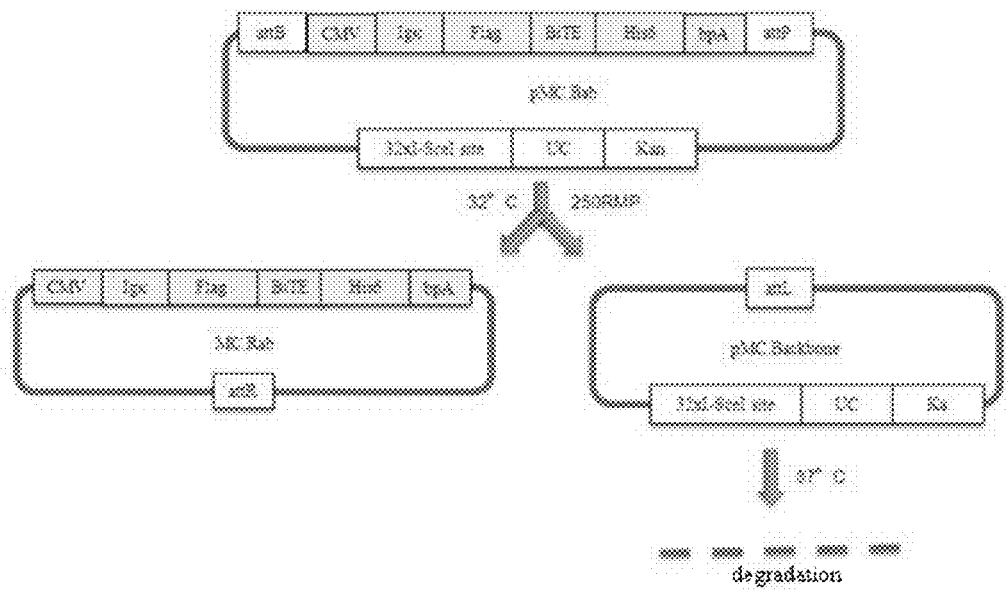
FIG. 10 shows process of preparing the minicircle DNA MC.Rab with the minicircle DNA recombinant parental plasmid pMC.Bab provided in Example 6.

Combined with the flowchart of minicircle DNA having genetically engineered antibody gene cassette as shown in FIG. 10, the embodiment provides a method for preparing minicircle DNA having genetically engineered antibody gene cassette, comprising the following steps.

(1a) Engineered strains ZYCY10P3S2T was transformed with pMC.Bab plasmid obtained from the Example 6, and incubated overnight.

(1b) The bacteria of the culture medium obtained from step (1a) were suspended in fresh inducing medium containing 1% arabinose and incubated at 32° C. with shaking at 250 rpm for 2 hours. We induced the expression of ΦC31 recombinase to mediate the formation of bacterial plasmid (pBackbone) DNA containing attL site and minicircle DNA containing attR site.

(1c) The incubation temperature was then elevated to 37° C. We induced I-Sce1 endonuclease to cut pBackbone at I-Sce1 sites. The pBackbone DNA chain was rapidly degraded by exonuclease of bacteria. Minicircle DNA, as the only extrachromosomal circular DNA, was extracted with affinity column. The plasmid map of minicircle DNA having genetically engineered gene expression cassette (MC.Rab(2640 bp)) is shown in FIG. 7.

pMC.BESPX has no base sequences encoding ΦC31 recombinase and I-Sce1 endonuclease that presents in p2ΦC31 vectors, thus reducing base sequences contamination on minicircle DNA, making the minicircle DNA parental plasmid have better quality. Since the pMC.BESPX has no base sequences encoding ΦC31 recombinase and I-Sce1 endonuclease, it may reduce contaminations of nucleotide sequence of recombinase and endonuclease to minicircle DNA. However, minicircle DNA parental plasmid of Example 6 was used to produce minicircle DNA with ZYCY10P3S2T engineered strains. Because the pMC.Bab without nucleotide sequence encoding ΦC31 recombinase and I-Sce1 endonuclease should be used with ZYCY10P3S2T engineered bacteria to generate in vivo site-specific recombination and ultimately produce a minicircle DNA, i.e. MC.Rab.

Figure 11:
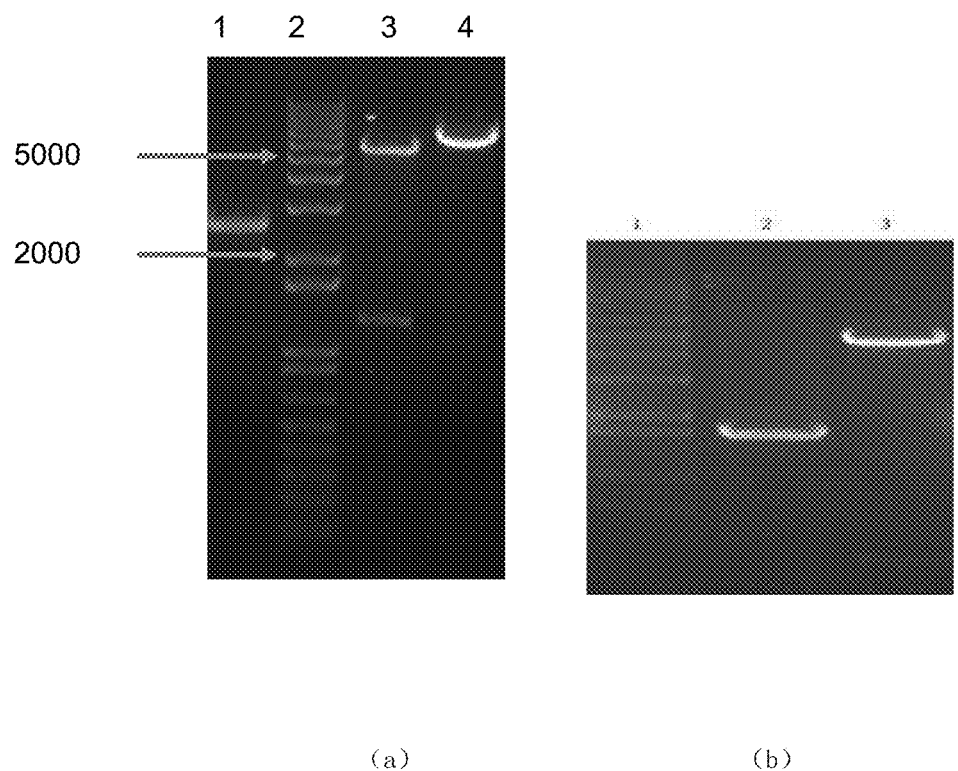
FIG. 11 shows an agarose gel electrophoresis of minicircle DNA recombinant plasmid p2ΦC31.Bab of Example 2 cut with enzyme before and after induction.

In order to fully illustrate the beneficial effects of the present invention, an agarose gel electrophoresis of minicircle DNA recombinant parental plasmid pMC.Bab(6639 bp) of Example 6 cut with enzyme before and after induction is provided. As shown in FIG. 11(*a*), lane 1 is the results of cutting the purified plasmid induced by arabinose with EcoRI and SacII. The appearance of the only band indicates successful recombination of parental plasmid pMC.Bab and production of two kinds of circles. The circle with bacterial sequence is degraded by the enzyme in bacterial, while the remaining minicircle DNA(2640) without EcoRI and SacII cannot be cut, i.e. the band shows in lane 1. Lane 2 is DNA marker, 1 Kb Plus DNA Ladder (purchased from Invitrogen). Lane 3 is the results of cutting the purified plasmid before the induction by arabinose with EcoRI and XCMI. The appearance of two bands indicates that parental plasmid pMC.Bab exists in ZYCY10P3S2T before the induction. Lane 4 is the results of cutting the purified plasmid before the induction by arabinose with EcoRI. The appearance of the only band indicates successful transformation of parental plasmid pMC.Bab in ZYCY10P3S2T.

In order to fully illustrate the beneficial effects of the present invention, we also provide Examples 8 to 10, wherein Example 8 differs from Example 6 in that the base sequences of BiTE in Example 8 (step (1a)) are as follows:
SEQ ID NO:12-SEQ ID NO:20-SEQ ID NO:13-SEQ ID NO:22-SEQ ID NO:15-SEQ ID NO:21-SEQ ID NO:17

Example 9 differs from Example 6 in that the base sequences of BiTE in Example 9 (step (1a)) are as follows:
SEQ ID NO:13-SEQ ID NO:21-SEQ ID NO:12-SEQ ID NO:22-SEQ ID NO:14-SEQ ID NO:19-SEQ ID NO:16

Example 10 differs from Example 6 in that the base sequences of BiTE in Example 10 (step (1a)) are as follows:
SEQ ID NO:13-SEQ ID NO:19-SEQ ID NO:12-SEQ ID NO:22-SEQ ID NO:18-SEQ ID NO:20-SEQ ID NO:15;

In Examples 8-10, minicircle DNA parental plasmid having genetically engineered antibody gene expression cassette were constructed according to the method described in Example 7.

Construction of Minicircle DNA Parental Plasmid (pMC.Bab-CD20) Containing CD20×CD3 BiTE In order to fully illustrate the beneficial effects of the present invention, we also provide an embodiment of constructing minicircle DNA containing genetically engineered antibody (CD20×CD3 BiTE), wherein this embodiment differs from Example 6 in that the base sequences of BiTE of this embodiment (step (1a)) are as follows:
SEQ ID NO:33-SEQ ID NO:21-SEQ ID NO:34-SEQ ID NO:22-SEQ ID NO:16-SEQ ID NO:19-SEQ ID NO:14

Specifically, we synthesized HindIII enzyme site-base sequence encoding immunoglobulin κ chain signal peptide (SEQ ID NO:24)-base sequence encoding Flag tag (SEQ ID NO:25)-gene sequence of BiTE (SEQ ID NO:33-SEQ ID NO:21-SEQ ID NO:34-SEQ ID NO:22-SEQ ID NO:16-SEQ ID NO:19-SEQ ID NO:14)-base sequence encoding His6 tag (SEQ ID NO:26)-stop codon (TTA)-base sequence of EcoRI enzyme site linked sequentially, in the manner of complete genome sequence synthesis, wherein SEQ ID NO:33-SEQ ID NO:21-SEQ ID NO:34-SEQ ID NO:22-SEQ ID NO:16-SEQ ID NO:19-SEQ ID NO:14 correspond to $V_L$CD20-linker1-$V_H$CD20-linker2-$V_H$CD3-linker1-$V_L$CD3 base sequences encoding BiTE, respectively. The base sequences linked sequentially was only one strain of the double strains of complete genome synthesis genes (DNA fragment), and the other strain is complementary to the base sequences linked sequentially.

Construction of Minicircle DNA Containing CD20×CD3 BiTE

The obtained minicircle DNA parental plasmid having CD20×CD3 BiTE were constructed according to the method described in Example 7.

In order to fully illustrate the beneficial effects of the present invention, an agarose gel electrophoresis of minicircle DNA recombinant parental plasmid pMC.Bab-CD20 having CD20×CD3 BiTE cut with enzyme before and after induction is provided. As shown in FIG. 11(b), lane 1 is DNA marker, 1 Kb Plus DNA Ladder (purchased from Invitrogen, NO. 10787026). Lane 2 is the results of cutting the purified plasmid induced by arabinose with EcoRI and SacII. The appearance of the only band indicates successful recombination of parental plasmid pMC.Bab and production of two kinds of circles. The circle with bacterial sequence is degraded by the enzyme in bacterial, while the remaining minicircle DNA without EcoRI and SacII cannot be cut, i.e. the band shows in lane 2. Lane 3 is the results of cutting the purified plasmid before the induction by arabinose with EcoRI and XCMI. The appearance of two bands indicates existence of parental plasmid pMC.Bab in ZYCY10P3S2T before the induction and successful transformation of parental plasmid pMC.Bab-2 in ZYCY10P3S2T.

Example 11

A method for expressing and purifying anti-CD19×CD3 genetically engineered antibody comprises the following steps.

(1) Expression of recombinant antibody in CHO cells and CIK cells.

CHO cells and CIK cells were transfected with p2ΦC31.Bab or MC.Rab by using superfect plasmid transfection kits (Invitrogen Company). After a three-day incubation in serum-free medium, supernatant of CHO cells and CIK cells were collected and subjected to flow cytometry for detecting the expression of CD19×CD3 genetically engineered antibody.

(2) Purification of anti-CD19×CD3 genetically engineered antibody.

CHO cell culture supernatant was subjected to cold ultracentrifugation, and the supernatant was collected. The collected supernatant was then subjected to nickel column chromatography, monitoring at 280 nm. The unbound proteins were eluted with a cleaning liquid, while the bounded proteins were eluted with an eluent to obtain purified anti-CD19×CD3 genetically engineered antibody. We detected protein concentration by ELISA approach. The obtained eluent comprising an anti-CD19×CD3 genetically engineered antibody was desalted, purified, lyophilized, and then placed in −20° C. for a long-term preservation.

Example 12

A method for binding activity in vitro using anti-CD19×CD3 genetically engineered antibody comprises the following steps.

(1) Detection of binding activity of anti-CD19×CD3 genetically engineered antibody to Raji cells by flow cytometry (1a) As an experimental group, anti-CD19×CD3 genetically engineered antibody and Raji cells were mixed with 1% bovine serum albumin (BSA) and phosphate buffered saline (staining buffer) containing 0.02% sodium azide. As a control group, Raji cells were transfected with p2ΦC31 empty plasmid, and incubated on ice for 30 minutes.

(1b) The incubation solution obtained from step (1a) was subjected to centrifugation. The obtained cells were washed with PBS twice. Fluorescein His6 antibody marked by isothiocyanate (FITC) were added, and incubated on ice for 30 minutes.

Figure 12:
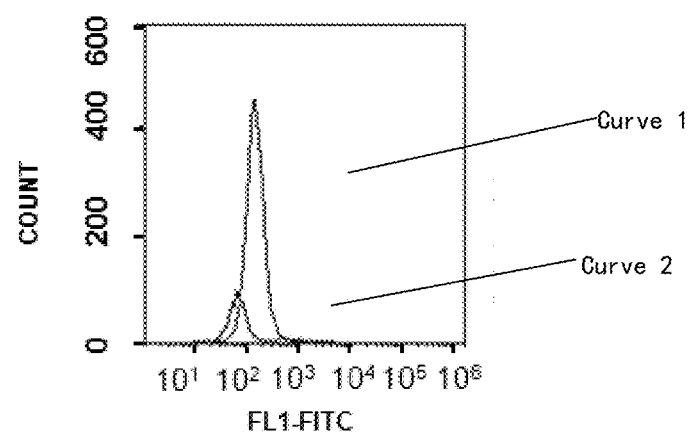
FIG. 12 shows flow cytometry analysis of binding of anti-CD19×CD3 genetically engineered antibody of Example 12 to Raji.

(1c) After the incubation solution obtained from step (1b) was centrifugated, the obtained cells were washed with PBS twice. We resuspended the cells with 200 μl staining buffer, and detected by flow cytometry. Results are shown in FIG. 12. Curve 1 shows the control group, while curve 2 shows the experimental group. It indicates that the anti-CD19×CD3 genetically engineered antibody of the present invention is capable of binding CD19 positive Raji cells.

(2) Detection of binding activity of anti-CD19×CD3 genetically engineered antibody to Jurkat cells by flow cytometry (2a) As an experimental group, anti-CD19×CD3 genetically engineered antibody and Jurkat cells were mixed with 1% bovine serum albumin (BSA) and phosphate buffered saline (staining buffer) containing 0.02% sodium azide, and incubated on ice for 30 minutes.

(2b) The incubation solution obtained from step (2a) was subjected to centrifugation. The obtained cells were washed with PBS twice. Anti-mouse His6 antibody marked by fluorescein isothiocyanate (FITC) were added, and incubated on ice for 30 minutes.

(2c) After the incubation solution obtained from step (2b) was centrifugated, the obtained cells were washed with PBS twice. We resuspended the cells with 200 μl of staining buffer and detected by flow cytometry. Results indicate that the anti-CD19×CD3 genetically engineered antibody of the present invention is capable of binding CD19 positive Raji cells.

Example 13

A method of inhibiting tumor cell growth activity in vitro using anti-CD19×CD3 genetically engineered antibody comprises the following steps.

(1) We extracted peripheral blood of healthy volunteers, and separated the peripheral blood T lymphocytes with T lymphocyte separation liquid, which were then inoculated in a 96-well cell culture plate (1×104/hole, 200 μl).

(2) We prepared anti-CD19×CD3 genetically engineered antibody at different concentrations, followed by adding to the T-lymphocyte culture wells of the step (1). It was incubated for 48 hours, and then 20 μl of MTT thiazolyl blue solution at a concentration of 5 mg/mL were added to each well, and then incubated for 4 hours.

(3) The incubated T lymphocytes of step (2) were centrifuged at a speed of 1000 rpm/min for 10 minutes. The supernatant in the culture wells was removed, and then 200 μl of dimethyl sulfoxide (DMSO) were added to each well with shaking for 10 minutes, dissolving the crystals completely. Subsequently, an enzyme-linked immunosorbent detector was used to measure absorbance at 570 nm wavelength and produce cell growth curve.

Anti-CD19×CD3 genetically engineered antibody of the invention can effectively activate T lymphocytes.

Example 14

A method of inhibiting tumor cell growth activity in vitro using minicircle DNA having anti-CD19×CD3 genetically engineered antibody expression cassette comprises the following steps.

(1) We extracted peripheral blood of healthy volunteers, and separated the peripheral blood T lymphocytes with T lymphocyte separation liquid, which were then transfected with minicircle DNA having. anti-CD19×CD3 genetically engineered antibody expression cassette (MC.Rab) and empty vector (p2ΦC31) separately, using BIO-RAD electroporation system device.

(2) The transfected T lymphocytes of step (1) were inoculated in a 96-well cell culture plate (1×104/hole, 200 μl), followed by a 48-hour incubation. After that, 20 μl of MTT thiazolyl blue solution at a concentration of 5 mg/mL were added to each well, and then incubated for 4 hours.

(3) The incubated T lymphocytes of step (2) were centrifuged at a speed of 1000 rpm/min for 10 minutes. The supernatant in the culture wells was removed, and then 200 μl of dimethyl sulfoxide (DMSO) were added to each well with shaking for 10 min, dissolving the crystals completely. Subsequently, an enzyme-linked immunosorbent detector was used to measure absorbance at 570 nm wavelength and produce cell growth curve.

MC.Rab of the invention can effectively transfect T lymphocytes.

Example 15

A method by using anti-CD19×CD3 genetically engineered antibody and CIK cells mediated cytotoxicity for Raji cells comprises the following steps.

(1) Raji cells were inoculated on a 96-well cell culture plate (1×104/hole, 200 μl). After the appearance of adherent cells, CIK cells were added to culture plates separately according to ratios of CIK cells (effector cell, E) to Raji cells (target cells, T) 10:1, 20:1 and 40:1 (E:T), while recombinant antibody at different concentrations were added to the cell culture wells. Effector cells and target cells were incubated separately and used as control (T).

(2) After the cells were incubated for 96 hours, 20 μl of MTT thiazolyl blue solution at a concentration of 5 mg/mL were added to each well, and then incubated for 4 hours, followed by centrifuging at a speed of 1000 rpm/min for 10 minutes. The supernatant in the culture wells was removed, and then 200 μl of dimethyl sulfoxide (DMSO) were added to each well with shaking for 10 minutes, dissolving the crystals completely.

(3) An enzyme-linked immunosorbent detector was used to measure absorbance at 570 nm wavelength and produce cell killing curve. According to the formula $OD_T-(OD_{E:T}-OD_E)/OD_T \times 100\%$, killing efficiency was calculated. The results show that recombinant antibody of the present invention is able to increase killing activity of CIK cells to kill Raji cells.

Example 16

A Raji cell killing method by using anti-CD19×CD3 genetically engineered antibody and CIK cells comprises the following steps.

(1) Raji cells were inoculated on a 96-well cell culture plate (1×104/hole, 200 μl). After the appearance of adherent cells, CIK cells were transfected with minicircle DNA having anti-CD19×CD3 genetically engineered antibody gene expression cassette (MC.Rab) and empty vector (p2ΦC31) by BIO-RAD electroporation system device, and then were added to culture plates separately according to ratios of CIK cells (effector cell, E) to Raji cells (target cells, T) 10:1, 20:1 and 40:1 (E:T). Effector cells (E) and target cells (T) were incubated separately and used as control.

(2) After the cells were incubated for 96 hours, 20 μl of MTT thiazolyl blue solution at a concentration of 5 mg/mL were added to each well, and then incubated for 4 hours, followed by centrifuging at a speed of 1000 rpm/min for 10 minutes. The supernatant in the culture wells was removed, and then 200 μl of dimethyl sulfoxide (DMSO) were added to each well with shaking for 10 minutes, dissolving the crystals completely.

(3) An enzyme-linked immunosorbent detector was used to measure absorbance at 570 nm wavelength and produce cell killing curve. According to the formula $OD_T-(OD_{E:T}-OD_E)/OD_T \times 100\%$, killing efficiency was calculated. The results show that MC.Rab of the present invention is able to increase killing activity of CIK cells to kill Raji cells.

Example 17

A method for expressing and purifying anti-CD19×CD3 genetically engineered antibody and anti-CD20×CD3 genetically engineered antibody comprises the following steps.

(1) Expression of Recombinant Antibody in 293F Cell.

1.1 Habituated 293F 293T cells were incubated in Expi 293 Expression Medium. The 293T cells were subcultured to adapt to Expression Medium. The cells grew from adherent cells to suspension.

1.2 Transfection System

Cell density of the habituated 293F cells were adjusted to 1×10⁶ cells/ml with Expression Medium. 27 mL of cell suspensions were added to each 75 cm² culture flask.

1.3 Steps of Transfection (Conducted According to Guidelines of Expi293™ Expression System Kit, Life Technologies, USA)

Minicircle DNA having anti-CD19×CD3 genetically engineered antibody gene expression cassette and minicircle DNA having anti-CD20×CD3 genetically engineered antibody gene expression cassette were subjected to the following steps.

(1') 30 ug of minicircle DNA were mixed with 1500 ul of Opti serum-free medium, and reacted at room temperature for 5 minutes. 81 ul of 293 reagent were mixed with 1500 ul of Opti serum-free medium, and reacted at room temperature for 5 minutes.

(2') After the reaction, the two test solution were mixed and incubated at room temperature for 30 minutes.

(3') The resulting solution was added to the culture flask containing 293F cells.

(4') The cells were incubated in a cell incubator under the conditions of 37° C., CO₂ 5% (saturated humidity) for a period of 16 hours to 18 hours. After that, 150 ul of ExpiFectamin 293 Transfection Enhancer1 and 1500 ul of ExpiFectamin 293 Transfection Enhancer2 were added to each culture flask.

(5') The cells were continued to be incubated for 48 hours. The supernatants were collected and subjected to detection or subsequent test.

(2) Purification of anti-CD19×CD3 genetically engineered antibody and anti-CD20×CD3 genetically engineered antibody The supernatants containing anti-CD19×CD3 genetically engineered antibody and supernatants containing anti-CD20×CD3 genetically engineered antibody obtained from step (1) were subjected to the following steps.

1.1 Mechanism: Target protein has His protein tag that can be combined with Ni filler and eluted with imidazole in a high concentration, thus achieving purification of target protein.

1.2 Steps of purification (1) Culture medium containing target protein were mixed with Ni filler and placed in a shaking table at 4° C. overnight, making the target protein combine with Ni filler completely.

(2) Mixture of culture medium and Ni filler were subject to column chromatography, and the Ni filler were collected.

(3) The collected filler were washed with 20 mM of imidazole to remove un-target protein.

(4) 500 mM of imidazole were used to wash 10 mL of target protein.

(5) The eluated target protein were concentrated by a 10K ultra-filtration column, and then washed with PBS to remove imidazole. After that, it was centrifugated. The target protein on the ultra-filtration column were dissolved with T551 culture medium, and preserved. Purified anti-CD19×CD3 genetically engineered antibody and anti-CD20×CD3 genetically engineered antibody were obtained.

Figure 13:
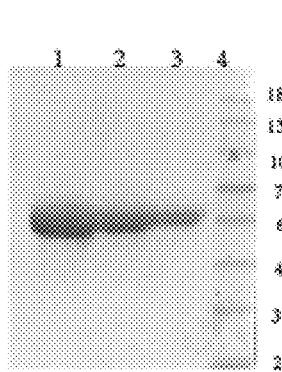
FIG. 13 shows SDS-PAGE of purified anti-CD19×CD3 genetically engineered antibody of Example 17.

In order to fully illustrate the beneficial effects of the present invention, an SDS-PAGE image of the purified anti-CD19×CD3 genetically engineered antibody is provided. As shown in FIG. 13, lanes 1-3 are anti-CD19×CD3 genetically engineered antibodies of different loading amounts. Lane 4 is protein Marker (Thermo Fisher, No.: 26616). FIG. 13 indicates the production of purified anti-CD19×CD3 genetically engineered antibody, 55 Ka.

Example 18

A method for binding activity in vitro using anti-CD19×CD3 genetically engineered antibody comprises the following steps.

(1) Detection of binding activity of anti-CD20×CD3 genetically engineered antibody and Raji cell by flow cytometry (1a) Experimental group, control group 1 and control group 3

Experimental group: The purified anti-CD20×CD3 genetically engineered antibody obtained from Example 17 was mixed with 1% bovine serum albumin (BSA) and phosphate buffered saline (staining buffer) containing 0.02% sodium azide, and incubated on ice for 30 minutes.

The incubation solution was subjected to centrifugation. The obtained cells were washed with PBS twice. Anti-mouse His6 antibody marked by fluorescein isothiocyanate (FITC) were added, and incubated on ice for 30 minutes.

Control group 1: Raji cells were transfected with p2ΦC31 empty plasmid.

Control group 2: Raji cells were transfected with p2ΦC31 empty plasmid, and then incubated on ice for 30 minutes.

The incubation solution was subjected to centrifugation. The obtained cells were washed with PBS twice. Anti-mouse His6 antibody marked by fluorescein isothiocyanate (FITC) were added, and incubated on ice for 30 minutes.

Figure 14:
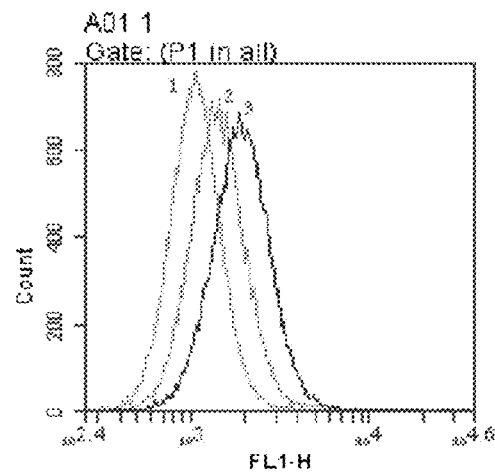
FIG. 14 shows flow cytometry analysis of anti-CD20×CD3 genetically engineered antibody of Example 18.

(1b) The incubation solutions of step (1a) were centrifugated, and the obtained cells were washed with staining buffer twice. We resuspended the cells with 200 μl of staining buffer and detected by flow cytometry. Results are shown in FIG. 14, where curve 1 is control group 1, curve 2 is control group 2 and curve 3 is experimental group. Results indicate that the anti-CD19×CD3 genetically engineered antibody of the present invention is capable of binding CD20 positive Raji cells.

Example 19

A method by using genetically engineered antibody and CIK cells mediated cytotoxicity for Raji cells comprises the following steps.

(1) Raji cells were inoculated on a 96-well cell culture plate ($2\times10^4$/hole, 200 μl). After the appearance of adherent cells, CIK cells were added to culture plates (culture medium was T551) separately according to ratios of CIK cells (effector cell, E) to Raji cells (target cells, T) 2:1, 40:1 and 8:1 (E:T), while recombinant antibody at different concentrations were added to the cell culture wells. Effector cells and target cells were incubated separately and used as control (T). The purified anti-CD19×CD3 genetically engineered antibody of Example 17 (denoted as CD19×CD3 BiTE), anti-CD20×CD3 genetically engineered antibody (denoted as CD20×CD3 BiTE), binding of CD19×CD3 BiTE and CD20×CD3 BiTE were added. A blank control, to which only T551 culture medium was added, was designed as set out in Table 1 and Table 2.

Effector cells (E) and target cells (T) were incubated separately and used as control. The control groups were used to compare with the experimental group and calculate cell killing efficiency. There were three effector cell (E) control groups: 4×104/hole CIK cells (200 μl), $8\times10^4$/hole CIK cells (200 μl) and $16\times10^4$/hole CIK cells (200 μl). There was one target cell (T) control group: $2\times10^4$/hole Raji cells (200 μl).

The CIK cell of the embodiment is D-CIK cell, i.e. dendritic cell activated and cytokine induced killer cell.

(2) After the cells were incubated for 8 hours, CCK-8 was added. After 24 hours, we conducted a detection at 450 nm and calculated killing efficiency.

CCK-8 cell counting kits (DOJINDO, NO.: CK04) were used in this embodiment.

The reagent containing WST-8 can be reduced to water-soluble yellow formazan dye by dehydrogenase in the presence of electron carrier 1-Methoxy PMS. The amount of formazan is proportional to the number of living cells, while the amount of formazan is proportional to its absorbance (absorbance at 450 nm wavelength). Therefore, ELISA may be used to detect absorbance of each well at 450 nm wavelength, and the results may be used for analysis of cell proliferation and toxicity characteristics.

Figure 15:
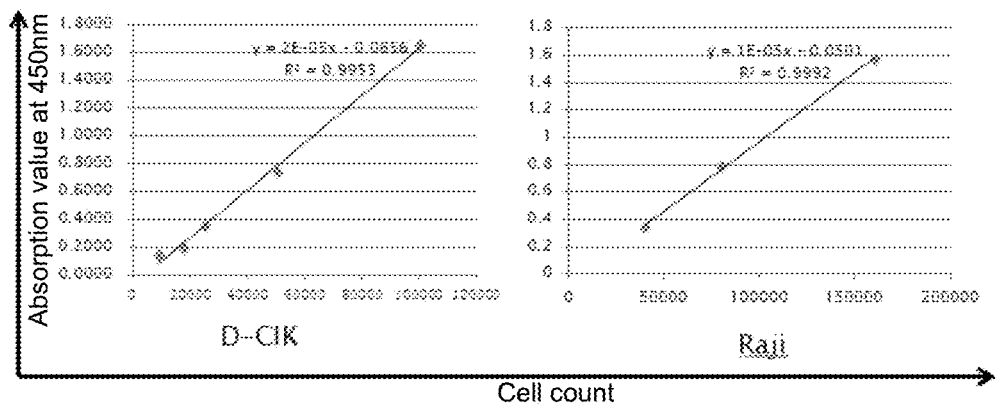
FIG. 15 shows that results of using a CCK-8 cell counting kit as reported in Example 19.

In order to fully explain the beneficial effects of the present invention, CCK-8 cell counting kit was tested in advance to confirm whether it is suitable for D-CIK cells and Raji cells. Experimental results are shown in FIG. 15. From FIG. 15, it can be seen that the CCK-8 cell counting kit can be used in this embodiment because there is a linear relation between the number of D-CIK cells (or Raji cells) and the absorbance value at 450 nm.

Killing efficiency is calculated according to the number of cells after conversion according to the OD values, using the following formula:

Killing efficiency=[1−(effector cells and target cells−corresponding effector cells)/corresponding target cells]×100%

Herein the "effector cells and target cells" represents experimental group that contains effector cells and target cells, "corresponding effector cells" and "corresponding target cells" represents control group that only contains effector cells or target cells.

Figure 16:
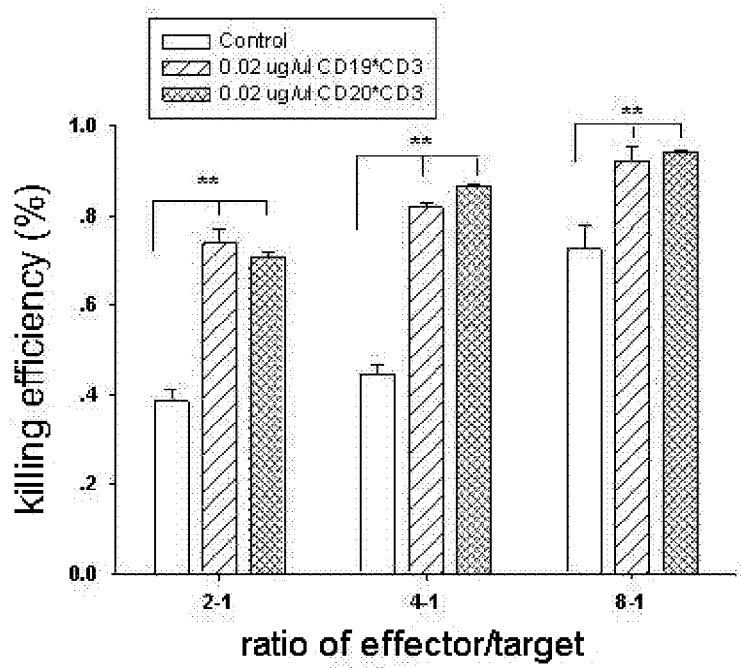
FIG. 16 and FIG. 17 show the detection results of killing Raji cells with D-CIK enhanced by CD19×CD3 and CD20×CD3 BiTE.
Figure 17:
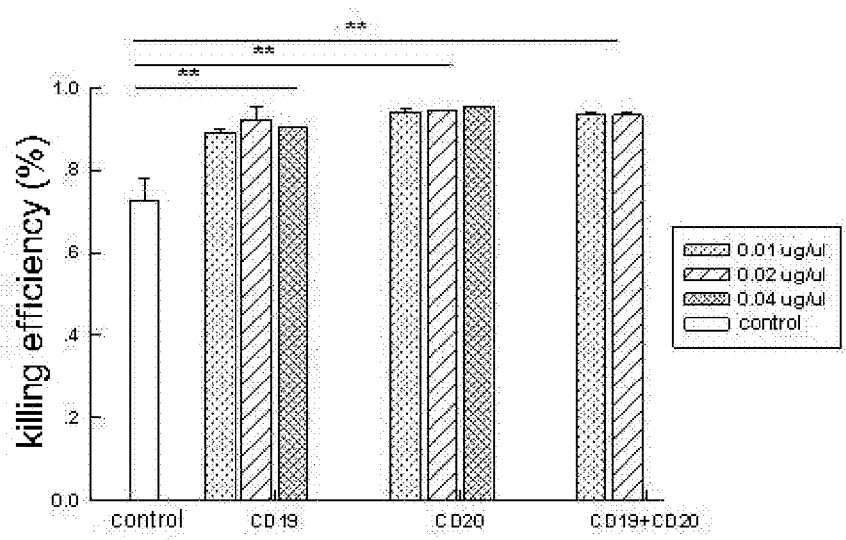

The detection results of killing Raji cells with D-CIK enhanced by CD19×CD3 and CD20×CD3 BiTE are shown in FIG. 16 and FIG. 17.

Parameters in FIG. 16, such as concentration of effector cells, concentration of target cells, ratio of the number of effector cells to target cells, concentration of the minicircle DNA that transfected into effector cells are shown in Table 1.

In Table 1, the experimental group 1 was designed to kill Raji cells by CD19×CD3 BiTE and CIK cells.

The experimental group 2 was designed to kill Raji cells by CD20×CD3 BiTE of different concentrations combined with CIK cells.

The experimental group 3 was designed to kill Raji cells by mixed antibodies (CD19×CD3 BiTE and CD20×CD3 BiTE) of different concentrations combined with CIK cells.

TABLE 1

| Group No. | BiTE | Concentration of BiTE (ug/ul) | Concentration of effector cells (1 × 10$^4$/hole) | Concentration of target cells (1 × 10$^4$/hole) | ratio of effector cells to target cells (x-axis of FIG. 16) |
|---|---|---|---|---|---|
| Experimental group 1 | CD19 × CD3 BiTE | 0.02 | 4 | 2 | 2:1 |
| | | 0.02 | 8 | 2 | 4:1 |
| | | 0.02 | 16 | 2 | 8:1 |
| Experimental group 2 | CD20 × CD3 BiTE | 0.02 | 4 | 2 | 2:1 |
| | | 0.02 | 8 | 2 | 4:1 |
| | | 0.02 | 16 | 2 | 8:1 |
| Control group | T551 culture medium | — | — | 2 | — |
| | | — | — | 2 | — |

In Table 1, the experimental group 1 was designed to kill Raji cells by anti-CD19×CD3 genetically engineered antibody and CIK cells.

The experimental group 2 was designed to kill Raji cells by anti-CD20×CD3 genetically engineered antibody and CIK cells.

In the control group, Raji cells were incubated normally.

In FIG. 16, the notation "**" represents P<0.01, y-axis is ratio of the number of effector cells and target cells. 2-1, 4-1 and 8-1 means 2:1, 4:1 and 8:1, respectively. X-axis is percent of killing cells. From FIG. 16, it can be seen that experimental group 1 and 2 may obviously enhance the ability of CIK cells on killing Raji cells.

Further, under the same concentration of genetically engineered antibody, the higher the efficiency of the ratio of effector/target, CIK cells show stronger ability on killing Raji cells. That is, CIK cells activated by anti-CD19×CD3 genetically engineered antibody or anti-CD20×CD3 genetically engineered antibody show stronger ability on killing Raji cells.

Parameters in FIG. 17, such as concentration of effector cells, concentration of target cells, and concentration of genetically engineered antibody are shown in Table 2.

In the control group, Raji cells were incubated normally.

In FIG. 17, the notation "**" represents P<0.01, x-axis is percent of killing cells. From FIG. 17, it can be seen that experimental group 1-3 may obviously enhance the ability of CIK cells on killing Raji cells.

In addition, under a condition of: ratio of effector/target cells 8:1, transfection concentration of genetically engineered antibody 0.01-0.04 ug/ul, CIK cells of the experimental groups 1-3 show stronger ability on killing Raji cells.

These results indicated that the anti-CD19×CD3 genetically engineered antibody, anti-CD20×CD3 genetically engineered antibody, and mixed antibodies of anti CD19×CD3 and anti-CD20×CD3 genetically engineered antibody may significantly activate T cells, thus improving ability of T cells on killing tumor cells and cancer cells.

Example 20

A method for treating tumor using minicircle DNA having anti-CD19×CD3 genetically engineered antibody gene expression cassette and CIK cells comprises the following steps.

TABLE 2

| Group No. (y-axis of FIG. 17) | BiTE and its combination | Concentration of BiTE (ug/ul) | Concentration of effector cells (1 × 10$^4$/hole) | Concentration of target cells (1 × 10$^4$/holw) | ratio of effector cells to target cells |
|---|---|---|---|---|---|
| Experimental group 1 (CD19) | CD19 × CD3 BiTE | 0.01 | 16 | 2 | 8:1 |
| | | 0.02 | 16 | 2 | 8:1 |
| | | 0.04 | 16 | 2 | 8:1 |
| Experimental group 2 (CD20) | CD20 × CD3 BiTE | 0.01 | 16 | 2 | 8:1 |
| | | 0.02 | 16 | 2 | 8:1 |
| | | 0.04 | 16 | 2 | 8:1 |
| Experimental group 3 (CD19 × CD20) | CD19 × CD3 BiTE and CD20 × CD3 BiTE | 0.01 | 16 | 2 | 8:1 |
| | | 0.02 | 16 | 2 | 8:1 |
| | | — | — | — | — |
| Control group | T551 | — | — | 2 | — |
| | | — | — | 2 | — |
| | | — | — | 2 | — |

Experimental animals obtained from Chinese Medicine Laboratory Animal Center (NOD/SCID, nonobese diabetic/severe combined immunodeficien).

Experimental groups:

(a) Control: saline of the same volume;

(b) tumor animal model group: injected Raji cells 5*E06/each;

(c) therapy group: injected Raji cells 5*E06/each, injected D-CIK cells 5*E06/each, 3 times (once a day, 3 times);

(d) combination therapy group: injected CD19×CD3 minicircle DNA, once injection; injected Raji cells 5*E06/each, injected D-CIK cells 5*E06/each, 3 times (once a day, 3 times).

Experimental Procedure (1) A $(0.7{\sim}1.9)\times10^6$ cell/mL suspension of tumor cells were prepared with a nutrient solution (PBS solution). 40 mice were intraperitoneal injected with Raji cells 5*E06 (in a control group saline of the same volume were injected). After 9 to 21 days, lymphoma mouse model was established.

(2) The mouse model of lymphoma obtained from step (1) were subjected to the procedure as described in the Experimental groups (c) and (d). The therapy group was injected with D-CIK cells (once a day, 3 times); combination therapy group was injected with CD19×CD3 minicircle DNA, once injection; injected with D-CIK cells (5*E06/each, once a day, 3 times). The control group and tumor animal model group were injected with saline of the same volume.

Figure 18:
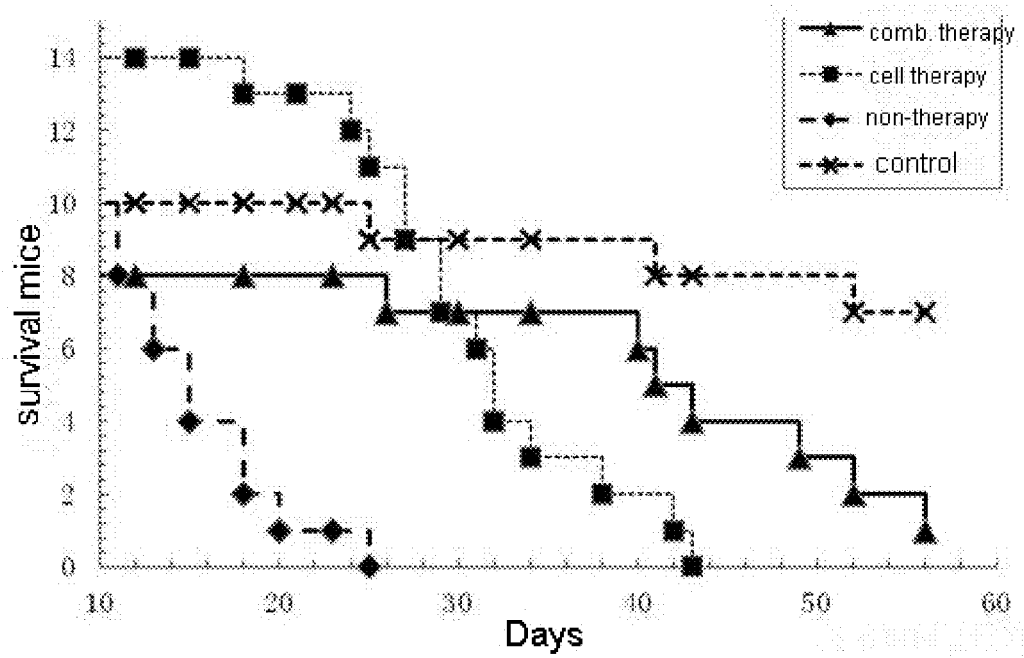
FIG. 18 and FIG. 19 show survival curves of B lymphoma mice.
Figure 19:
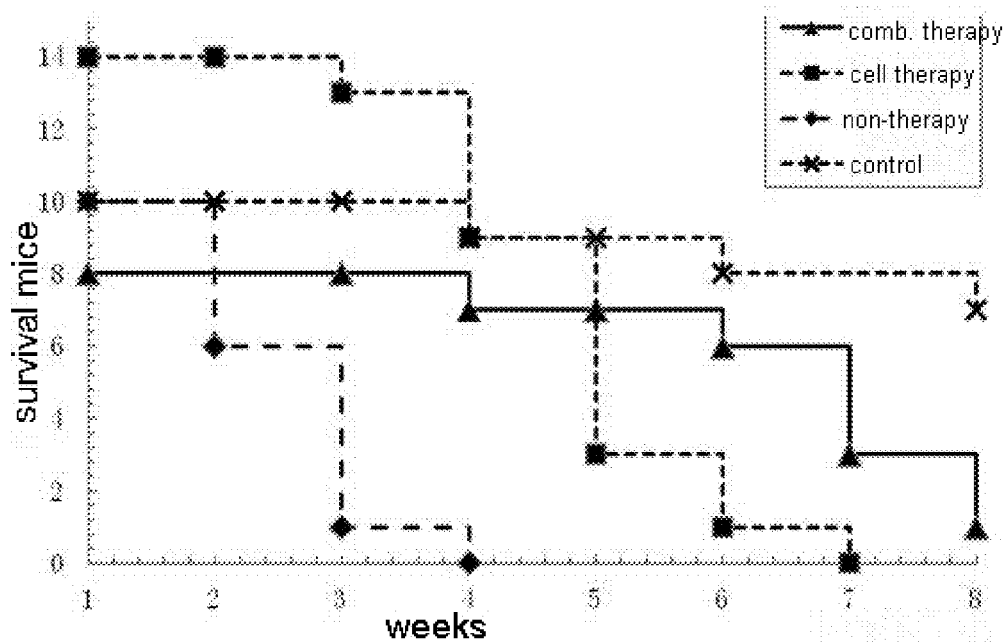

Survival curves of B lymphoma mice treated with minicircle DNA having anti-CD19×CD3 genetically engineered antibody gene expression cassette are shown in FIG. 18 (in days) and FIG. 19 (in weeks). From FIG. 18 and FIG. 19, it can be seen that, compared with control group and tumor animal model group, the therapy group and combination therapy group of the present application show ability on killing tumors. However, the combination therapy group achieves a better result and prolongs survival time of mouse model of lymphoma. These indicated that the minicircle DNA having anti-CD19×CD3 genetically engineered antibody gene expression cassette of the present invention may be used for the treatment of tumors. In addition, the minicircle DNA having anti-CD19×CD3 genetically engineered antibody gene expression cassette of the present invention may activate CIK cells and enhance its ability on killing tumors.

What is claimed is:

1. A minicircle DNA comprising a genetically engineered antibody gene expression cassette, wherein said genetically engineered antibody gene expression cassette comprises a genetically engineered antibody gene encoding a dual-targeting bispecific antibody comprising a first targeting immune effector cell antigen epitope binding site and a second tumor cell antigen epitope binding site, wherein the minicircle DNA has an attR site and said gene expression cassette comprises a promoter, a base sequence encoding an immunoglobulin K chain signal peptide, a base sequence encoding a Flag tag, said genetically engineered antibody gene, a base sequence encoding a His6 tag, a stop codon and a polyA tailing signal linked sequentially, wherein the amino acid sequence of the bispecific single chain antibody is selected from the group consisting of (a)-(h):

(a) $V_L$CD19-linker1-$V_H$CD19-linker2-$V_L$CD3-linker1-$V_H$CD3,
(b) $V_H$CD19-linker1-$V_L$CD19-linker2-$V_L$CD3-linker1-$V_H$CD3,
(c) $V_L$CD19-linker1-$V_H$CD19-linker2-$V_H$CD3-linker1-$V_L$CD3,
(d) $V_H$CD19-linker1-$V_L$CD19-linker2-$V_H$CD3-linker1-$V_L$CD3,
(e) $V_L$CD20-linker1-$V_H$CD20-linker2-$V_L$CD3-linker1-$V_H$CD3,
(f) $V_H$CD20-linker1-$V_L$CD20-linker2-$V_L$CD3-linker1-$V_H$CD3,
(g) $V_L$CD20-linker1-$V_H$CD20-linker2-$V_H$CD3-linker1-$V_L$CD3,
(h) $V_H$CD20-linker1-$V_L$CD20-linker2-$V_H$CD3-linker1-$V_L$CD3, where the amino acid sequence of $V_L$CD19 is SEQ ID NO: 1; the amino acid sequence of $V_H$CD19 is SEQ ID NO: 2; the amino acid sequence of $V_L$CD3 is selected from SEQ ID NO: 3 and SEQ ID NO: 4; the amino acid sequence of $V_H$CD3 is selected from SEQ ID NO:5, SEQ ID NO:6 and SEQ ID NO:7; the amino acid sequence of linker1 is selected from SEQ ID NO:8, SEQ ID NO:9 and SEQ ID NO:10; the amino acid sequence of linker2 is SEQ ID NO: 11; the amino acid sequence of $V_L$CD20 is SEQ ID NO: 29; the amino acid sequence of the $V_H$CD20 is SEQ ID NO: 30.

2. A method for preparing a minicircle DNA comprising a genetically engineered antibody gene expression cassette, comprising:

(1) providing or preparing a minicircle DNA recombinant parental plasmid comprising a genetically engineered antibody gene expression cassette, wherein said minicircle DNA recombinant parental plasmid is obtained by inserting a gene sequence of said genetically engineered antibody gene expression cassette into multiple cloning sites of a minicircle DNA empty plasmid, wherein the minicircle DNA recombinant parental plasmid has site-specific recombination sites, wherein the minicircle DNA empty plasmid is p20C31 plasmid or pMC.BESPX plasmid, and wherein the genetically engineered antibody gene expression cassette comprises a promoter, a base sequence encoding immunoglobulin K chain signal peptide, a base sequence encoding a Flag tag, genetically engineered antibody gene, a base sequence encoding a His6 tag, a stop codon and a polyA tailing signal linked sequentially;

(2) transforming host strains with the minicircle DNA recombinant parental plasmid comprising the genetically engineered antibody gene expression cassette obtained from step (1), producing minicircle DNA and backbone DNA through site-specific recombination of the site-specific recombination sites in the presence of OC31 recombinase, wherein the site-specific recombination comprises non-reversibly producing bacterial plasmid backbone DNA containing an attL site and minicircle DNA containing an attR site; and (3) isolating and purifying the minicircle DNA and backbone DNA obtained from step (2), wherein step (3) comprises cutting the bacteria plasmid DNA containing the attL site with I-Sce endonuclease to produce linear DNA fragments; and purifying the minicircle DNA wherein the genetically engineered antibody gene has a base sequence encoding a bispecific single chain antibody amino acid sequence comprising a first targeting immune effector cell antigen epitope binding site and a second tumor cell antigen epitope binding site, and the amino acid sequence of the bispecific single chain antibody is selected from the group consisting of (a)-(h):

(a) $V_L$CD19-linker1-$V_H$CD19-linker2-$V_L$CD3-linker1-$V_H$CD3,
(b) $V_H$CD19-linker1-$V_L$CD19-linker2-$V_L$CD3-linker1-$V_H$CD3,
(c) $V_L$CD19-linker1-$V_H$CD19-linker2-$V_H$CD3-linker1-$V_L$CD3,
(d) $V_H$CD19-linker1-$V_L$CD19-linker2-$V_H$CD3-linker1-$V_L$CD3,
(e) $V_L$CD20-linker1-$V_H$CD20-linker2-$V_L$CD3-linker1-$V_H$CD3,
(f) $V_H$CD20-linker1-$V_L$CD20-linker2-$V_L$CD3-linker1-$V_H$CD3,
(g) $V_L$CD20-linker1-$V_H$CD20-linker2-$V_H$CD3-linker1-$V_L$CD3,
(h) $V_H$CD20-linkerl1-$V_L$CD20-linker2-$V_H$CD3-linker1-$V_L$CD3, where the amino acid sequence of $V_L$CD19 is SEQ ID NO: 1; the amino acid sequence of $V_H$CD19 is SEQ ID NO: 2; the amino acid sequence of $V_L$CD3 is selected from SEQ ID NO: 3 and SEQ ID NO: 4; the amino acid sequence of $V_H$CD3 is selected from SEQ ID NO:5, SEQ ID NO:6 and SEQ ID NO:7; the amino acid sequence of linker1 is selected from SEQ ID NO:8, SEQ ID NO:9 and SEQ ID NO:10; the amino acid sequence of linker2 is SEQ ID NO: 11; the amino acid sequence of $V_L$CD20 is SEQ ID NO: 29; the amino acid sequence of the $V_H$CD20 is SEQ ID NO: 30.

* * * * *